(12) United States Patent
Kiros et al.

(10) Patent No.: US 6,999,607 B2
(45) Date of Patent: Feb. 14, 2006

(54) METHOD AND APPARATUS FOR AUTOMATED CELLULAR BIOINFORMATICS

(75) Inventors: Eskinder Kiros, San Jose, CA (US); Ping Ling, San Bruno, CA (US); Robert J. Muller, San Francisco, CA (US); Ramesh Venkat, Fremont, CA (US); Wesley A. Zink, San Francisco, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 43 days.

(21) Appl. No.: 10/467,183
(22) PCT Filed: Feb. 20, 2002
(86) PCT No.: PCT/US02/05266
§ 371 (c)(1),
(2), (4) Date: Jan. 12, 2004
(87) PCT Pub. No.: WO02/066961
PCT Pub. Date: Aug. 29, 2002

(65) Prior Publication Data
US 2004/0117124 A1 Jun. 17, 2004

Related U.S. Application Data
(60) Provisional application No. 60/270,314, filed on Feb. 20, 2001.

(51) Int. Cl.
*G06K 9/00* (2006.01)
(52) U.S. Cl. .................................................. 382/128
(58) Field of Classification Search ................ 382/128, 382/133, 134; 702/19, 20, 21, 27; 707/3, 707/4, 6; 356/36, 39; 706/4, 5, 46; 435/6
See application file for complete search history.

(56) References Cited

U.S. PATENT DOCUMENTS

| 5,548,661 | A | 8/1996 | Price et al. |
| 5,989,835 | A | 11/1999 | Dunlay et al. |

(Continued)

FOREIGN PATENT DOCUMENTS

WO   WO 96/09598   9/1995

(Continued)

OTHER PUBLICATIONS

Clouard et al., "Borg: A Knowledge-Based System for Automation Generation of Image Processing Programs," XP-00082196, IEEE, vol. 21, No. 2, 1999, 128-144.

(Continued)

*Primary Examiner*—Jose L. Couso
(74) *Attorney, Agent, or Firm*—Beyer Weaver & Thomas LLP

(57) ABSTRACT

An automated system that conducts, monitors, and validates a cell-line-based biological experiment including one or more treatment compounds or other external stimuli. In one preferred embodiment, the system comprises two principal subsystems, and optionally accessory subsystems. A first principal subsystem is an automated laboratory experiment manager for designing the biological experiment, for constructing an assay plate used to conduct the biological experiment, and for managing one or more of the processes that constitute the biological experiment. A second principal subsystem is an automated data analysis manager for analyzing images, for instance produced by the image production system, to detect image data including biological markers and objects, for analyzing the resulting image data to produce biological data, and for analyzing the biological data to produce biological phenotypes and treatment compound signatures.

20 Claims, 38 Drawing Sheets

U.S. PATENT DOCUMENTS

| | | | |
|---|---|---|---|
| 6,103,479 | A | 8/2000 | Taylor |
| 6,272,235 | B1 * | 8/2001 | Bacus et al. ............... 382/133 |
| 6,743,576 | B1 | 6/2004 | Sabry et al. |
| 6,768,982 | B1 * | 7/2004 | Collins et al. ............... 706/45 |
| 2002/0141631 | A1 | 10/2002 | Vaisberg et al. |
| 2002/0154798 | A1 | 10/2002 | Cong et al. |
| 2002/0155420 | A1 | 10/2002 | Vaisberg et al. |
| 2003/0228565 | A1 | 12/2003 | Oestreicher et al. |

FOREIGN PATENT DOCUMENTS

| | | |
|---|---|---|
| WO | WO 97/45730 | 12/1997 |
| WO | WO 98/38490 | 9/1998 |
| WO | WO 99/39184 | 8/1999 |
| WO | WO 99/67739 | 12/1999 |
| WO | WO 00/03246 | 1/2000 |
| WO | WO 00/17624 | 3/2000 |
| WO | WO 00/17643 | 3/2000 |
| WO | WO 00/26408 | 5/2000 |
| WO | WO 00/29984 | 5/2000 |
| WO | WO 00/50872 | 8/2000 |
| WO | WO 00/60356 | 10/2000 |
| WO | WO 00/70528 | 11/2000 |
| WO | WO00/72258 | 11/2000 |
| WO | WO0072258 | * 11/2000 |

OTHER PUBLICATIONS

Giuliano, et al, "High-Content Screening: A New Approach to Easing Key Bottlenecks in the Drug Discovery Process", Journal of Biomolecular Screening, vol. 2, No. 4, 1997, pp. 249-259.

"Q3DM", Q3DM homepage, http://64.177.162.169/flashsite/index.html, printed from website on Mar. 1, 2001, pp. 18-1-30.

"Automated Cell", Automated Cell/Gaining a Technological Edge, http://automatedcell.com/technology/index.html, printed from website on Mar. 9, 2001, pp. 1-24.

Kapur, et al, "Design and Fabrication of Spatially Controlled Miniaturized Organ Systems from Stem Cells ", U.S. Appl. No. 60/127,339, filed Apr. 1, 1999, pp. 1-22.

Adams, et al., "Cell patterning on glass and polymeric substrates", U.S. Appl. No. 60/138,119, filed Jun. 7, 1999, pp. 1-17.

Dunaly et al., "Data Management and Presentation Methods", U.S. Appl. No. 60/140,240, filed Jun. 21, 1999, pp. 1-163.

Sabry et al., "Database Method For Predictive Cellular Bioinformatics," U.S. Appl. No. 09/310,879, filed May 14, 1999.

Vaisberg et al., "Database System Including Computer for Predictive Cellular Bioinformatics," U.S. Appl. No. 09/311,996, filed May 14, 1999.

Vaisberg et al., "Classifying Cells Based On Information Contained In Cell Images," U.S. Appl. No. 09/729,754, filed Dec. 14, 2000.

* cited by examiner

| | A | B | C | D | E | F | G | H |
|---|---|---|---|---|---|---|---|---|
| 1 | | Cytometrix 1.0 - T-175 Cell Plating Worksheet and Log | | | | | | |
| 2 | | | | | | | | |
| 3 | | | | fill in yellow squares | | | | |
| 4 | | Initials | Date | Cell Line | Number of T175 Flasks | Estimated Confluency | total # mls of cell suspension | |
| 5 | | rd | 11/3/2000 | SK-OV-3 | 1 | 85% | 10 | |
| 6 | | | Media Working # | w755 | Starting Passage Number | | 15 | |
| 7 | | | Trypsin | A186 | End passage number | | 16 | |
| 8 | | | PBS | R291 | | | | |
| 9 | | | | | | | | |
| 10 | | | | | | | | |
| 11 | | Cell counts after trypsinization - Use either CC or hemocytometer | | | | | | |
| 12 | | | | # cells/ml after suspension ($10^4$) | | | | |
| 13 | | | Hemocytometer - Average of 4 squares (SOP# 1003) | | | Counter Average | 49 | |
| 14 | | | | | | | | |
| 15 | | | Average # of cells per flask ($10^6$) | 4.90E+06 | Average # cells/ml | 4.90E+05 | | |
| 16 | | | Total number of cells | 4.90E+06 | | | | |
| 17 | | | | | | | | |
| 18 | | Plating into T175 | | | | | | |
| 19 | | | Seed Density ($x10^6$) | | | | | |
| 20 | | | Maintenance | | | | | |
| 21 | | Cell Line | (3-4 days) | (for 48 hr.) | (for 72 hr.) | | | |
| 22 | | | | | | | | |
| 23 | | A498 | 1.5 | 3 | | | | |
| 24 | | | | | | | | |
| 25 | | A549 | 2 | 3 | | | | |
| 26 | | | | | | | | |
| 27 | | DU-145 | 2.5 - 3 | | 3.5 | | | |
| 28 | | | | | | | | |
| 29 | | HUVEC | 2 | 3 | | | | |
| 30 | | | | | | | | |
| 31 | | SF268 | 1.5 | 3 | | | | |
| 32 | | | | | | | | |
| 33 | | SK-OV-3 | 2 - 2.5 | | 4 | | | |
| 34 | | | | | | | | |
| 35 | | | | | | | | |
| 36 | | Desired seed density/flask ($10^6$) | | 2 | | | | |
| 37 | | Media add to T-175 | | | | | | |
| 38 | | Add concentrated cell stock (ml) | | 4.1 | | | | |
| 39 | | Number of T-175s made | | 1 | | | | |
| 40 | | | | | | | | |
| 41 | | Save as "Date_cell line" in Operations log folder on Kinesin | | | | | | |
| 42 | | | | | | | | |

Figure 14B

Cytometrix 1.0 - 384-well cell plating Worksheet and Log fill in yellow squares

| Initials | Date | Cell Line | Number of T175 Flasks | Estimated Confluency | total # mls of cell suspension |
|---|---|---|---|---|---|
| rd | 10/6/2000 | HUVEC | 2 | 95% | 20 |
| | Media Working # | w706 | Starting Passage Number | | 16 |
| | Trypsin | A179 | End passage number | | 17 |
| | PBS | r284 | | | |

Cell counts after trypsinization - Use CC AND hemocytometer

| | # cells/ml after suspension (*10⁵) | | | |
|---|---|---|---|---|
| Hemocytometer - Average of 4 squares (SOP#1003) | 85 | Coulter Counter Average (SOP#1002) | 85 | |
| Average # of cells per flask (*106) | 8.50E+06 | Average # cells/ml | 8.50E+05 | |
| Total # of cells | 1.70E+07 | | | |

Plating into 384 well plates - 20 ul/well - Cytometrix 1.0

| Cell line | cells/well | cells/ml |
|---|---|---|
| A498 | 1600 | 80000 |
| A549 | 1000 | 50000 |
| DU-145 | 1200 | 60000 |
| HUVEC | 1800 | 90000 |
| SF268 | 1200 | 60000 |
| SK-OV-3 | 1600 | 80000 |

| | |
|---|---|
| Number 384 well plates | 15 |
| Desired cell number/well | 1800 |
| Total media ml for Celstir 250 ml | 200 |
| Total number of cells needed | 1.80E+07 |

| | |
|---|---|
| Add media for Celstir | 178.8 |
| Add concentrated cell stock (ml) | 21.2 |

Save as " Date_cell line_384" in Operations log folder on Kinesin

Figure 14C

METHOD AND APPARATUS FOR AUTOMATED CELLULAR BIOINFORMATICS

CROSS-REFERENCE TO RELATED APPLICATIONS

This application is a 371 of PCT/US02/05266, filed Feb. 20, 2002 which claims priority under 35 USC §119(e) from U.S. Provisional Patent Application No. 60/270,314, filed Feb. 20, 2001, titled "METHOD AND APPARATUS FOR AUTOMATED CELLULAR BIOINFORMATICS." The provisional application is incorporated herein by reference in its entirety and for all purposes.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyrights whatsoever.

FIELD OF THE INVENTION

The present invention relates to computer-automated cellular biological systems. More particularly still, the present invention relates to computer-automated cellular biological systems for designing, conducting, monitoring, and validating a cell-line-based biological experiment including a treatment compound.

BACKGROUND OF THE INVENTION

The techniques of cellular biology have been applied to numerous fields of scientific inquiry. A cell-line-based biological experiment on specific biological markers is typically a process that groups a set of assay plates into a collection designed to achieve a scientific purpose, or is a composite of several such processes. One known technique in cytobiological research involves the analysis of cellular images from such experiments.

Experiments typically combine sets of assay plates to achieve some scientific purpose. An assay plate is a collection of wells arranged in groups of wells. A well group is a set of wells on an assay plate, or ranging across two or more assay plates, that represents a specific collection of wells for distinct analysis.

A treatment is a particular drug or other external stimulus (or a combination of stimuli, drugs, or drugs+stimulus/stimuli) to which wells are exposed on an assay plate. Every plate typically contains multiple sets of wells that constitute treatment well groups. A treatment plate is a plate containing an array of treatment compounds in well groups. Each well group may contain one or more treatment compounds in each well (the treatment). Each treatment well in a group contains a specific dilution (or dose) of the group treatment. Typically assay plate wells get a specific amount of compound from the corresponding well on the treatment plate.

A well image is one of several possible images of a single well and is the smallest unit of analysis in the system. Well images relate to specific cell markers and are at specific sites in the well. Typically cells of a specified type are introduced into each of the wells of the assay plate by a process sometimes referred to as plating. (Note that a given well may include cells of different types, specifically selected for a particular experiment.) A certain amount of a reagent medium is added to each well to promote cell growth. A certain amount of a treatment is added to each well, combining with the cells and media already present. One or more reagents may comprise a treatment. After the treatment has acted upon the cells in the several wells of the assay plate for the time specified by the experimenter, the cells are typically washed, fixed, and stained. An experiment may contain groups of plates fixed at different times (time points). Images, typically photomicroscopic images, are taken for the cells in the several wells of the assay plate or plates. Finally, an experimenter analyzes these images to determine the effect of the treatment.

Each of these steps is exacting, repetitive, and many of them require significant amounts of time from highly trained experimenters to complete. A thorough analysis of the effects of one treatment on one cell line may require tens or even hundreds of wells. This is multiplied where the treatment is analyzed against multiple cell lines, or where a cell line is used to determine the effects of multiple treatments.

What is needed is a methodology which provides tools that allow a designer to design an experiment that combines cell lines, marker sets, time points, and treatment plates. These tools should permit the full specification of the experimental process through a process model that generates a process, or collection of tasks. The system should provide the designer with the ability to specify the structure of the experimental process. The system should then specify the processes and tasks for each experiment, automating the process where possible.

The system should enable a user to plan for and maintain adequate experimental infrastructure for planned experiments. By way of illustration, this infrastructure includes, but is not limited to hardware, software, reagents, treatments, and maintenance processes. The system should track the infrastructure of experiments by tracking the individual hardware systems, software systems, reagents, treatments, and maintenance processes required to conduct the experiment. The system should provide reports as planning tools for users to help them to keep adequate supplies and systems on hand and in good repair.

Automated milestones, for instance barcode scanning, task completion updates, and so forth, should be implemented to provide tracking capabilities that give designers, supervisors, and experimenters the ability to obtain experiment status and to intervene in the process where required, preferably through remote interfaces.

The system should provide a full range of tools for validating experimental results. The system should validate experimental results by storing the results of the experiment and by enabling feedback from scientific analysis of the results. Experimental result validation consists of internal consistency of the results and reproducibility of the results. These consistency and reproducibility metrics provide means for designers and experimenters to identify result failures in images, wells, and plates. By way of illustration, but not limitation, consistency metrics may include cell distribution, focus/exposure tests, contamination tests, and control measure consistency with respect to benchmarks. Examples of reproducibility metrics include variance or standard deviation or coefficient of variation of consistency metrics.

The system should provide failure and defect tracking tools to track experimental defects and the failures they cause.

To create a system for validating experimental processes the system should assist in validating experimental processes by storing the processes and tasks undertaken as part of the experiment. These process and task objects provide a complete history of the experiment with all significant milestones recorded with their date and time together with their process models, reusable protocols for generating the process for each experiment. The failure and defect tracking systems track defects and failures in the processes and tasks reported by the system and its users, both of which are sometimes referred to generically hereinafter as "actors".

The system should be capable of creating reusable information, or feedback, about systems failures that is useful for improving the system. Users could thus use this system to improve the visibility of failures within the organization and to improve communication with respect to failures.

The system should be capable of creating reusable information about opportunities to improve the system. Users could thus also use this system to improve the visibility and communication of progress in realizing opportunities within the organization. The system should provide for creating reusable information, or feedback about specific instances of the system that lets users make comments on operational systems. It should further enable management to plan improvement work based on prioritization of the comments.

The system should enable users, applications, and database servers to report and track system defects, and to provide management the ability to plan improvement work based on prioritization of defect fixing and to understand the current situation with respect to the life cycle of defects in the overall system. Managers can also use this information to improve the visibility of defects within the organization and to improve communication with respect to defects.

Optimally, the system should present a flexible, fully automated system for applying image and data analysis algorithms to input images that optimizes image and analysis throughput. The system should permit easy modification of the algorithm structure and easy control of runtime processing. Developers should be able to add new analytical transactions to the system quickly and easily, and operators should be able to control and prioritize analysis jobs using the running system.

SUMMARY

The present invention meets these needs with an automated system for conducting, monitoring, and validating a cell-line-based biological experiment including a treatment compound or other external stimulus. Sometimes, the automated system is referred to herein as "Cytometrix™." In one preferred embodiment, the system comprises two principal subsystems, and optionally three accessory subsystems.

The first principal subsystem is an automated laboratory experiment manager for designing the biological experiment, for constructing an assay plate used to conduct the biological experiment, and for managing one or more of the processes that constitute the biological experiment.

The second principal subsystem is an automated data analysis manager for analyzing images, for instance produced by the image production system, to detect image data including biological markers and objects, for analyzing the resulting image data to produce biological data, and for analyzing the biological data to produce biological phenotypes (sometimes represented as a quantitative phenotype) and treatment compound signatures (sometimes represented as stimulus response curves).

A first accessory subsystem is an image production system for performing photomicroscopy of at least a portion of the assay plate responsive to directions from the laboratory experiment manager, thereby producing an image of the at least a portion of the assay plate.

The second accessory subsystem is a database system for storing data including at least one of the image, the image data, the biological data, the biological phenotypes and treatment compound signatures.

Finally, the third accessory subsystem is a report generator for providing secure access to the data stored in the database system, and, responsive to a user request, for generating a report compiled from the data.

The system also includes several auxiliary components including, but specifically not limited to, components for tracking defects within the system, and for tracking one or more of the processes of the system.

The present invention provides a flexible and easy-to-use system for the design of cell-line-based biological experiments on specific biological markers. It provides tools that allow a designer to design an experiment that combines cell lines, marker sets, and treatment plates into a collection of assay plates. These tools also permit the full specification of the experimental process through a process model that generates a process, or collection of tasks. The system's process modeling features provide the designer the ability to specify the structure of the experimental process. The system then generates processes and tasks for each experiment that automate the process where possible. Automated milestones including but not limited to barcode scanning, and task completion updates, provide tracking capabilities that give users the ability to get experiment status and to intervene in the process where required, preferably through remote interfaces.

The system enables users to plan for and maintain adequate experimental infrastructure, including but not limited to hardware, software, reagents, treatments, and maintenance processes for planned experiments. The system tracks the infrastructure of experiments by tracking the individual hardware systems, software systems, reagents, treatments, and maintenance processes. Reports provide planning tools for users that help them to keep adequate supplies and systems on hand and in good repair.

The system helps to validate experimental results by storing the results and by enabling feedback from scientific analysis of the results. Experimental result validation includes checks for internal consistency of the results and reproducibility of the results. Consistency metrics and reproducibility metrics provide means for designers and experimenters to identify result failures in images, wells, and plates. The failure and defect tracking systems track these defects and the failures they cause. The stored results thus form a part of the experimental protocol The system helps to validate experimental processes by storing the processes and tasks undertaken as part of the experiment. These process and task objects provide a complete history of the experiment with all significant milestones recorded with their date and time together with their process models, reusable protocols for generating the process for each experiment. The failure and defect tracking systems track defects and failures in the processes and tasks reported by the process actors. The stored process information thus forms a part of the experimental protocol.

The system includes an information system that lets users, applications, and database servers create and track system failures. The invention also provides applications that enable management to plan improvement work based on prioritization of the failures and to understand the current situation with respect to the life cycle of failures in the overall system. Managers can also use this system to improve the visibility of failures within the organization and to improve communication with respect to failures.

To create reusable information or feedback about opportunities to improve the system, it builds an information system that enables users to suggest and track improvement opportunities. It also provides applications that enable management to plan improvement work based on prioritization of the opportunities. Managers can also use this system to improve the visibility and communication of progress in realizing opportunities within the organization. The system also enables users to make comments on operational systems, and provides applications that enable management to plan improvement work based on prioritization of the comments.

The system enables users to create reusable information or feedback about systems' defects that is useful for improving the system. It builds an information system that lets users, applications, and database servers create and track system defects. The system further provides applications that enable management to plan improvement work based on prioritization of defect fixing and to understand the current situation with respect to the life cycle of defects in the overall system. Managers can also use this system to improve the visibility of defects within the organization and to improve communication with respect to defects.

The principles of the present invention implement a fully automated system for applying image and data analysis algorithms to input images. The system first determines whether there are input images. If necessary, the system preprocesses the images into an appropriate format and location, then notifies a server group that image analysis can start. Each analysis transaction results in a results data set in a database. Transaction data dependencies result in input data from prior transactions read from the database as input to a new transaction.

The system optimizes image and analysis throughput. Each server processes a transaction comprising a minimal set of operations in the overall analysis sequence, optimizing parallel processing where possible to improve performance throughput.

The system permits easy modification of the algorithm structure and easy control of runtime processing. Developers are able to add new analytical transactions to the system quickly and easily, and operators are able to control and prioritize analysis jobs using the running system.

Another aspect of the invention pertains to automated methods for analyzing a plurality of cellular images. The methods may be characterized by the following sequence: (a) from a plurality of image analysis tasks, identifying a next image analysis task for execution; (b) selecting one of a plurality of feature extractor servers available to handle the next image analysis task; (c) identifying an algorithm for extracting features as part of the next image analysis task; and (d) executing the algorithm under the control of the selected feature extractor. In many important embodiments, the image analysis task characterizes a cellular organelle, a material in the cell, or a combination thereof. In some more specific examples, the image analysis task determines the shape of a cell, characterizes the nucleic acid of a cell, characterizes the Golgi of a cell, or a combination thereof.

While the invention can be implemented on a number of different software architectures, in one preferred embodiment, the invention employs a supervisor entity that identifies the next image task and selects the feature extractor server to handle the next image analysis task. The identified algorithm is then imported into the selected feature extractor for execution. Further, the method may involve inputting one or more selected cellular images required for the image analysis task. Preferably, these images are generated using a process model generated by an automated laboratory experiment manager for designing the biological experiment. The method may further involve inputting parameters required to execute the algorithm from a database. After the image analysis task is completed, the feature extractor server may be returned to a queue of available feature extractor servers.

In a larger context, the method may further comprise: (a) receiving data representing a design of a biological experiment defining an assay plate and comprising one or more processes involving forming at least one image of at least a portion of at least one well of the assay plate; and (b) directing the biological experiment in accordance with the data to generate the at least one of the plurality of cellular images from at least a portion of at least one well of the assay plate.

These and other advantages and details of the present invention will become apparent upon reading the following detailed description.

BRIEF DESCRIPTION OF THE DRAWINGS

FIGS. 14B and 14C show suitable spreadsheets showing two types of plating in accordance with this invention.

DETAILED DESCRIPTION

System Overview

The succeeding discussion centers on one or more preferred embodiments of the present invention, implemented by a number of hardware and software components. It will be understood by those having skill in the art that where the embodiments enumerated herein specify certain commercially available hardware, software, or services, these are by way of example. The principles of the present invention are capable of implementation utilizing a wide variety of hardware, software and service combinations, and these principles specifically contemplate all such embodiments.

Figure 1A:
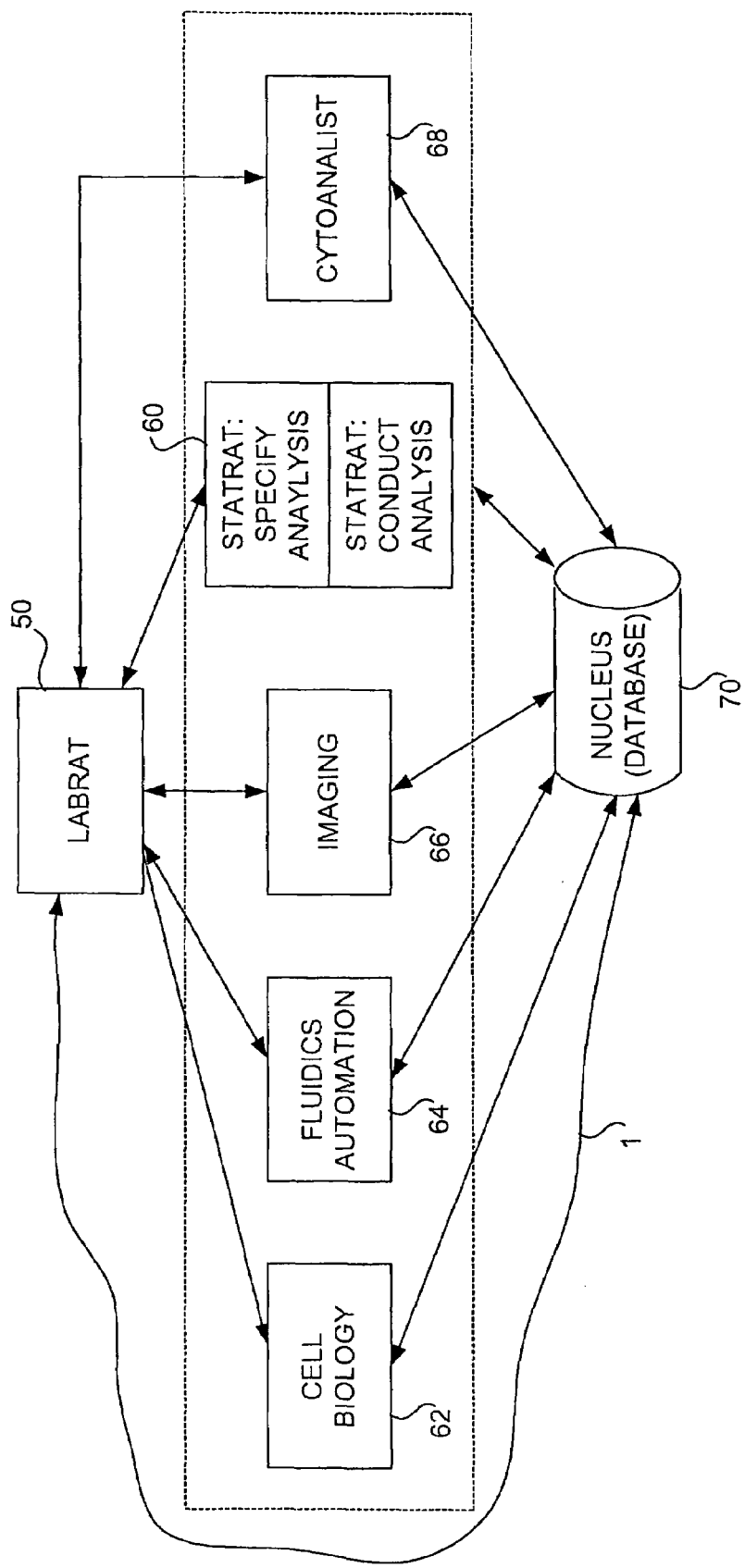
FIG. 1A is a conceptual overview of a logical system architecture in accordance with one embodiment of the present invention.

Having reference now to FIG. 1A, a conceptual overview of one specific embodiment of the present invention is presented. The system, 1, comprises two main modules, an automated laboratory experiment manager, 50, sometimes herein referred to as "LabRat" and an automated data analysis manager, 60, sometimes herein referred to as "StatRat". These major subsystems or modules interact with other systems, modules, and processes, generally discussed hereafter, to form the present invention.

The automated laboratory experiment manager generally interfaces with a cellular biology module 62, a fluidics automation module 64, an imaging process or program 66, automated data analysis manager 60, and Cytoanalyst 68 (a user interface subsystem that reports and displaying scientific results) to define, conduct, and oversee the experiment.

An experiment can be said to encompass a number of processes. Some of these processes are simple one-step procedures. Other processes are complex and may require many tasks or even many other processes to complete. The present invention implements a novel methodology for modeling and conducting the several processes required to perform a biological experiment. This novel methodology includes the use of a process model, which is a reusable system. The process model is used to define a specific process for an experiment.

Figure 1B:
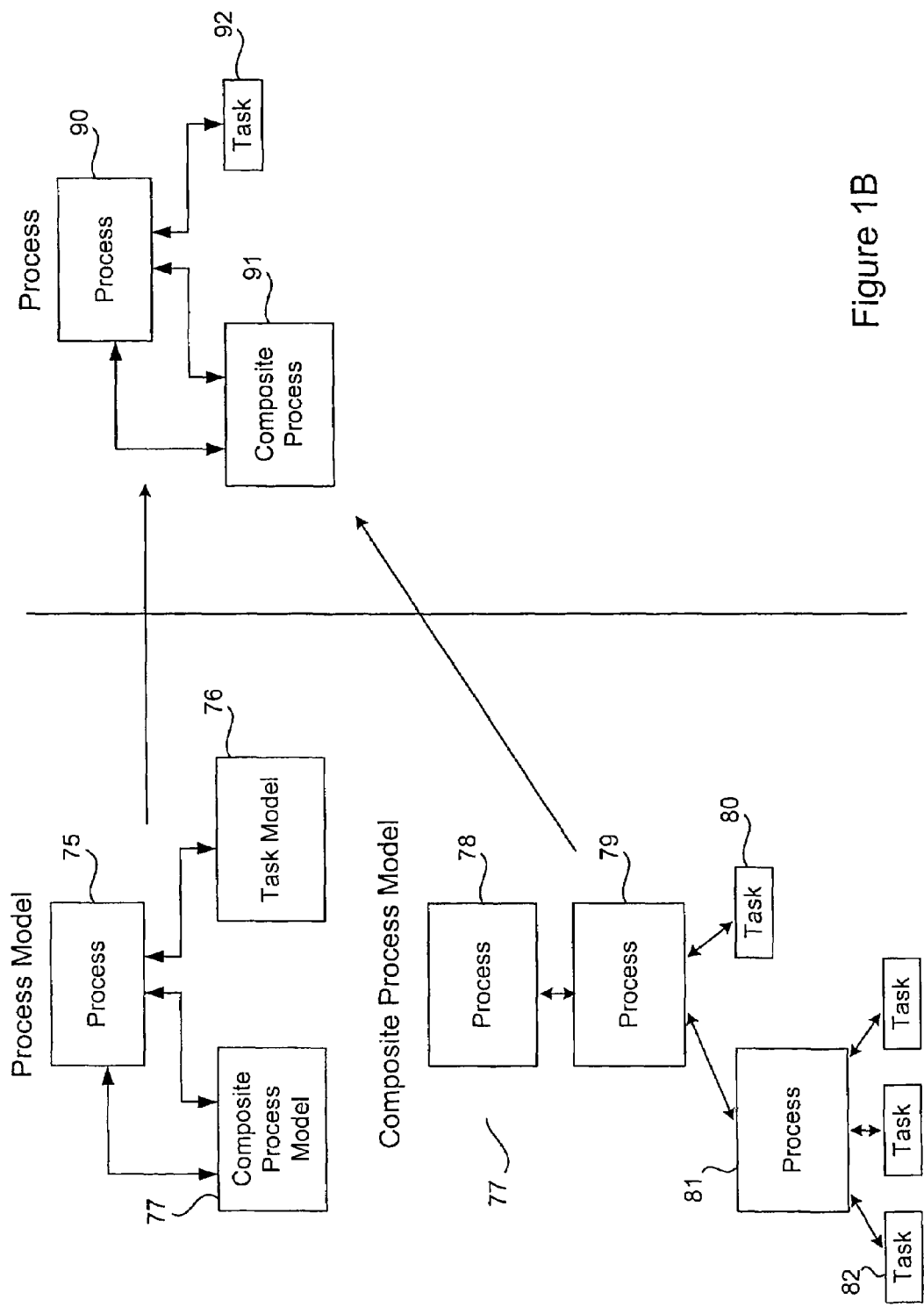
FIG. 1B depicts a sample process model and associated model of the type that may be employed with the present invention.

Having reference now to FIG. 1B, a process model 75 is shown. Process model 75 utilizes one or more task models 76 and may implement a composite process model 77. A task is generally a simple one-step procedure. A composite process is generally a multistep or multi-level procedure. An example of a composite process model 77 includes the highest level of abstraction the experiment 78, and in this example, a fluidics composite process 79 and a simple task 80. The fluidics composite process 80 comprises a further composite process, fluid addition, composite 81 incorporating a plurality of tasks 80.

Process model 75 and composite process model 77 are used to define a specific process, 90. Process 90 may be considered to be a specific instantiation of the abstract process defined in process model 75. Process model 75 defines process 90, and process 90 may incorporate one or more composite processes for instance 91 and may further incorporate one or more tasks 92. Composite process 91 is defined by composite process model 77.

As discussed, the system taught herein relates to the conduct of cellular biological experiments, especially experiments conducted to determine the effects of one or more treatment compounds on cells, particularly cells within a given cell line. The system taught by the present invention causes fluorescent microscope images (or images from other microscopy techniques such as phase contrast, confocal, epi-fluorescence and polarized light) to made of cells within assay plates, analyzes the images to detect biological markers and objects, then analyses the resulting image data to produce biological data. Higher-level statistical analyses then produce biological phenotypes and signatures for treatment compounds in the experiment from this biological data.

This process is automated by a series of feature extractor's managed by a single automated supervisor. The supervisor maintains a list of all outstanding analysis tasks. When a task becomes ready for processing, the supervisor broadcasts a message requesting such processing through a message queue. The feature extractors are individual servers that check the message queue for processing requests and undertake the tasks as they become available. This architecture distributes the image and data analysis algorithms for an experiment over multiple servers, providing a highly scalable way to manage automated data analysis. The servers retrieve and store data in the database (or local or distributed file system or archival data store), including images. According to one embodiment of the present invention, the servers retrieve and store this data by means of Enterprise Javabeans. When a task is completed, the extractor notifies the supervisor of task completion or failure, so the supervisor maintains the status for all tasks underway in an experiment.

The process monitor displays his data through a web browser for any user who wants to track progress on the data analysis.

One of the significant advantages of the present invention is the ability to distribute a number of tasks over an arbitrary number of computing devices. The tasks are specifically associated with process monitoring and image analysis. As will be explained in the discussion of FIG. 2, the logical entities primarily responsible for this functionality are a supervisor, multiple feature extractors, and an algorithm system. A process monitor may also be available to query the supervisor for information about the process state.

Figure 2:
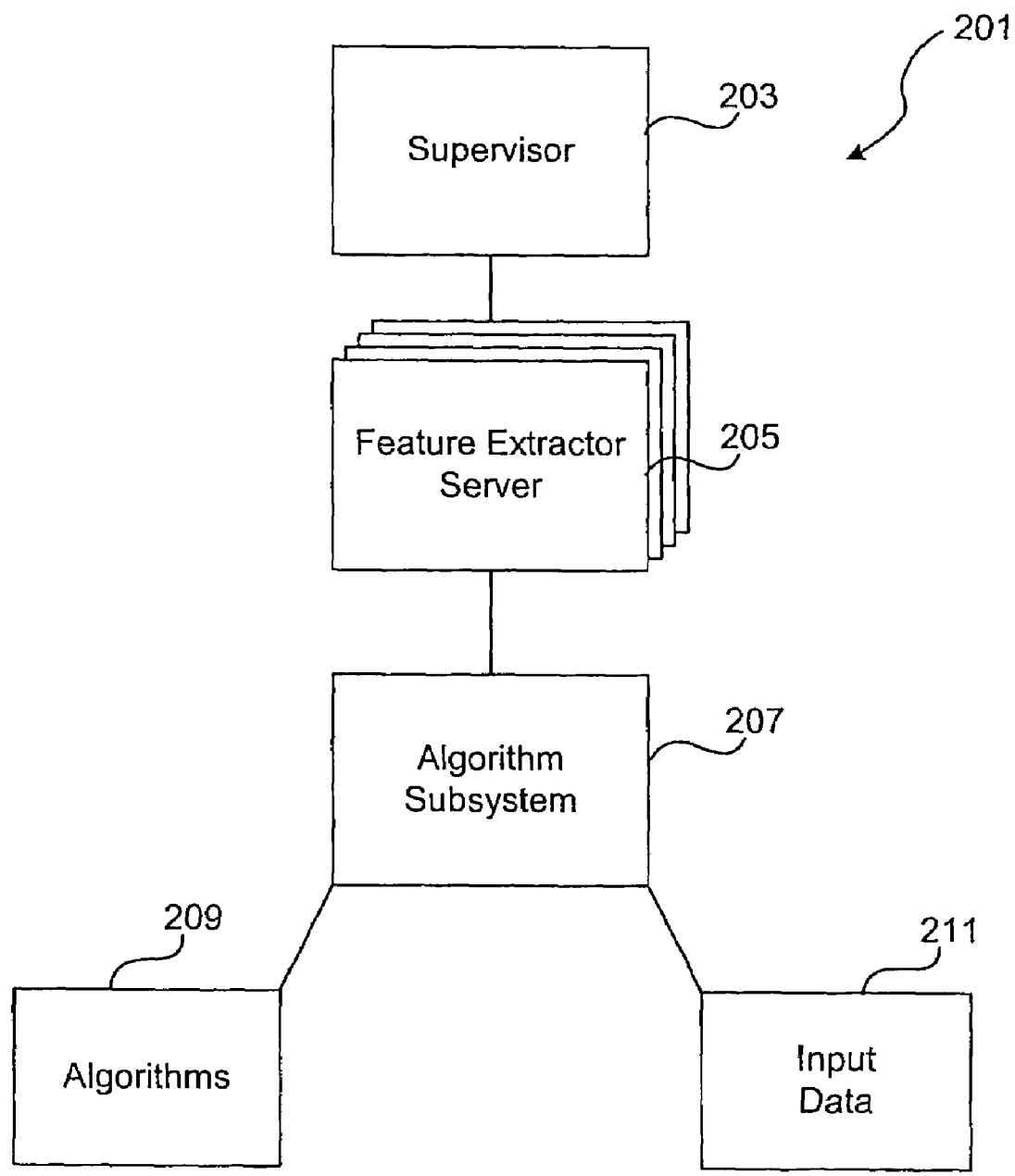
FIG. 2 is a high level logical outline of an automated image analysis manager including a supervisor, a number of feature extractor servers, and an algorithm subsystem.

As shown in FIG. 2, a high level logical outline of the automated image analysis manager 201 includes a supervisor 203, a number of feature extractor servers 205, and an algorithm subsystem 207. Subsystem 207 interfaces with a source of specific algorithms 209 and a source of specific input data (pertinent to particular ones of the algorithms) 211.

The supervisor 203 oversees allocation of analysis tasks among the various feature extractor servers 205. As feature extractors become available, the supervisor assigns them to a specific task. Upon assignment of such task, the designated feature extractor server 205 imports the algorithm subsystem 209 and starts a thread that accesses an interface to algorithms 209 in order to run the appropriate algorithm. The thread also accesses the input data as necessary to run the algorithm. The input data provided by 211 may be in various forms such as dynamic arrays or images.

Figure 3:
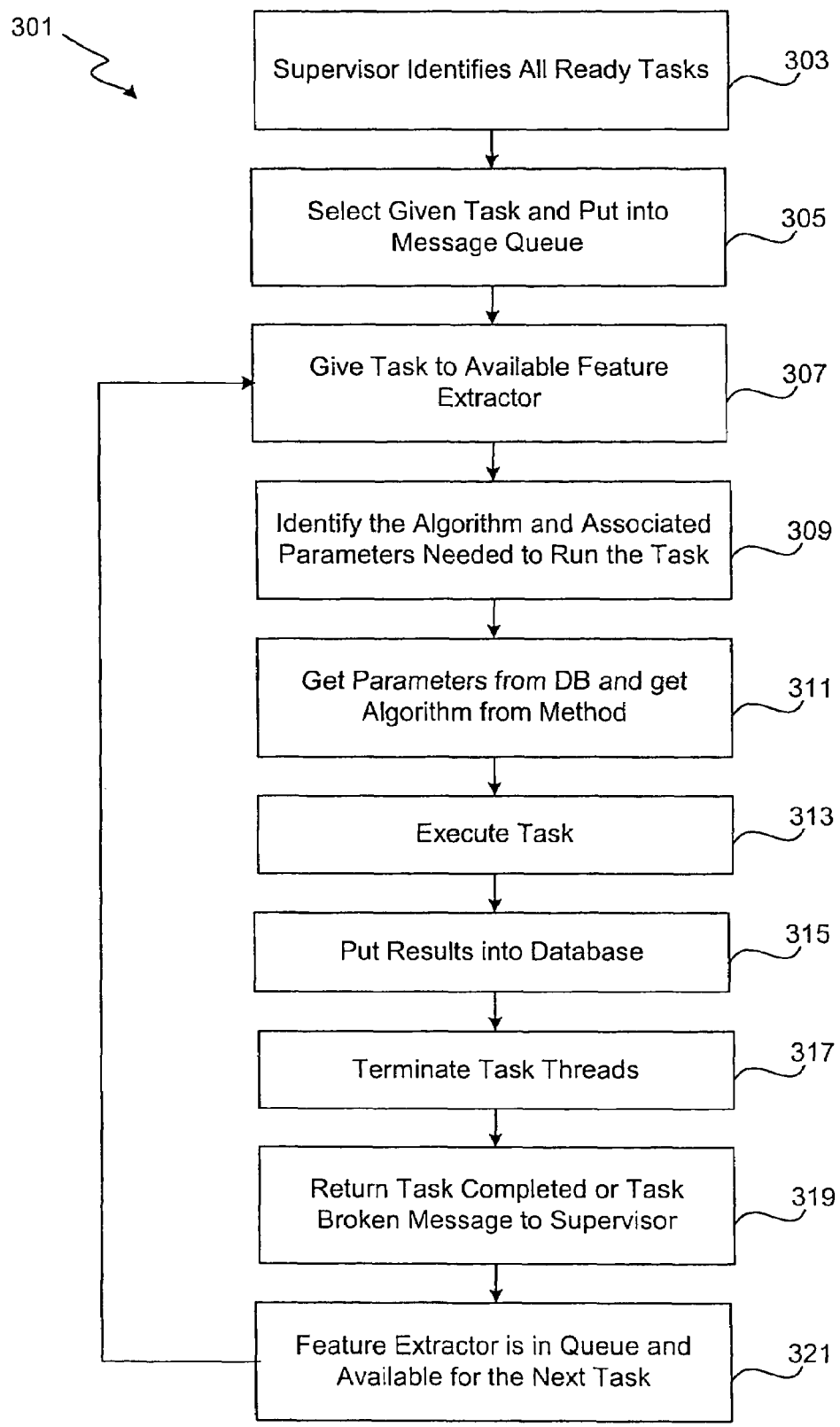
FIG. 3 is a process flow diagram illustrating the interaction between some of the entities depicted in FIG. 2.

FIG. 3 depicts a process 301 illustrating the interaction between some of the entities depicted in FIG. 2. As shown, process 301 begins at 303 with a supervisor identifying all ready tasks. Next, the supervisor selects a given task and puts it into a message queue at 305. Then, one of the available feature extractors 205 takes responsibility for the task. See 307. That feature extractor starts the appropriate thread to identify the required algorithm for the task and any associated parameters needed to complete it. See 309. The feature extractor then gets the identified algorithm via subsystem 207 and the required parameters from block 211 via subsystem 207. See 311. Typically, though not necessarily, the input data and parameters will be obtained from a database of such information.

At this point, the task is executed. That is, the selected algorithm operates on the input data to generate one or more outputs. See 313. The results of executing this task are then put in to appropriate locations in a database of interest. See 315.

Next, the task thread is terminated and the feature extractor server goes back into a queue of available feature extractors. See 317. Concurrently, at 319, the feature extractor server returns a task completed or task broken message to supervisor 203. As illustrated, the feature extractor server then looks for or becomes available for the next task assigned to it by the supervisor. See 321.

Overall Architecture—Logical

In one specific embodiment, the automated system system of this invention may be implemented via an architecture and deployment technology as described in this section. It has a number of different major systems that interact to support the various processes that support the overall service and product available to users.

Figure 4A:
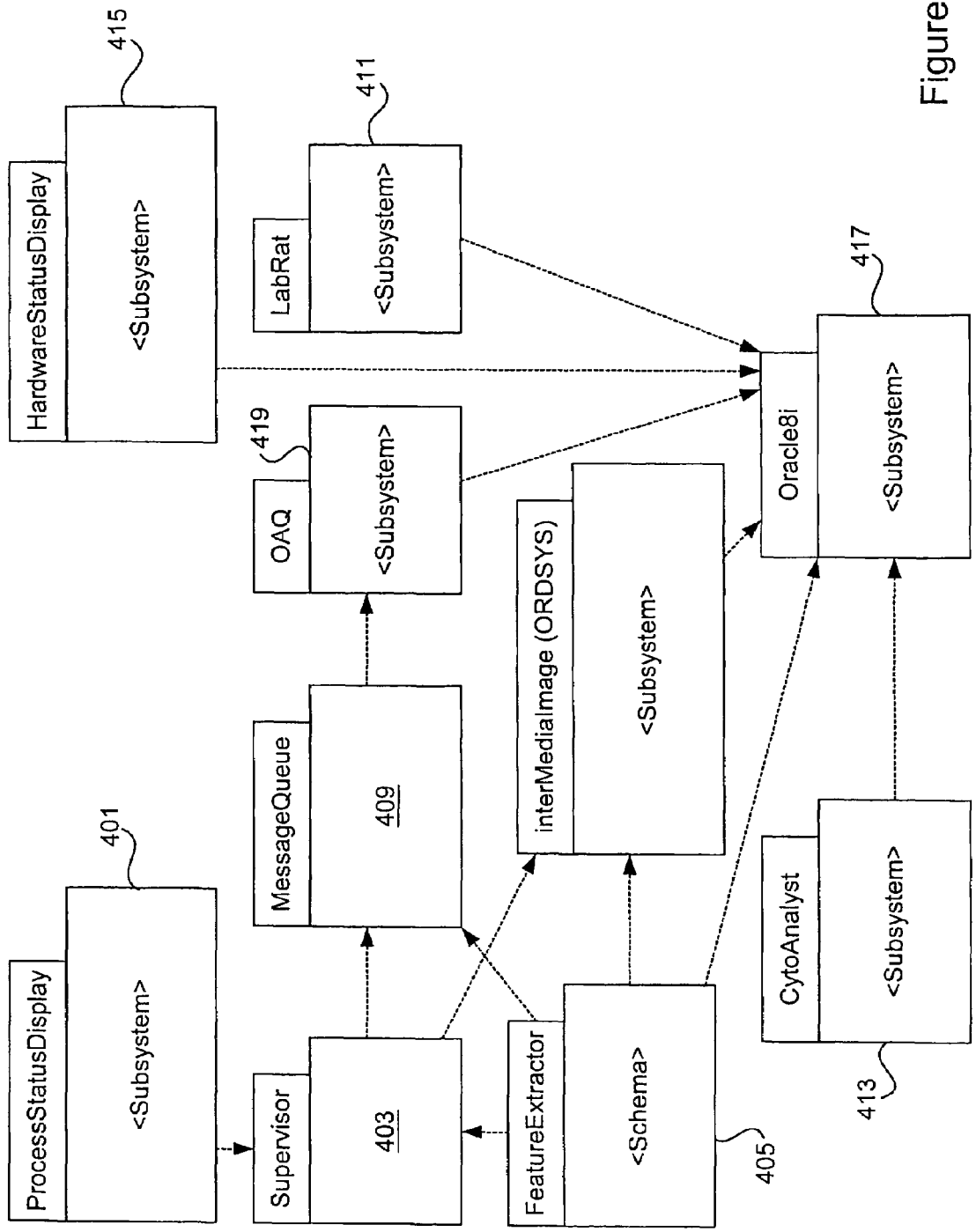
FIG. 4A presents a logical system architecture for an automated laboratory manager and image analysis system in accordance with an embodiment of this invention.

The automated system system architecture embodiment depicted in FIG. 4A has the following component subsystems.

Process Status Display (401): A user interface subsystem that displays process status for active processes, displays Feature Extractor status, and provides an interface for interacting with a subsystem known as the automated system Supervisor 403.

Supervisor (403): A server subsystem (sometimes implemented as multiple subsystems) that coordinates processes in Feature Extractors 405 through message queues and manages the storage of images through a DBMS subsystem 407 (e.g., the Oracle8i interMediaImage subsystem) that facilitates storage and retrieval of images.

Message Queue (409): A server subsystem or subsystems that provides messaging services to the Supervisor and Feature Extractor subsystems.

Feature Extractor (405): Server subsystems that automate the extraction of features from images of assay plate wells.

Automated laboratory experiment manager (LabRat) (411): A user interface subsystem that provides a comprehensive array of forms and reports on different aspects of the Cytometrix™ system, including data entry, process modeling, process tracking, failure and defect tracking, and other features of the experimental process.

CytoAnalyst (413): A user interface subsystem that provides a results reporting capability as a web-based system for displaying scientific results as HTML pages through web browsers, plus some interface technologies for providing data access to the results for further data analysis using third-party data analysis tools such as SPLUS or SAS.

Hardware Status Display (415): A user interface subsystem that displays the status of various hardware components of the automated system to enable monitoring of the system Oracle8I (417): An object-relational database management system that provides data storage and retrieval capabilities as well as application server capabilities. Other relational DBMSs may be used.

Persistent Messaging Middleware (419—also referred to as OAQ herein): Oracle Advanced Queuing, an Oracle8i subsystem that provides a persistent messaging middleware solution for Oracle8i clients. Other comparable non-Oracle middleware solutions may be employed.

InterMediaImage (409): An Oracle8i subsystem that provides storage and retrieval services for images.

Overall Architecture—Physical

Figure 4B:
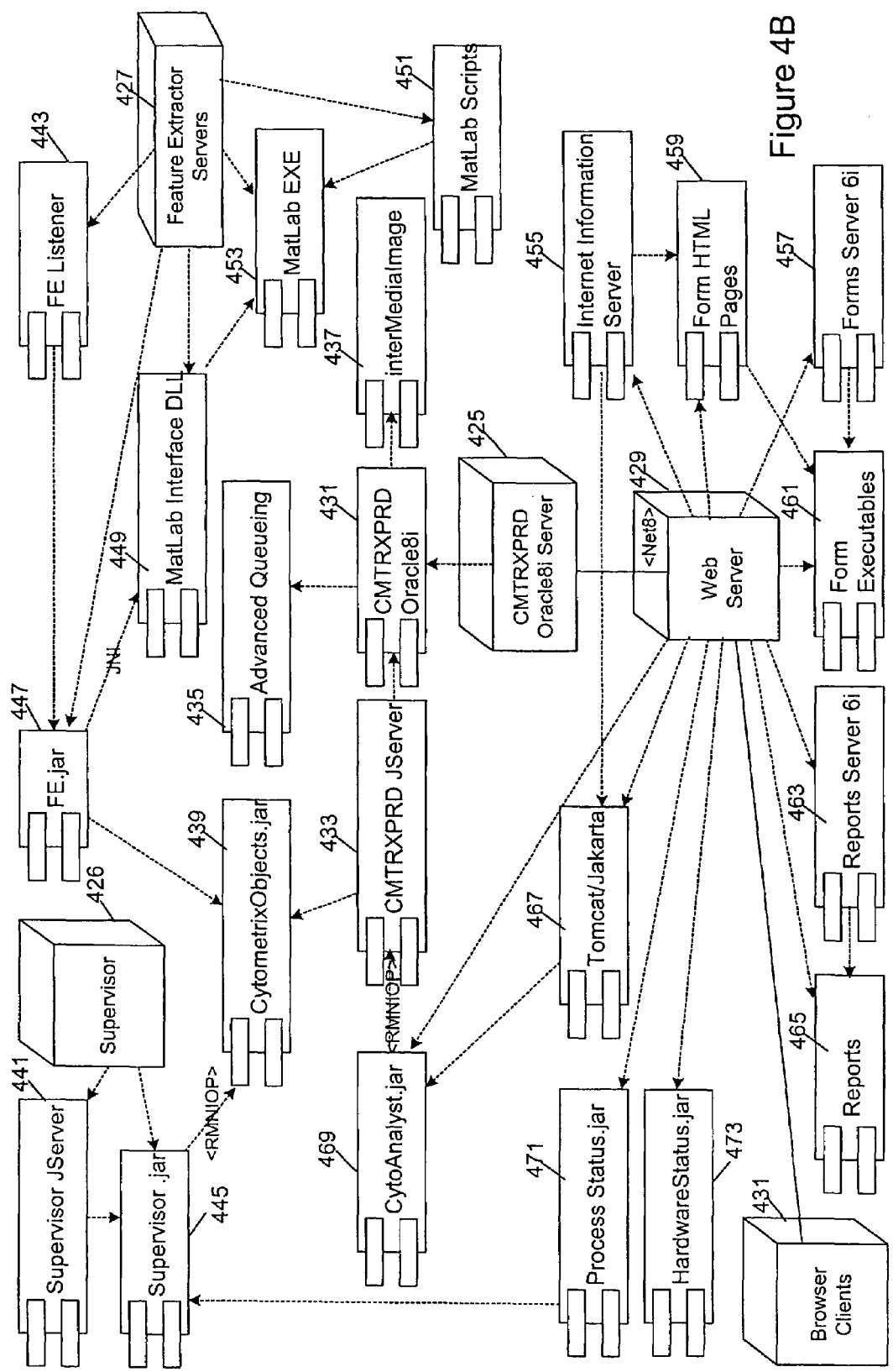
FIG. 4B depicts a specific physical architecture for implementing the automated manager depicted in FIG. 4A.

The physical system architecture of the automated system infrastructure can take many different forms. In a specific embodiment that has now been implemented, the physical architecture has the form shown in FIG. 4B. It is based on the integration of several technologies:

Oracle8i (Oracle, JServer, CORBA, interMediaImage)
Enterprise Javabeans (EJBs)
Java Server Pages
Java applets
Oracle Forms Server
Oracle Reports Server
Matlab
C++ applications and wrappers In the UML (Universal Modeling Language) deployment diagram shown in FIG. 4B, the shadowed boxes are computers (nodes) and the complex boxes are components such as jar files, exe files, HTML pages, and so on.

There are five basic nodes in the depicted system:

CMTRXPRD Oracle8i Server (425): The Oracle8i instance that holds all the system's data and stored procedures; also the server for the EJBs relating to data access ("Entity Beans"). Note again that while a specific Oracle product is depicted here, numerous other suitable DBMS products (now available or developed in the future) can be used in its place.

Supervisor (426): The server devoted to running the Supervisor entity bean. It may expand to multiple servers if required. In this example, it runs a JServer application server on an Oracle8i instance.

Feature Extractor Servers (427): Any number of individual servers dedicated to running feature-extractor algorithms at the request of the Supervisor.

Web Server (429): The server dedicated to running Forms, Reports, Java Server Pages, and serving Java applets for user interfaces.

Browser Clients (431): Any number of individual computers that run a web browser of some kind to display HTML or run Java applets.

In a specific embodiment, the system's Oracle8i instance runs on a specific server. This Oracle8i instance contains all the production data from automated system's operations. It runs a single instance 431 of Oracle8I that includes three optional subsystems: the JServer application server 433, the Advanced Queuing option 435, and the interMediaImage option 437.

The Oracle8i instance 431 was structured as a high-availability Oracle8i system with full server optimization and hot backup. The server runs continuously day-in and day-out to provide data services to all database clients.

The JServer application server on the CMTRXPRD instance runs one or more containers of entity beans, EJBs that support persistent data objects (Objects.jar 439). These beans provide data management interfaces for all the objects in the database. A Java client of this application server requests a handle to a particular persistent object from the server through an RMI/IIOP connection. The server instantiates it as required and passes the data back. These objects can be simple objects such as cell lines or task models, or complex objects representing extensive queries of the database. In particular, the queries required to run an algorithm on a Feature Extractor and to save extracted results are entity beans on the server.

The Advanced Queuing option provides a messaging middleware solution. Messaging middleware allows networked nodes to communicate with one another by passing messages with embedded objects. The Oracle8i Advanced Queuing version adds persistence to this functionality, allowing the message queue to persist even across major server outages. It is simpler to implement but does not have all the features of a remote invocation system such as CORBA or EJB, however.

The interMediaImage option provides storage and retrieval services for biological images. The image database will incorporate table partitioning, an Oracle8i feature that allows one to partition a table physically by the data in the table. In one case, the partition is by date, adding one partition each week. After creating the new week's partition, one can take the prior week's partition offline and delete the file after archiving it.

The Supervisor 426 coordinates feature extractor activities and also provides data to a process status display 471. In an implemented embodiment, the Supervisor is an NT Service.

The Supervisor communicates with the Feature Extractors through the Oracle8i Advanced Queuing message queue. This enables the Feature Extractors to poll for tasks to perform, distributing tasks in a fair way across the Feature Extractor Servers 427. As well, the Feature Extractor Servers 427 communicate their status through the message queue, sending notifications back to the Supervisor 426 when starting and finishing tasks or on demand (this is the job of an FE Listener 443).

The Supervisor accesses the Object.jar 439 entity beans through RMI/IIOP to access task and process data in the database.

The Feature Extractor Servers 443 are a group of servers, each of which performs identical functions in parallel. This allows the system to distribute image analysis functions over an arbitrary number of computers. Each server has an FE Listener 443 that polls the message queue for messages when the server becomes available for work. The Listener may be implemented as a Java application that is constantly running on the server. The Listener runs in a separate thread and continues polling after starting a task thread; this permits the Listener to (1) run multiple tasks on the single server and (2) to accept requests for status from the Supervisor and respond (for example, the Supervisor may request acknowledgement from the server to check whether it is alive).

In a specific embodiment, the listener calls a Java object in an FE.jar file 447 to run an algorithm task. The object assembles the input data by calling an EJB on the CMTRX-PRD server 425 using RMI/IIOP. It then passes the data to a MatLab interface 449 (a C++ class accessed through the Java Native Interface (JNI)) and calls a MatLab script 451 running in a MatLab server executable 453. Non-MatLab algorithms may also be employed and various embodiments have been implemented outside MatLab. The script 451 returns result data to the bean, which then calls another EJB on the CMTRXPRD server 425 using RMI/IIOP to store the result data in the database.

The Web Server 429 is a machine dedicated to running the Internet Information Server and several other software components that support most of the user interface components of the automated system. In a specific embodiment, the server includes one or more of the following:

Hardware Status Monitor 473.

Internet Information Server (455): The standard web server that comes with, for example, Microsoft Windows NT.

Forms Server 6I (457): The Oracle Forms server for displaying forms applications (LabRat/StatRat data entry and query forms); this works through a set of HTML pages 459 that run the Forms applet with a particular Forms executable (FMX) file 461, with HTML and executables both stored in web server virtual directories.

Reports Server 6I (463): The Oracle Reports server for displaying reports 465 in HTML or PDF format (failure, defect, and opportunity reports); the report executables are in another web server virtual directory.

Tomcat/Jakarta (467): The Apache implementation of Java Server Pages, the web HTML generation component that works with EJBs to create interactive HTML displays in a web browser. This is also used for presentation of analytical results in the CytoAnalyst 469.

Automated Data Analysis Manager (StatRat)

The automated data analysis manager ("StatRat") is the system component that manages the automated data analysis process. In involves the Supervisor and Feature Extractor subsystems introduced above. This process analyzes images produced by the imaging process and then extracts features from the image analysis through statistical and other kinds of algorithms. Examples of such algorithms are described in U.S. patent application Ser. No. 09/888,063 (filed Jun. 22, 2001), U.S. patent application Ser. No. 09/729,754 (filed Dec. 4, 2000), U.S. patent application Ser. No. 09/789,595 (filed Feb. 20, 2001), U.S. patent application Ser. No. 09/792,012 (filed Feb. 20, 2001), and U.S. patent application Ser. No. 09/792,013 (filed Feb. 20, 2001). Each of these documents is incorporated herein by reference for all purposes.

Some of aspects used to characterize image analysis algorithms used with this invention will now be described.

The term "component" or "component of a cell" refers to a part of a cell having some interesting property that can be employed to derive biologically relevant information using image analysis algorithms of this invention. General examples of cell components include biomolecules and cellular organelles. Specific examples of biomolecules that could serve as cell components for use with this invention include proteins, lipids, polysaccharides, proteins, etc. Sometimes, the relevant component will refer to a group of structurally or functionally related biomolecules. Alternatively, the component may represent a portion of a biomolecule such as a polysaccharide group on a protein, or a particular sequence of a nucleic acid or protein. Collections of molecules such as micells can also serve as cellular components for use with this invention. And subcellular structures such as vesicles and organelles may also serve the purpose.

The term "marker" or "labeling agent" refers to materials that specifically bind to and label cell components. These markers or labeling agents should be detectable in an image of the relevant cells. The image analysis algorithms of this invention often operate on images of markers or images highlighting the locations of markers. Typically, a labeling agent emits a signal whose intensity is related to the concentration of the cell component to which the agent binds. Preferably, the signal intensity is directly proportional to the concentration of the underlying cell component. The location of the signal source (i.e., the position of the marker) should be detectable in an image of the relevant cells.

Preferably, the chosen marker binds indiscriminately with its corresponding cellular component, regardless of location within the cell. Although in other embodiments, the chosen marker may bind to specific subsets of the component of interest (e.g., it binds only to sequences of DNA or regions of a chromosome). The marker should provide a strong contrast to other features in a given image. To this end, the marker should be luminescent, radioactive, fluorescent, etc. Various stains and compounds may serve this purpose. Examples of such compounds include fluorescently labeled antibodies to the cellular component of interest, fluorescent intercalators, and fluorescent lectins. The antibodies may be fluorescently labeled either directly or indirectly.

The term "stimulus" refers to something that may influence the biological condition of a cell. Often the term will be synonymous with "agent" or "manipulation." Stimuli may be materials, radiation (including all manner of electromagnetic and particle radiation), forces (including mechanical (e.g., gravitational), electrical, magnetic, and nuclear), fields, thermal energy, and the like. General examples of materials that may be used as stimuli include organic and inorganic chemical compounds, biological materials such as nucleic acids, carbohydrates, proteins and peptides, lipids, various infectious agents, mixtures of the foregoing, and the like. Other general examples of stimuli include non-ambient temperature, non-ambient pressure, acoustic energy, electromagnetic radiation of all frequencies, the lack of a particular material (e.g., the lack of oxygen as in ischemia), temporal factors, etc.

Specific examples of biological stimuli include exposure to hormones, growth factors, antibodies, or extracellular matrix components. Or exposure to biologics such as infective materials such as viruses that may be naturally occurring viruses or viruses engineered to express exogenous genes at various levels. Biological stimuli could also include delivery of antisense polynucleotides by means such as gene transfection. Stimuli also could include exposure of cells to conditions that promote cell fusion. Specific physical stimuli could include exposing cells to shear stress under different rates of fluid flow, exposure of cells to different temperatures, exposure of cells to vacuum or positive pressure, or exposure of cells to sonication. Another stimulus includes applying centrifugal force. Still other specific stimuli include changes in gravitational force, including sub-gravitation, application of a constant or pulsed electrical current. Still other stimuli include photobleaching, which in some embodiments may include prior addition of a substance that would specifically mark areas to be photobleached by subsequent light exposure. In addition, these types of stimuli may be varied as to time of exposure, or cells could be subjected to multiple stimuli in various combinations and orders of addition. Of course, the type of manipulation used depends upon the application.

The term "phenotype" generally refers to the total appearance of an organism or cell from an organism. In the context of this invention, cellular phenotypes and their representations in processing systems (e.g., computers) are particularly interesting. A given cell's phenotype is a function of its genetic constitution and environment. Often a particular phenotype can be correlated or associated with a particular biological condition or mechanism of action resulting from exposure to a stimulus. Generally, cells undergoing a change in biological conditions will undergo a corresponding change in phenotype. Thus, cellular phenotypic data and characterizations may be exploited to deduce mechanisms of action and other aspects of cellular responses to various stimuli.

Often an image analysis algorithm produces "quantitative phenotypes." These are multivariate phenotypic representations of the cell(s). They include various features of the cell(s) obtained by image analysis. Such features often include basic parameters obtained from images (e.g., cell shape and size, nucleus area, Golgi texture, concentration distribution of particular biomolecules within the organelle, etc.) and/or biological characterizations derived from the basic parameters (e.g., cell cycle state, mitotic index, etc.). Other attributes include changes in a migration pattern, a growth rate, cord formation, an extracellular matrix deposition, and even cell count. The multiple cellular attributes or features of the quantitative phenotype can be collectively stored and/or indexed, numerically or otherwise. The attributes are typically quantified in the context of specific cellular components or markers.

Sometimes, the quantitative phenotypes are represented by stimulus response curves that show a change in the quantitative phenotype in response to stimulus. One or more algorithms used with this invention provide this function. The quantitative phenotypes may themselves serve as individual points on response curves. A phenotypic response to stimulus may be characterized by exposing various cell lines to a stimulus of interest at various levels (e.g., doses of radiation or concentrations of a compound). In each level within this range, the phenotypic descriptors of interest are measured to generate quantitative phenotypes associated with levels of stimulus. Such curves may be compared (by algorithms used with this invention) to allow classification of stimuli and identify subtle differences in related stimuli. To facilitate the comparison, it may be desirable to present the response curves in a principal component space.

The automated data analysis manager is arranged to provide a stable, automated analysis process that provides timely, accurate analytical data on experiments for presentation and further data analysis. It enables the application of image and data summary analysis algorithms to input images, execute the analysis transactions and save all the results of those transactions to a database (e.g., an Oracle database). Each server processes a transaction comprising a minimal set of operations in the overall analysis sequence, optimizing parallel processing where possible to improve performance throughput.

In operation, the automated data analysis manager first determines whether there are input images to the system. If necessary, it preprocesses the images into an appropriate format and location, then notifies a data analysis server group that image analysis can start. Each analysis transaction results in a "results data set" in the database. Transaction data dependencies can result in input data from prior transactions read from the database as input to a new transaction.

Figure 5:
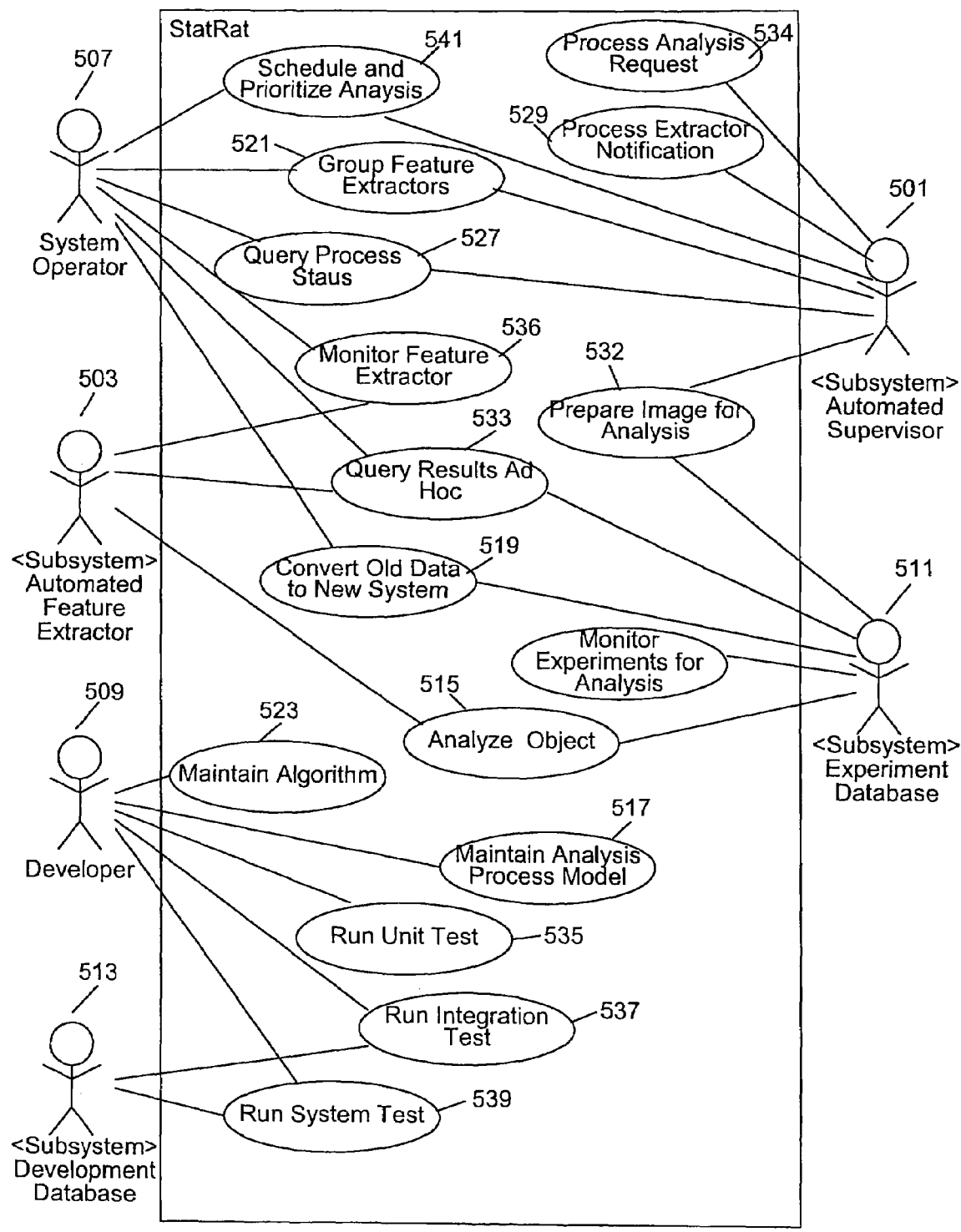
FIG. 5 is a context diagram illustrating various youth cases associated with an automated image analysis manger of this invention.

The StatRat system actors are both human and automated. They are illustrated in a use cases figure, FIG. 5. Automated Supervisor (501) is the software system that uses the automated data analysis manager (StatRat) to initiate and control analysis jobs. Automated Feature Extractor (503) is the software system that accepts assigned jobs and executes a transaction. An Automated Image Loader is the software system that monitors image analysis processes, moves files to a standard location, and updates the status of those processes when they are complete. System Operator (507) is the person who starts and monitors the status of the automated supervisor and automated feature extractors. Developer (509) is the person who develops and tests feature-extraction algorithms. Experimental Database (511) is the production (or development production) database containing experimental data and extracted features. Development Database (513) is the database containing the experimental test bed against which developers run integration and system tests.

The automated data analysis manager contains a range of use cases distributed among the various actors.

An analysis object is one of several kinds of process elements that a data analysis process may treat as the thing to process. Examples of process elements that may be handled include the following: an experiment, an assay plate, a well group, a treatment, a treatment well, a well image, and a cell. The Analyze Object use case begins with a request to a group of Automated Feature Extractors to begin processing the object. Any Extractor that is a member of the group may receive the message and process the request. If there are any process or data dependencies for a process, the process model that generated the process should include other processes that structurally represent those dependencies. Marking composite processes as sequential ensures that the dependent process does not proceed until the other processes are complete.

A Maintain Process Model use case 517 discussed below provides details on the analysis process object and how it works to describe a sequence of algorithms and dependencies between them.

A sequence of the Analyze Object use case for executing an algorithm is depicted in the interaction Table 1.

TABLE 1

| Actor | System |
|---|---|
| Read an analyze message to a current Extractor group from the message queue. | Extract the algorithm task and analysis object from the message. |
| Gather data inputs and parameters. | Query task inputs and parameter arguments as required by the algorithm. |
| Run the algorithm, passing in inputs and parameters. | Run the algorithm. |
| Save the analysis results to the Experimental Database. | Save the features and commit. |
| Send a finished-task message to the Supervisor to report that the analysis task is complete. | End the use case. |

Various extensions on the Analyze Object use case interaction may be implemented. Some of them follow.

Extension 1: If the algorithm task fails to execute and raises an exception, log the error message to the Experimental Database, identifying the Extractor and the algorithm program that failed. Notify the Supervisor with a cannot-process-request message for the task, including the Extractor and program names with the error message. The Supervisor will set the task status to Broken.

Extension 2: Image Analysis performs all the tasks relating to production of MatLab MAT files from images (image input, MAT file output, no database output) for a given plate. The algorithm looks in the database for images to analyze and reads the images from their standard location on disk.

Extension 3: Montage Production produces a montage of well images for a given plate (image input, image output, no database output). The algorithm looks in the database for images to analyze and reads the images from their standard location on disk.

Extension 4: Summary Analysis performs statistical analysis on DNA and Golgi markers for a given plate, producing summary data in the database (MAT file input, database output to Features table) for that plate. The algorithm looks for MAT files for input; there is no input from the database of any kind. The algorithm produces features in the database, saving them to a single Features table.

A Convert Old Data to New System use case 519 converts data from the previous version(s) of the system database to the current version. This may involve some gaps in information, as the current schema sometimes expands the amount of information about many or all aspects of the system.

Automated Feature Extractor 503 is an image analysis system actor that runs an algorithm as part of an analysis process. In a specific implementation, the Automated Supervisor sends messages through a message queue to Feature Extractor actors to perform analysis tasks (pieces of an analysis process). The scalability of this system depends on having the ability to assign tasks to available Feature Extractors. Feature Extractors should be able to maintain individual servers without disrupting overall system processing. Also, they should be able to allocate certain servers by date and time or to allocate servers to special projects. All of these requirements are satisfied by the concept of Feature Extractor groups, collections of Feature Extractor servers that share status. An Extractor may belong to more than one group at any given time. The Supervisor then gets requests including the group identifier to assign analysis processes to a specific group of Extractors.

In a Group Feature Extractors use case 521, the System Operator creates, modifies, or removes a group of Feature Extractors in the Experimental Database through the Automated Supervisor. The use case also is the place where one can add, modify, or remove Feature Extractor objects in the Experimental Database 511.

Suitable processes of the Group Feature Extractors use case are depicted in Table 2 below.

TABLE 2

| Actor | System |
|---|---|
| Add a new group of Feature Extractors, supplying a list of existing and/or new servers as well as a group name and description. | Insert any new servers (name, description) into the Experimental Database. Update any modified server names or descriptions in the database. Insert the new Feature Extractor Group name and description into the database. Add the new servers to the new group. Remove the existing servers from their current group (if any) and add them to the new group. Commit the changes. |
| Modify a group by modifying the name or description or by adding or removing servers. | Modify the name or description of the group in the Experimental Database. Insert any new servers (name and description) into the database, then add them to the modified group. Remove any existing servers from their current group and add them to the modified group. Remove any servers marked for removal from the modified group (they then have no group). Commit the changes. |
| Move a server from one group to another. | Remove the server from its current group and add it to the target group. Commit the changes. |
| Remove a server from a group. | Remove the server from its current group. Commit the changes. |
| Remove a server from the system. | Remove the server from its current group and from the set of Feature Extractors in the system. Commit the changes. |
| Remove a group from the system. | Remove any servers from the group. Remove the group from the system. Commit the changes. |
| Create a time slot for the feature extractor group. | Save the start and end times for the group to the database. Commit the changes. |
| Query time slots for the current feature extractor group. | Query the group time slots and display the start and end time (and other data depending on the kind of time slot). |
| Remove a time slot from the current set of slots for the current feature extractor group. | Remove the time slot from the group. Commit the changes. |

An algorithm is an independent system that accepts inputs, processes the inputs, and produces results. Generally, the StatRat (the automated data analysis manager system) is able to provide a platform for executing algorithms and storing their results in a database. Another part of this mission is to enable developers to maintain their algorithms within the automated data analysis manager.

Developers can make available several versions of an algorithm. In a preferred embodiment, the system can employ versioning to add the version to a list of supported algorithms rather than actually replacing an algorithm. Parameter lists typically belong to the version, not to the algorithm.

Maintaining an algorithm (use case 523) may have various aspects such as the following: adding a new algorithm to the automated data analysis manager; removing an existing algorithm version from the automated data analysis manager; versioning an algorithm; changing an algorithm's name, purpose, or parameter set. The parameter list typically includes input parameters. Input parameters are those that the driver for the algorithm collects together and passes to the algorithm. Output parameters are those that the algorithm returns; see the Analyze Object use case for result storage.

Regarding the Prepare Image for Analysis use case 532, an Image Loader monitors the status of imaging tasks within an experiment to find any that require file movement services or that require status updating. Ultimately, the Image Loader marks an imaging task Complete, which informs the Supervisor 501 that analysis tasks can now begin.

An imaging task is a task generated from a specific Task Model object in the automated system database (a preallocated process model ID). The Image Loader uses this ID to find imaging tasks. Some processes of the use case are depicted in Table 3.

TABLE 3

| Actor | System |
|---|---|
| Query the wells on plates that are process elements for imaging tasks with status Started or Restarted where the wells have no associated well image files registered in the database. | Return a result set of wells. |
| For each well, check whether the microscope has produced one or more required image files. | Return files. |
| For each file, copy the file to its standard location and update the database with the file, | Copy the file and update the database with the file and its location (WellImage table). Commit the transaction. |
| On completing the last well for a plate, update the status of the corresponding task to Completed. | Updated the task status to Completed. |
| End the use case. | Complete the transaction. |

The Automated Supervisor 501 can monitor the Feature Extractors to enable status reporting to the System Operator 507 and to facilitate control of analysis processes. A Monitor Feature Extractor use case 525 enables the Query Process Status use case 527, which displays status information to the System Operator 507.

In one implementation, there are three situations in which the Supervisor requests status from the Extractor. (1) After an Extractor sends a message that it has started a task and a designated time passes without a message completing the task, the Supervisor requests an acknowledgement from the Extractor that it is still alive. (2) After a designated time passes with no messages at all from an Extractor in the active extractor groups, the Supervisor requests an acknowledgment. (3) At the request of the System Operator, the Supervisor immediately requests an acknowledgment from a group (or all groups) of Feature Extractors.

In this embodiment, if no acknowledgment is forthcoming, the Supervisor marks the Feature Extractor(s) as dead. If the Extractor responds with the name of the current task, the Supervisor marks the Extractor as busy. If the Extractor responds with a ready message, the Supervisor marks the Extractor as Ready.

This Supervisor and Extractor can be designed so that changing the status of the Feature Extractor does nothing whatever to change the control flow of the system. It is purely for the status display through the Process Monitor. For example, if one sees a dead Extractor and go and reboot it, the Extractor will eventually pick up the message requesting acknowledgment and respond, changing the status back to ready.

When the Supervisor receives a "starting-process" or "finished-process" message from the Extractor, it marks the Extractor as busy or ready, respectively.

Table 4 below shows some processes of this use case.

TABLE 4

| Actor | System |
|---|---|
| Request status from one or more Feature Extractors if any of the situations 1–3 is true. | Enqueue a message to the Extractors requesting status. |
| Receive a message from the message queue addressed to Supervisor. | Receive the message. |
| End the use case. | Commit the transaction. |

Regarding the Process Analysis Request use case 534, to initiate a process, the Automated Supervisor 501 queries all active processes from the database and determines which Algorithm Tasks are ready to run. The Automated Supervisor then sends messages to Automated Feature Extractors run the task, sending the task ID as the body of the message.

In a Process Extractor Notification use case 529, the Automated Supervisor 501 receives a message from an Automated Feature Extractor through the message queue notifying the Supervisor of the starting or completion of an assigned task by an Extractor. The Automated Supervisor then updates the process status in the status list and the database and (for a finished-task message) and updates the status of any processes waiting on the completion of the first process.

Note that this use case shares some processes with a Monitor Feature Extractor use case 531, which handles special acknowledgment notification in addition to standard starting-task and finished-task messages.

The System Operator 507 may need to know the status of the analysis processes for all active processes as well as the current status of all Automated Feature Extractors and the Automated Supervisor 501. The Query Process Status use case 527 presents this information to the System Operator 507 through the Process Monitor in this example.

Table 5 below shows some processes of this use case.

TABLE 5

| Actor | System |
|---|---|
| Query active processes from the database. | Display a list of active processes, listing all active tasks and their Feature Extractors and a list of all queued tasks waiting for a free Extractor. Display a list of Feature Extractors with status (ready, busy, dead). Display a list of process requests waiting for processing (not yet sent to the message queue as tasks). |
| Update the status of a Waiting task to Ready, subject to process status requirements. | Update the task status. |
| Update the status of a Broken task to Ready, subject to process status requirements. | Update the task status. |
| Update the status of a Started task to Broken. | Update the task status. |

After completing automated analysis, the Operator 507 may want to look at the data to investigate results. A Query Results Ad Hoc use case 533 lets the Operator get information from the Experimental Database based on queries in a standard query language. Preferably, the database should be available from the standard analytical tools used to post-process the results so that the Operator can perform exploratory data analysis on the data.

This need may be satisfied through a combination of the SQLPLUS query tool from Oracle (or comparable tool) and the ODBC interface for getting data into standard tools.

A unit test (use case 535) tests a program unit (module, class, function, or whatever) in isolation. The objective of a unit test is to make the unit fail until achieving some coverage criterion such as branch coverage (all paths through the test model executed at least once) without failure. Test models are usually white-box models that model the actual code structure, such as control-flow diagrams or data-flow diagrams, and coverage usually means testing all paths through such diagrams.

The automated data analysis manager has as part of its mission assisting developers in testing their algorithms. The system therefore provides use cases for the common types of test and features that enable such testing. For a unit test, the automated data analysis manager provides a way to run an algorithm in isolation from both the database and the rest of the system, preferably in the developer's environment away from the running production or development system running as a whole. The automated data analysis manager runs the test suite (a collection of test cases) and puts the results into the Development Database.

Note that there are many different test framework architectures that can be used to provide the test system. Ideally, developers would be able to build their own test suites and result saving code. Other possibilities exist, however, including automatic test suite generation and custom test script development services by a dedicated test group.

An integration test (use case 537) tests a subsystem working as an integrated whole. The objective of an integration test is to make the system fail by combining the subsystem elements, focusing on relationships between elements (including use of the database), until achieving some coverage criterion such as branch coverage. Missing parameters, invalid data passed to another function, and violated database constraints are all examples of such errors. Test models are usually black-box models that model the function of the subsystem, such as a state-transition diagram, but also calling-tree graphs showing what elements use what other elements and what assumptions are made for each relationship.

For an integration test, the automated data analysis manager provides a way to run an algorithm or an analysis process as a complete process isolated from other subsystems. That is, you should be able to execute an algorithm test suite with full input and output processing from the database and assuming appropriate data exists as it would in the real system. The Run Integration Test use case thus executes test suites comprising a set of transactional use cases such as Analyze Well or Analyze Experiment with the designated algorithm or package as the result. The use case encapsulates any results that move outside the subsystem under test, however, such as messages queued to start other processes and so on.

Exemplary processes of this use case are depicted in Table 6.

TABLE 6

| Actor | System |
| --- | --- |
| Start an integration test suite. | Run the test suite, supplying any required data for the test environment and trapping any outputs to other subsystems. Store the test results in the Development Database. |
| Query the test results. | Display the test results. |

A system test (use case 539) is the combination of an integration test for the automated data analysis manager as a whole plus a series of test suites designed to test system capabilities. The objective of the system test is to make the system fail by exposing it to situations likely to make it fail (crashing a server, running a large number of analyses at once, and so on). Test models for system testing are typically black-box tests of functionality at the level of use cases in this document. The system test may verify that all use cases in this document can execute without failure, covering the requirements for the system.

For a system test, the automated data analysis manager should be able to run in a controlled environment that allows testers to structure the test suites designed to make the system fail. Usually this entails a complete environment mirroring production but with a specially constructed database and sequence of user operations, often run as automated system test scripts.

Preferably, there are two kinds of analysis scheduling (use case 541) in the automated data analysis manager. The Experiment Database 511 scans for images that are ready to process and automatically initiates processing on ready images. Alternatively, the System Operator 507 may want to restart an interrupted analysis, reprioritize analyses, or do a special analysis on an object (experiment, plate, well group, well, or well image). When this is the case, the Operator schedules the analysis by queuing it in the analysis task queue manually to start as soon as possible or at a given date and time. The Operator specifies the analysis object, an analysis process model, and an optional Feature Extractor group. If the Operator does not specify an Extractor group, the system uses the default Extractor group.

The Operator may query the scheduled analysis tasks in the queue and prioritize or remove them. Processes of the Schedule and Prioritize Analysis use case 541 are depicted in Table 7.

TABLE 7

| Actor | System |
| --- | --- |
| Set up an analysis process execution by entering the analysis object (experiment, plate, well group, or well). Optionally, specify any of the analysis process model, process parameter arguments, Feature Extractor group, priority, or the date and time to queue the process for execution. | Send a message to the Automated Supervisor to start an analysis process. The message includes the analysis object, the process model, the arguments (default to default arguments), the group (default to default group), the priority (default to group priority), and the target execution date and time. |
| Refresh the current display of scheduled analysis processes. | Request the Supervisor to send and display a list of currently queued analysis processes (object, process, parameter arguments, extractor group, priority, and queue timestamp). |
| Change any of the parts of the analysis process (object, process, parameter arguments, extractor group, priority, and queue timestamp). | Modify the task in the queue, adjusting priority position as required. Generate the relevant extractor request(s) for the modified task. |

Process Generator Design

The Process Generator subsystem is preferably a standalone subsystem that generates processes from process models.

This subsystem implements certain use cases. A Model Experimental Process use case builds process model graphs. A Maintain Experiment use case creates an experiment process from an experiment process model. A Generate Processes use case generates composite processes and tasks under the experiment process model.

The Model Experimental Process use case describes the modeling of experiments: An experimental process model is a tree hierarchy of composite processes and tasks that represent the elements of the experimental process that we want to track in terms of start and end dates.

The Composite pattern organizes trees in terms of abstract base classes, composite collection node classes, and leaf classes. Composite classes group composites and leaves, resulting in a recursive tree structure. (See for example, Gamma et al., *Design Patterns*, Addison-Wesley, 1995, and R. Muller, *Database Design for Smarties*, Morgan Kaufmann Publishers, 1999 (both incorporated herein by reference) for details of this pattern.)

The Composite Process Model orders its children Process Model objects. This ordering permits the ordered, sequential execution of algorithm tasks and represents the process (and data) dependencies of the analysis process. Each composite has a control flag that specifies sequential or parallel execution. Sequential execution tells the system to run the children in order. Parallel execution tells the system to run the children in parallel. One can thus design experiments that have both sequential tasks and tasks that may run parallel to one another. As well, one can query and reuse any process model as a child of more than one parent, which lets you reuse subprocesses in several different experiment models.

As well as specifying the parallel versus sequential execution of the tasks, the process model also specifies an iteration structure based on the relationship of the objects that are the target of the process. Experiments are collections of plates (or other experiments, composite experiments). Plates are collections of wells. Wells are imaged to produce some number of images per well, and there may be some number of cells in each well or image. This hierarchy lets the process model automatically generate tasks for the appropriate objects. For example, if you process an experiment, and one subprocess is at the plate level, the model generates one subprocess for each plate that belongs to the experiment.

In a specific embodiment, one can track process execution through the processes that the model generates and their start and end dates. One can add feedback about the processes through the Logged Comment class in the Feedback subsystem; every subclass of System can have logged comments. See the Failure Tracking System use cases below for details of logging and failure tracking for processes and other reusable systems.

Figure 6A:
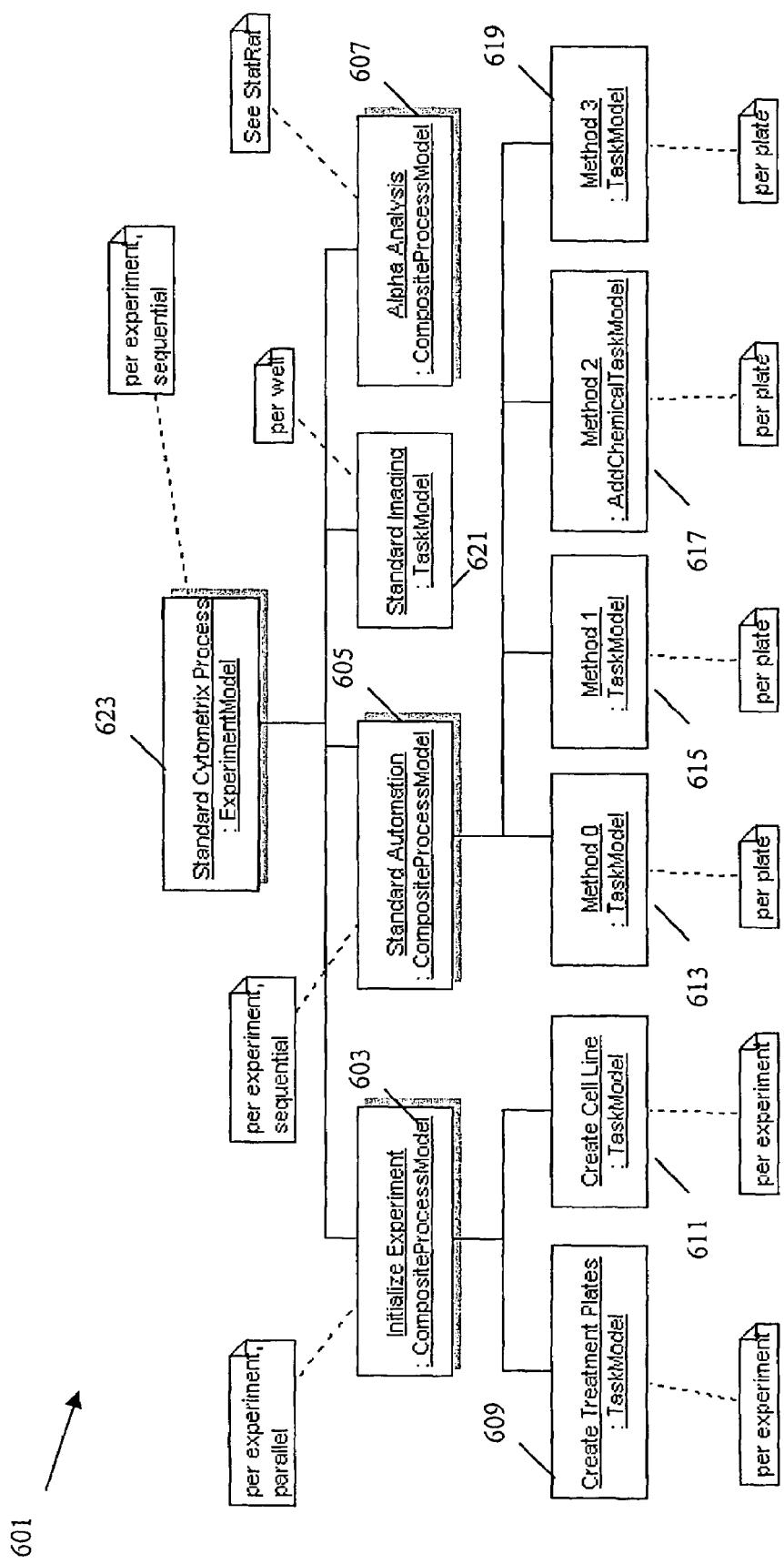
FIG. 6A presents a sample laboratory experiment process model.

FIG. 6A illustrates the processing logic associated with a sample laboratory experiment process model. A tree 601 possesses 3 composite process models (603, 605, and 607) and 7 task models (609, 611, 613, 615, 617, 619, and 621, excluding the Alpha Analysis Model structure).

A typical Process experiment model 623 runs four subprocesses. (1) Initializing the experiment 603 by creating the cell lines 611 for the experiment (a task model here, per experiment) and, in parallel, by creating the daughter treatment plates 609 for the experiment (a task model here, per experiment). (2) The standard automation process 605 for all plates in the experiment, a composite process model for the experiment with four task models underneath it that run sequentially, one for each plate in an experiment. (3) The standard imaging process 621 (per well) for all plates in the experiment is a task model here. (4) The Alpha Analysis Model 607 is provided as one for each experiment.

Figure 6B:
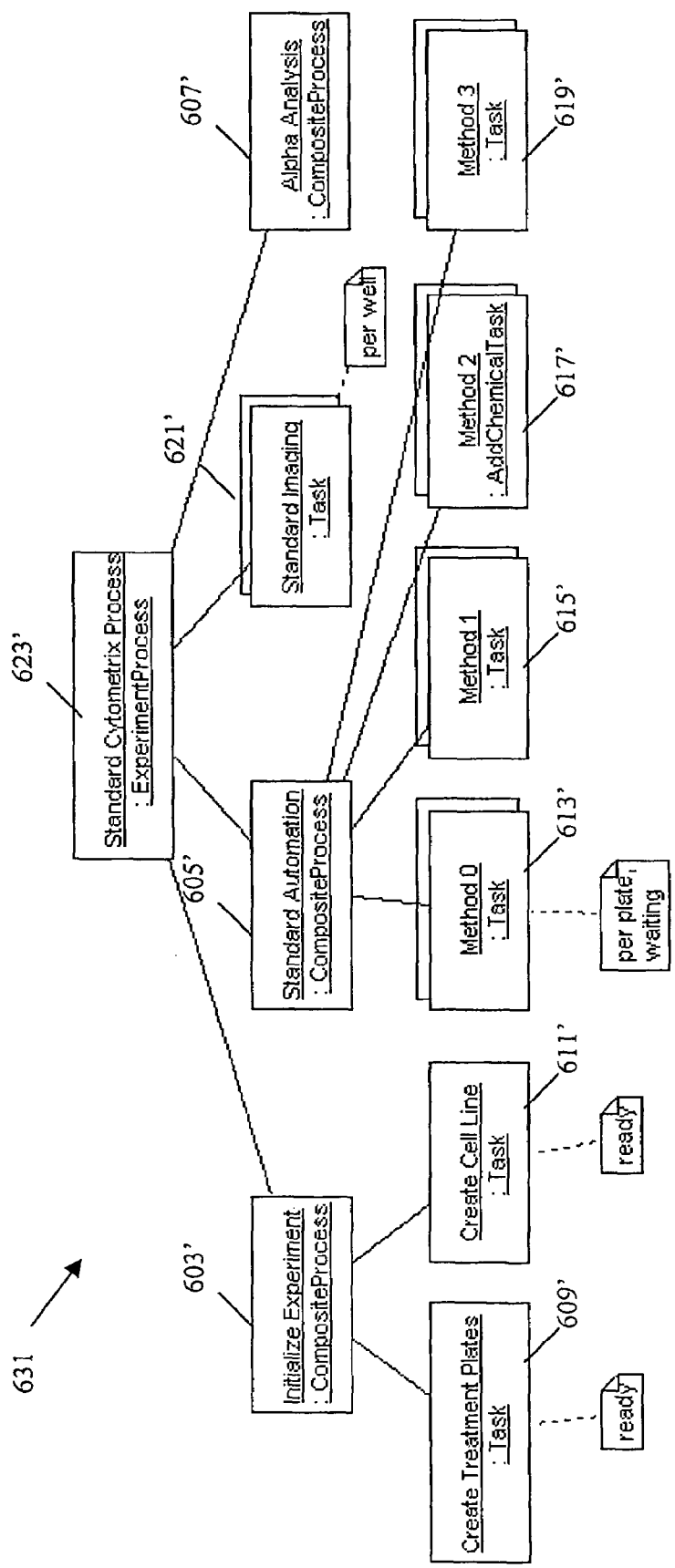
FIG. 6B presents a process tree generated from the process model of FIG. 6A.

When the database creates a process tree from this structure, it sets the status as appropriate. For example, a tree 631 in FIG. 6B represents the process tree generated from the above model:

The composite process models generate composite processes, and the task models generate tasks. The Experiment Composite Model generates an Experiment Process. The Add Chemical Task Model 617' generates an Add Chemical Task. Where a model is at a different level from the process element, the model generates multiple processes or tasks at the appropriate object level. For example, the process element is an experiment, but the Standard Imaging task model 621' is at the well level, so the model generates one imaging task per well in the experiment. Similarly, as the Method 0 task model 613' is at the plate level, the model generates one Method 0 per plate.

The Initialize Experiment process model 603' is marked as parallel. Therefore, both of the children tasks become ready to run. Since the Standard Process model 623' is sequential, however, the children of the Standard Automation process 605' are waiting, not ready. The experiment initialization should complete before any standard automation can begin. One implication of this model is that all the plates need to go through Method 0 before any of them can start Method 1.

When a model has a level lower than the one above it, it means the Process Generator must create multiple processes for the single model node. No child model of that model may have a level higher than the one for that model. That is, as one goes down the tree, if one moves to finer levels of granularity, one has to stay at that level of granularity. Also, if a model generates multiple processes, its children generate at least one process linked to each of those processes. This situation reflects a desire to limit sequential processing to the process element rather than to the entire process step. For example, if Standard Automation in the above example were at the plate level instead of the experiment level, there would be one Standard Automation composite process for each plate and one each of the four subprocesses for each plate. When these processes run, the composite process for each plate completes in parallel with that for all the other plates, and one needs only complete each process for the single plate to move on to the next one in sequence for that plate. The example above forces all plates to go through Method 0 before any plate can go through Method 1 because the composite process is at the experiment level rather than at the plate level.

Preferably, process generation works on an as-required basis (just-in-time process generation). Process generation generates only those processes next in order in processing sequence. Process generation takes into account the model element level and the process element type for the process (an experiment, usually) by generating the correct number of processes for the process element (all the wells on all the plates in the experiment, for example). It also generates all processes under a composite process marked as parallel. Sequential composite processes generate their children one at a time in sequence as the processes end. As each Process is generated the attribute childSequence is set as obtained from the parent Process as an incremented index.

In one implementation, the Process Generator architecture rests on top of an array of persistent schema subsystems. The Process Generator itself is preferably a stored program unit (a package) residing in the database. The Oracle8i job queue runs the process generator periodically (e.g., once every fifteen minutes) to ensure the rapid generation of processes from models and experiment designs.

Process Monitor Subsystem

A process monitor subsystem provides a graphic user interface (GUI) to display status of the algorithm analysis processes, and to enable the users to modify the process's status as well.

In one embodiment, the look of the GUI is designed similar to that of the Window Explorer. The hierarchy relationship of process data is displayed in a tree control at the left side, and the detailed information for the process data are shown in a tabular format at the right side. There are several buttons on the GUI to let users send commands, and a context sensitive popup menu for the same purpose as well.

In this embodiment, the process monitor may be a standalone Java application. It supports multi-user environment. The user is able to send a command to fetch and view all the related processes data, and to send another command to commit the modifications he/she has made for the processes data. Data concurrency and consistency are handled at application level. In another embodiment, the process monitor runs in a standard web browser, and the applet may interact with servlets running on the web server to access database for status display or modification. Preferably, the Process Monitor subsystem contains all the code required to view and modify the analysis process data.

Supervisor

The Supervisor subsystem is an automatic process execution control system for the experiment process. The Supervisor sends task requests to different task executors implemented for the experiment process. The execution path begins with a predetermined top-level composite process, runs each of its child processes or tasks either in ordered sequential or in parallel depending on the rules specified for the parent process.

In one embodiment, the supervisor is able to support two kinds of task executions. The first is an algorithm task proxy executor that runs algorithm tasks through the message queue subsystem. The second is an image loader that loads well image files generated by the imaging station to the database. The first is implanted inside the supervisor as an internal package, and the second is imported as an external package.

For the algorithm task proxy executor, its main functionality is sending algorithm task requests to feature extractor servers through the message queue and taking care of message notifications from feature extractor servers. Depending on the returned status and execution history for a particular algorithm task, the supervisor can either change the status of the algorithm task and update its corresponding entries in database, or it can re-send the algorithm task under certain circumstances. There may also be a housekeeping routine running in the algorithm task proxy executor that periodically checks the status of started algorithm tasks to ensure that all the tasks are still running on their associated feature extractor servers, or it may re-send the task if the feature extractor which originally started the task is not responsive.

For the image loader, the supervisor simply invokes the image loader to carry out an image-loading task as it encounters an imaging task along its process execution path. Preferably, the Supervisor subsystem contains all the code to run the algorithm analysis tasks on a group of feature extractor servers and to initiate image-loading tasks.

Figure 7:
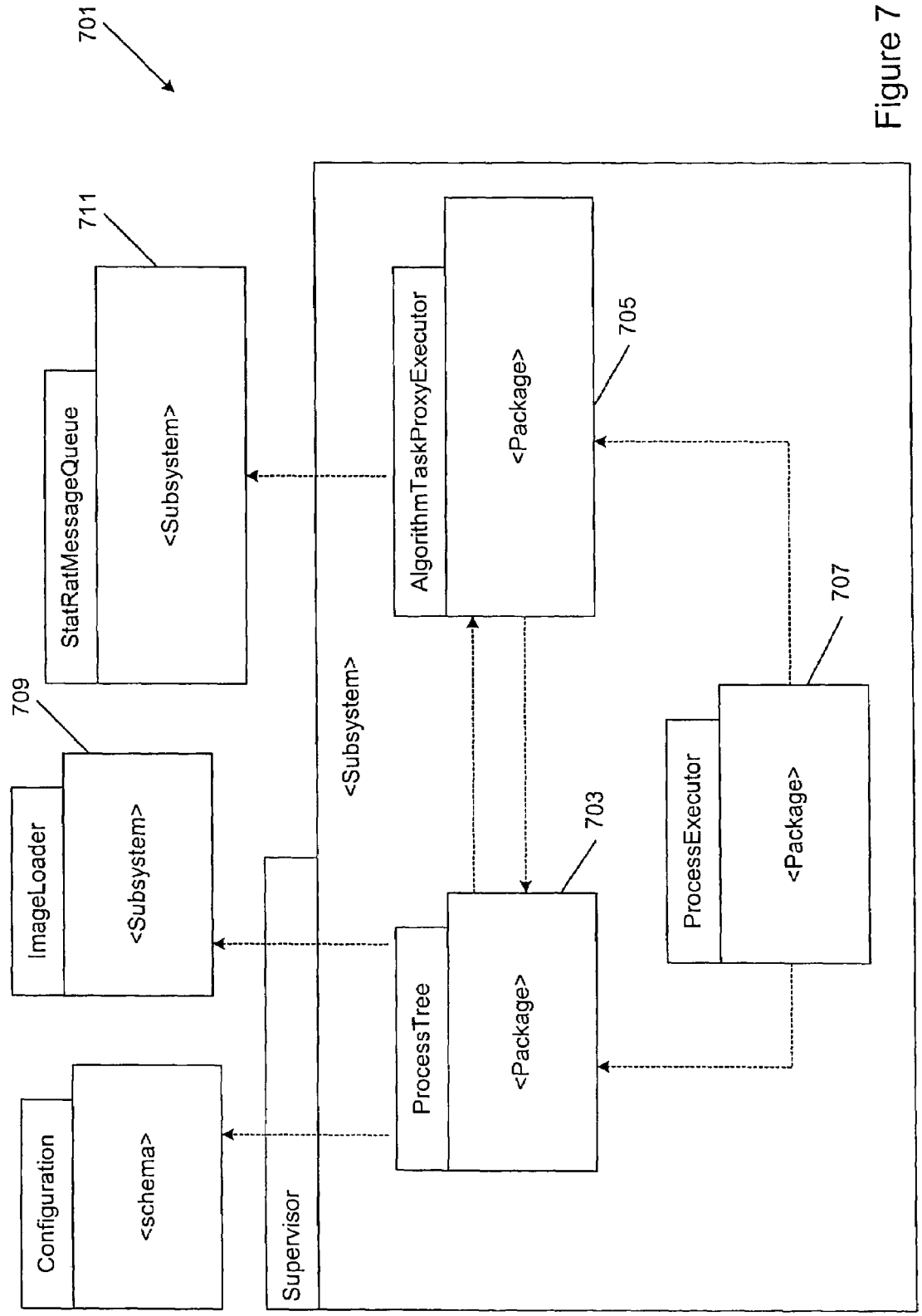
FIG. 7 depicts a supervisor subsystem in accordance with one embodiment of this invention.

In one embodiment, depicted in FIG. 7, a Supervisor subsystem 701 comprises three parts. They are a ProcessTree package 703, an AlgorithmTaskProxyExecutor package 705, and a ProcessExecutor package 707.

The ProcessTree package 703 contains classes that deal with getting process data from database, storing process data in memory, creating process nodes, linking process nodes to the process tree, running processes or tasks, and updating process status to the database. It interacts with the AlgorithmTaskProxyExecutor 705 to run the algorithm tasks and invokes an ImageLoader subsystem 709 to run the image-loading tasks. The ProcessTree package uses persistent objects from the Configuration subsystem (composite processes, tasks, and experiment processes) and their corresponding process models.

The AlgorithmTaskProxyExecutor package 705 contains classes that deal with dispatching analysis tasks to feature extractor servers, listening for responses from feature extractor servers, and tracking the started tasks. To this end, it employs a MessageQueue 711.

The ProcessExecutor package 707 contains classes that deal with building a top-level process tree for a particular Supervisor, instantiating task-related objects, running the process tree, and starting the Supervisor as a NT service, for example.

Feature Extractor

In accordance with preferred embodiments of this invention, a Feature Extractor is a server that provides task execution services to the automated system. The system has any number of FeatureExtractor servers running on various servers around an enterprise. The servers may be dedicated servers and/or individual workstations running extractors in off hours.

In one embodiment, the Feature Extractor uses four message queues, all implemented with Oracle Advanced Queuing:

Task Request: messages to the Server requesting that a task be run

Task Response: messages from the Server giving task status after completion

Ping Request: messages to the Server requesting task status

Ping Response: messages from the Server giving task status in response to a ping In a specific implementation, the Feature Extractor has two components, a small NT service (FeatureExtractorService) and a Java application (FeatureExtractorServer). The NT service is a C++ program that simply starts up the Java application, which then runs by itself until shut down by an operator.

The Feature Extractor Server has multiple threads, the main thread and a series of child threads. The main thread polls two message queues, one for incoming tasks and one for incoming pings (requests for status). These queues deliver a payload that contains the algorithm task id to run or query.

On receiving a task request through the Task Request message queue, the Server creates and starts a thread that uses the Algorithm subsystem to run an algorithm as structured by the database. When the thread completes, the Server sends a status message to the Supervisor through the Task Response message queue giving the status of the algorithm.

On receiving a ping through the Ping Request message queue, the Server figures out the current status of the algorithm that's running and responds with that status through the Ping Response message queue. Pings are handled entirely in the main thread, so the running algorithm never interferes with responding to a ping other than by consuming the CPU completely.

Figure 8A:
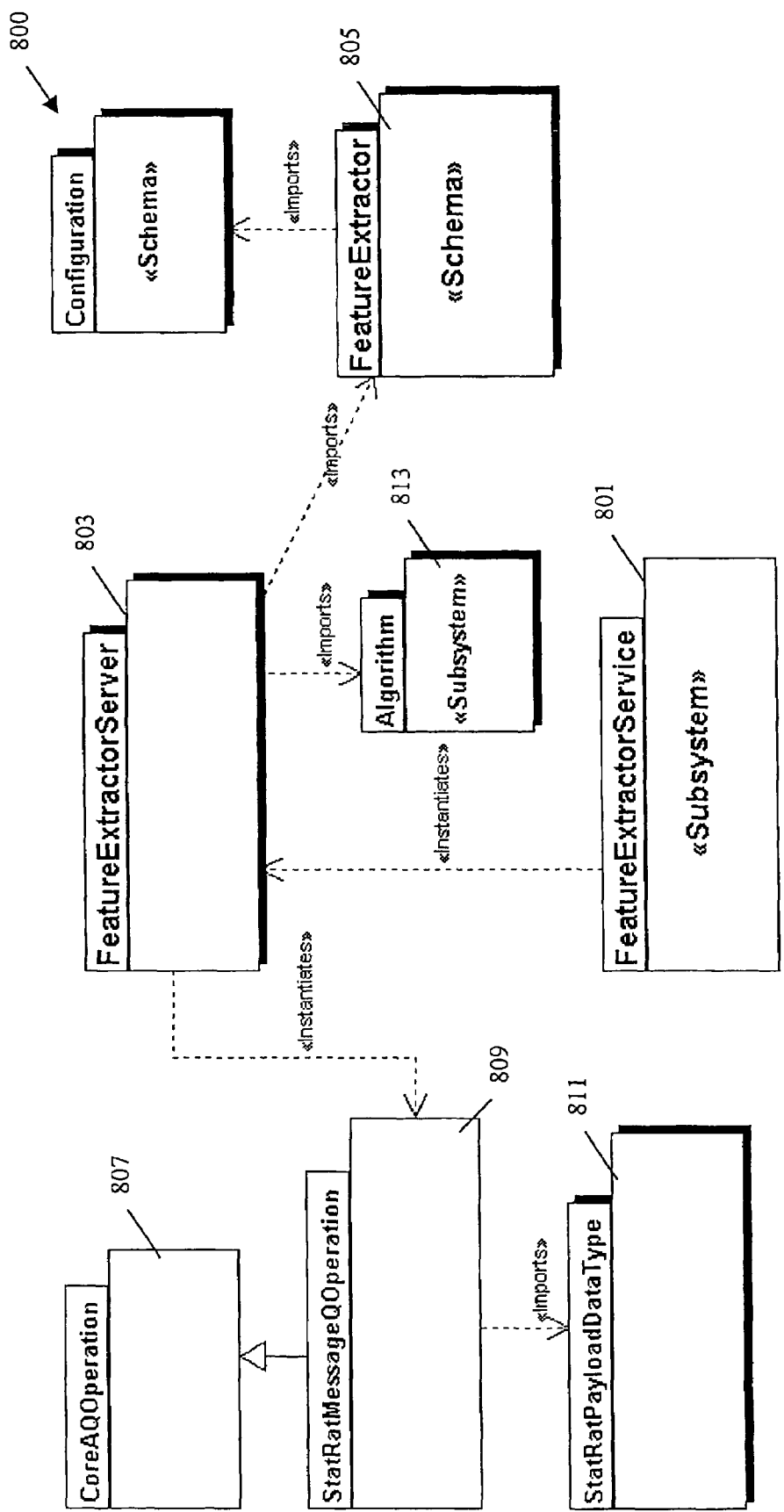
FIG. 8A depicts the architecture of a feature extractor in accordance with one embodiment of this invention.

One architecture of a FeatureExtractor 800 is depicted in FIG. 8A. This architecture brings together all the elements required to run algorithms in an independent server, including message queue operations and algorithm processing.

A FeatureExtractorService package 801 contains a small C++ program that runs as a Windows NT service. This service enables the Feature Extractor to start up automatically in a standard Windows manner. The service instantiates a FeatureExtractor Java application 803. The single parameter for the service is the name of the feature extractor, which it passes to the Java application on the command line. This name corresponds to a FeatureExtractor object in a FeatureExtractor schema 805 in the Oracle database.

The FeatureExtractor schema 805 in the database contains information about the Feature Extractor (name, date created, and so on). The names should be consistent with the FeatureExtractorService name settings mentioned in the prior paragraph. The Process Monitor uses this information in its display of FeatureExtractor status.

The bulk of the Feature Extractor Server involves managing the four Oracle Advanced Queueing queues. A CoreAQOperation package 807 defines a set of base classes and an interface that comprise a reusable basis for specific messaging frameworks. A MessageQOperation package 809 is such a framework, providing factories and queues based on the Core package superclasses. A PayloadDataType package 811 provides a set of data types that one can use to send information through the StatRat queues. An Algorithm package 813 provides a complete system for running an algorithm task. The Algorithm Subsystem is described in more detail below.

Figure 8B:
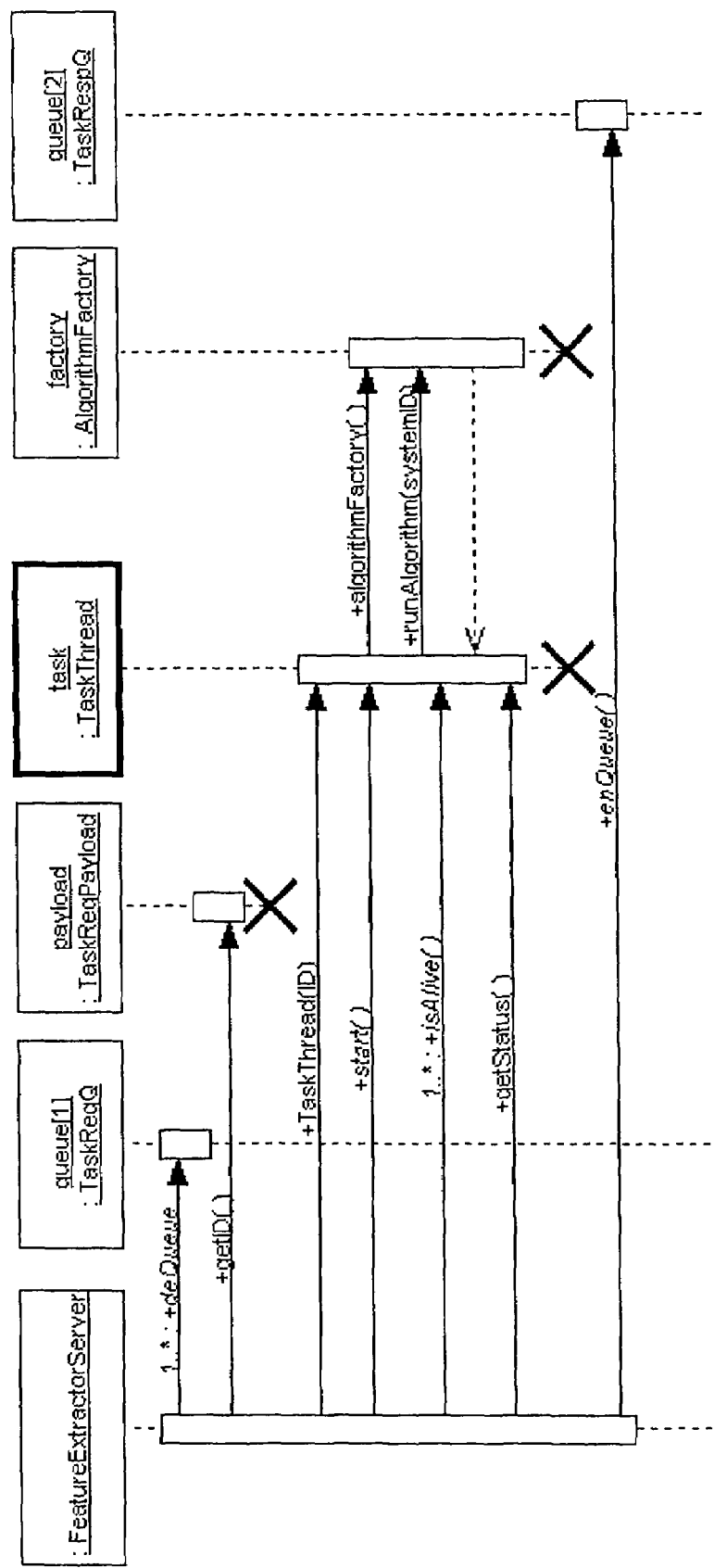
FIG. 8B presents a specific example process of running a task in the feature extractor system.

FIG. 8B illustrates a very specific example process of running a task, an interaction in the FeatureExtractor system. This scenario assumes that the Server has already created the four message queues. The Feature Extractor Server first polls the Task Request Queue (queue in the queue array) by calling deQueue to get any requests to perform a task. While there is no algorithm work going on, this loop continues indefinitely until there is work to do.

On receiving a message, the Feature Extractor Server gets a TaskReqPayload object (downcast from Object). The Server extracts the integer system id of the requested algorithm task from the payload with getID( ). The Server then creates the task thread using the ID and starts the thread. The task creates the AlgorithmFactory object and runs the algorithm with the runAlgorithm method, passing in the systemID.

After starting the thread, the Server polls the thread in a loop asking whether the task is alive. When the algorithm finishes, the AlgorithmFactory object returns and the thread stops. At this point, the looping call to isActive will return false and the Server can proceed. The loop sleeps for 500 milliseconds between each iteration to conserve CPU resources.

After the thread stops, the server gets the status of the algorithm, a TaskStatus enumeration variable set by the algorithm in the task thread object (value will be Complete or Broken). At this point, the thread object is freed for garbage collection, which in turn frees the AlgorithmFactory object for garbage collection.

The Server then enqueues a message in the Task Response message queue (TaskResponseQ), telling the Supervisor what algorithm task has which status (systemID and status). At this point, the Feature Extractor Server resumes the iteration on the Task Request message queue looking for additional tasks to perform.

Algorithm Subsystem

The Algorithm subsystem enables the automated data analysis manager to run algorithms developed as MatLab scripts, C++ class function members, Java methods, etc. Often, these scripts or functions contain only algorithm code. All database and image inputs come through parameters to the script. The Algorithm subsystem contains Algorithm subclasses for each MatLab algorithm, InputData classes for each set of tabular inputs, ImageData classes for each image file input, and ResultData classes for each set of tabular outputs. Different algorithms may share inputs and/or results. Inputs and results are implemented Enterprise Javabeans, for example, residing on the Oracle database server, as both interact heavily with the database.

In a specific embodiment, the Algorithm subsystem uses a C++ version of the CDynArray MatLab data structure to use for tabular inputs and results. The Feature Extractor first activates an Enterprise Javabean based on a Supervisor message it receives. It then uses an Algorithm factory object to instantiate and run the algorithm. The Algorithm interfaces with the MatLab engine interface to run the script, passing in the parameters and getting back the results. After completing the algorithm, the FeatureExtractor frees the AlgorithmFactory object, which in turn frees all the other objects.

Figure 9A:
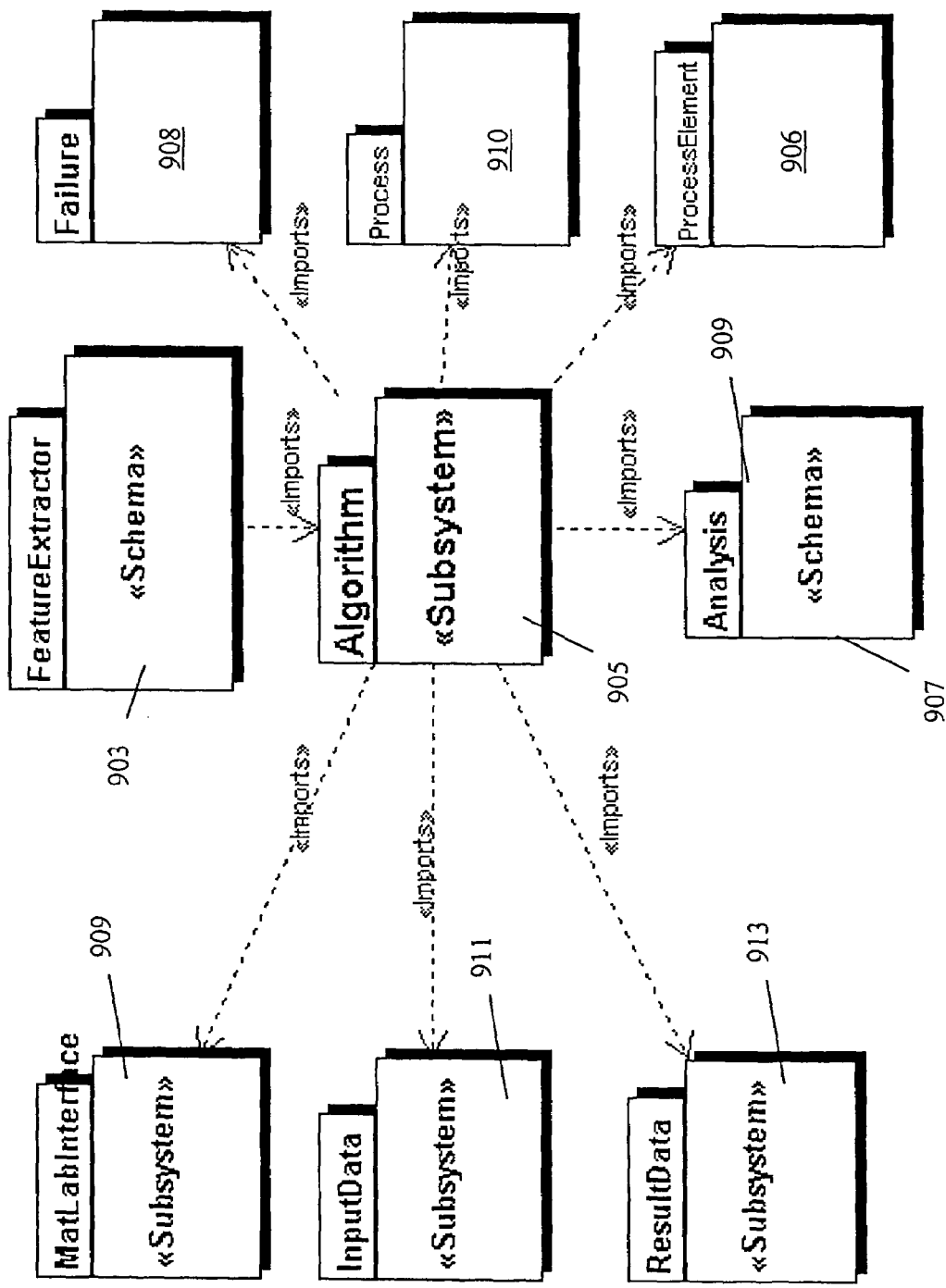
FIG. 9A presents a block diagram of the algorithm subsystem in accordance with one embodiment of the invention.

Preferably, the Algorithm subsystem contains all the code related to instantiating and running an algorithm on a Feature Extractor server. FIG. 9A presents a block diagram of the subsystem's architecture in accordance with one embodiment of the invention.

The Feature Extractor subsystem 903 imports the Algorithm subsystem 905 and starts a thread that accesses the AlgorithmFactory singleton object interface to run an algorithm. The factory in turn queries and activates an AlgorithmTask entity bean in an Analysis schema 907 that supplies details for the algorithm execution. The factory then creates the Algorithm object of the appropriate subclass and runs it, passing in the ProcessElement obtained through a ProcesElement subsystem 906. To run the algorithm, the Algorithm object either uses a C++ MatLab interface 909 to run a MatLab script, creating InputData 911 and ResultData 913 session beans to hold inputs and outputs, or it runs C++ or Java algorithms directly by querying and storing data. The MatLab script or C++/Java algorithm returns a return code and results. If the return code is not 0, the Algorithm object logs a failure in the database through a Failure subsystem 908; otherwise, it stores the results. The Algorithm and its AlgorithmFactory return the ultimate status to the caller. The Algorithm object ensures that the process only stores results once through the Process subsystem 910.

Figure 9B:
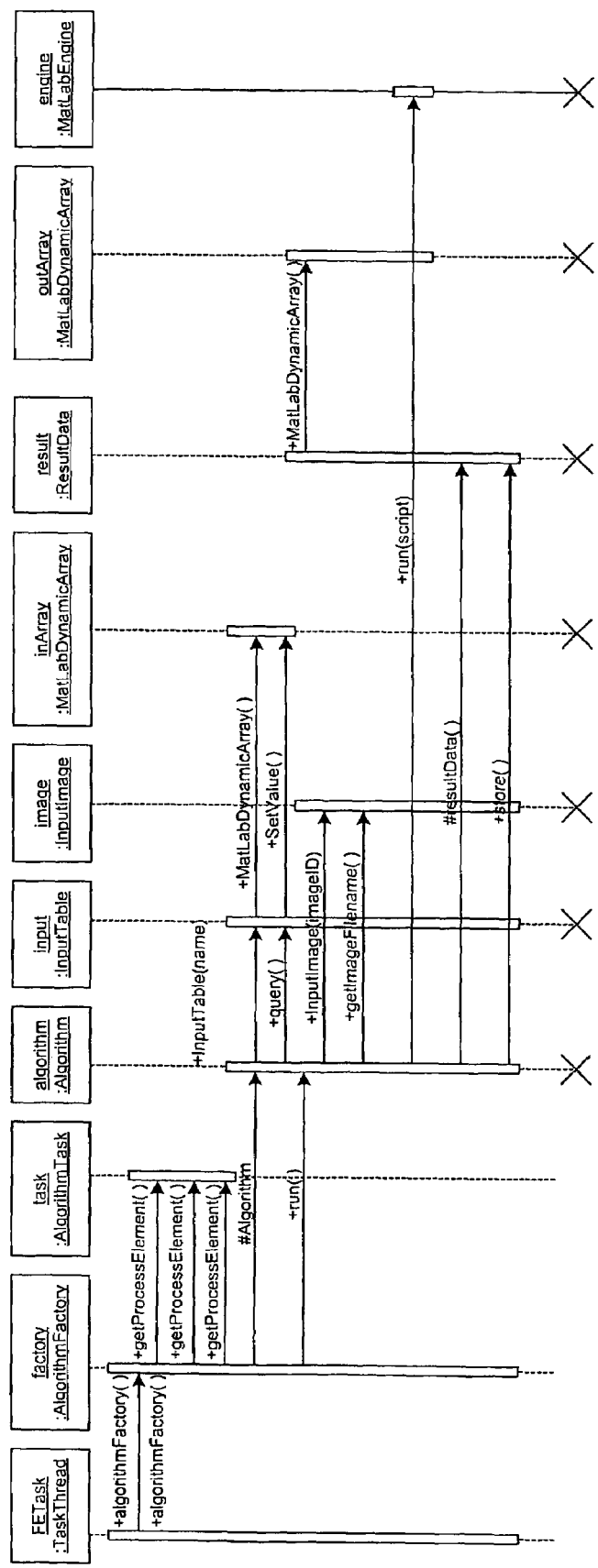
FIG. 9B presents a sequence diagram illustrating certain actions of the algorithm subsystem while it runs an algorithm.

The main action in the Algorithm subsystem is the running of the algorithm. In very specific embodiment, the sequence diagram of FIG. 9B shows how this works.

The Feature Extractor instantiates the factory. The factory instantiates the algorithm task bean to get the process element (an interface for the various kinds of objects that a task may process) and the task arguments. Based on the algorithm name, the factory then instantiates the appropriate subclass of Algorithm, passing in the process element and the argument list.

The constructor for the Algorithm creates InputTable and InputImage session beans of the appropriate subclasses. InputTable objects in turn create an MatLabDynamicArray object and construct their internal data through database queries. The constructor then creates a ResultData session bean, which creates another MatLabDynamicArray object to hold the results. The Algorithm calls MatLab to bind the various arguments, including the returns, into the MatLab engine using the argument names or values passed from the AlgorithmTask.

The factory then runs the algorithm by calling the run method on the Algorithm object. This method starts the MatLab engine, binds in the input arguments, the input data array(s), the result data array, and the return code, all of which correspond to named elements in the command script (not shown explicitly for simplicity). The Algorithm then runs the command script.

Note that a TIFF image (WellImage table) is passed by the InputData object's constructing a temporary TIFF image file available to the server and passing the resulting path and filename as a string argument to the command script.

The script processes the inputs and produces an error return and a single dynamic array. The algorithm object checks the error and handles it as appropriate, raising an exception as required. Exception handling uses the Application Failure Logger subsystem to log the error to the database. It also handles the recovery logic, permitting the algorithm to control retries or other recovery processes.

If the return code is 0, it means the algorithm succeeded, so the Algorithm calls the store method on the ResultData array to pass the mxArray (internal MatLab array) to the ResultData entity bean for storage in the database. The bean stores the data and returns, and the Algorithm run method returns to the factory runAlgorithm method. The factory then frees the Algorithm object for garbage collection and returns.

Version Dependent Algorithm Launcher Design

The automated system processes comprise many algorithm tasks for processing data. Different versions of an algorithm may behave differently. Usually the latest version is the one that works best in most circumstances and is the one deployed to run the process. However, members of a group may need to run different versions of the algorithms through the system at the same time. For example, one may need to use different versions of data analysis algorithms to analysis the ever-increasing data sets to further test the algorithms themselves, or one may want to run a specific version of algorithm because we need the functions of that version.

As indicated, the feature extractor server is the algorithm task manager. It launches and/or stops algorithm tasks. The feature extractor server and the high-level algorithm routines are, in the specific implementation, all Java modules, while the low-level algorithm routines can be implemented in either Java or C/C++. In the case of algorithm modules implemented in C/C++, they may reside in Windows DLLs. Therefore, the basic question here is how to run different versions of algorithms in Java and indirectly from Windows DLLs in a dynamic way.

Usually when a Java virtual machine starts, it uses the default class loader (the system class loader) to load classes specified at the system class path. If two or more versions of Java classes with the same class name (package structure also the same) are specified at the class path, there is no way to tell the system class loader which one to load to run a specific version, the system class loader always loads the one it finds first on its class path. The same situation holds true for loading DLLs in Windows. The usual way to load a DLL is to put the DLLs in the search path of the system. If we put multiple versions of a DLL with the same name at the search path, Windows only loads the one it finds first on the search path.

To run different versions of Java program in a dynamic way, one can use customized class loaders to load and run different versions of algorithms. Java provides a standard way to load and run different versions of algorithms with the same class signature but at different file system or network locations. To use the feature extractor server to load and run different versions of Java algorithms, one needs to install a customized algorithm class loader for the feature extractor server. Therefore when the feature extractor server gets a request to run a specific version of an algorithm, it can be configured to figure out where the class files (or jar files) are located for the requested version, and then use the customized algorithm class loader to load and run the algorithm. In this way, the feature extractor server can run multiple versions of an algorithm either sequentially or in parallel in one JVM, using different instances of algorithm class loaders to load the classes.

In the case that Java algorithm needs to use a native (C++ or other natively compiled code) method to implement some of its functionalities, the customized class loader can also be instructed to load the version dependent DLL at a specific location. This DLL may be called the entry DLL for the Java algorithm. If this entry DLL depends on other version-dependent DLLs, and the dependencies can be chained to arbitrary depth, then one needs a mechanism to have those version-dependent DLLs finds and loads their dependent ones. There are a couple of ways to do that.

Dynamically loading DLLs is a preferred approach. The usual way to dynamically load a DLL starts with calling LoadLibrary with the DLL name as the parameter. However, one can also use LoadLibrary to specify the absolute path of the DLL's module, in this way we can load the DLL of the desired version with the same name but at different network location.

The following procedures apply to run multiple versions of algorithms with either Java or DLLs.

Put all Java classes (in either jar files or expanded folder structure) and DLLs for a particular version of algorithms in a network folder designed to hold that version's contents.

Put all versions independent Java classes and DLLs in a common network folder. Java classes and DLLs are registered with the CLASSPATH and PATH environment variables respectively.

In a configuration file, specify the mappings between algorithm versions and the paths that point to those versions.

The feature extractor server reads the configuration file when it starts. As it gets an algorithm task request for a specific version, it changes its working directory to the directory that corresponds to the required version. It then uses the algorithm class loader to load classes for that version, and it can also link and load the right version of DLLs down the chain.

The loading mechanism always tries to load Java classes or DLLs from the system standard path first. If the required module is not found, it then tries to load it from the version-tagged path.

Image Loader Subsystem

An image loader subsystem may be used as one of the task executors of the experiment process. It integrates the functionality of the imaging system into the experiment process. Specifically, it carries out the task of registering the well image files with the database so that these images can be traced and processed later.

In a preferred implementation, the image loader is an extension to the supervisor system. The supervisor simply invokes the image loader to carry out an image-loading task as it encounters an imaging task in its execution path.

When the image loader gets an imaging-loading task from the supervisor, it queries the database to get the information about the task. It then uses this information to build a filter to work only with the image files satisfying certain qualifying criteria. The image loader picks up the files, transfers them to a permanent depository and registers them with the database.

The image loader subsystem contains all the code related to run image-loading tasks. In another implementation, the Inage Loader is a separate NT Service running on a separate machine, communicating with the Supervisor through a message queue.

Figure 10A:
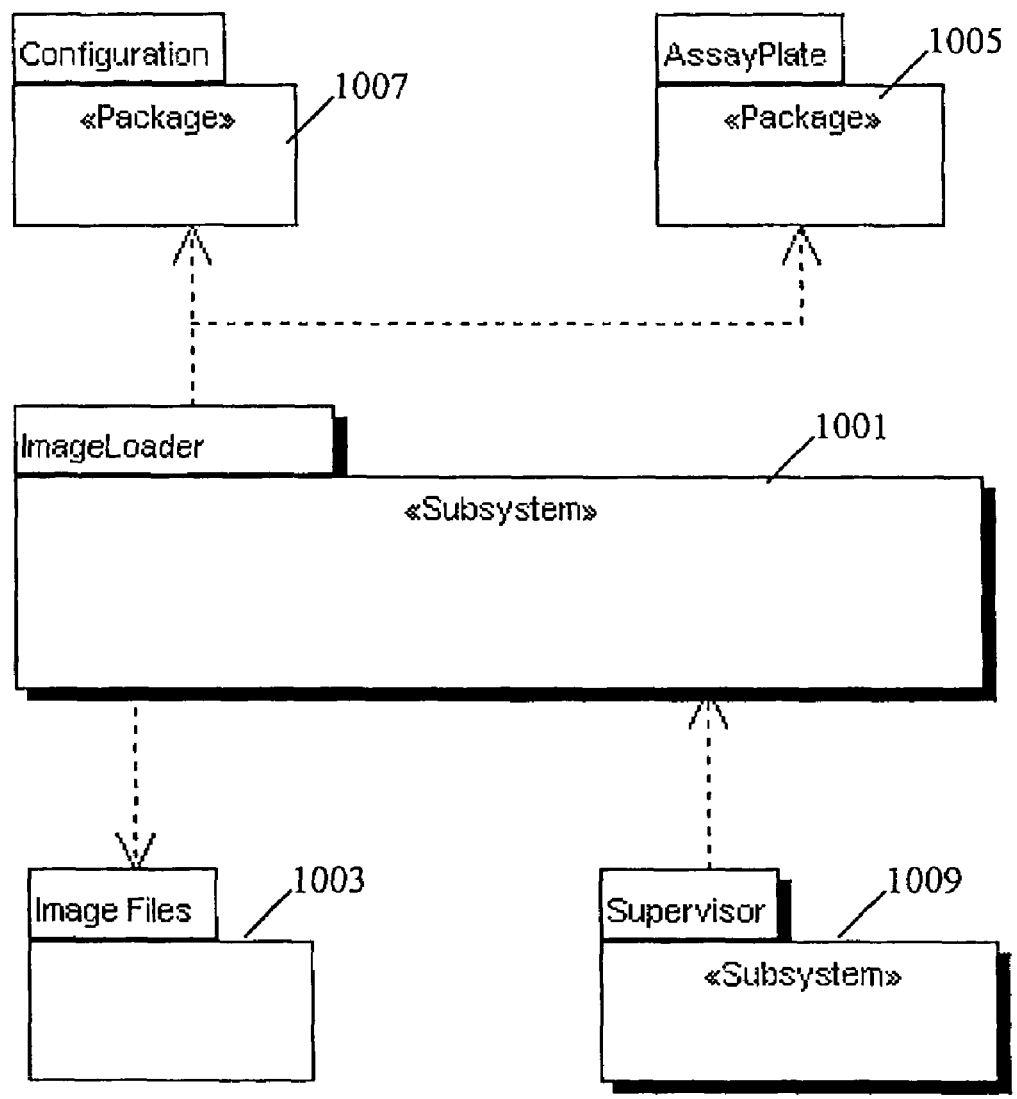
FIG. 10A presents a block diagram of the architecture of an image loader subsystem in accordance with an embodiment of this invention.

As shown in the embodiment of FIG. 10A, an image loader subsystem 1001 interacts with four external packages. They are image files 1003, the AssayPlate schema 1005, Configuration packages 1007, and the supervisor subsystem 1009.

The image files 1003 generated by the imaging station have a fixed file name format that provides the necessary information for the image loader to work with the database. The filename is based on the combination of assay plate barcode, well name, site number, channel number and a prefix. For example, 00023558_B04_S1_W2.TIF means this image is for well B04 of assay plate with barcode 00023558 on site 1 and channel 2.

When the imaging station produces the files, it stores them in a specific image-dumping directory. The Image Loader moves the files from that directory into a network depository and registers the files in the database WellImage table.

The AssayPlate and Configuration packages 1005 and 1007 provide the database objects with which the image loader queries and updates information related to imaging task and well images.

Figure 10B:
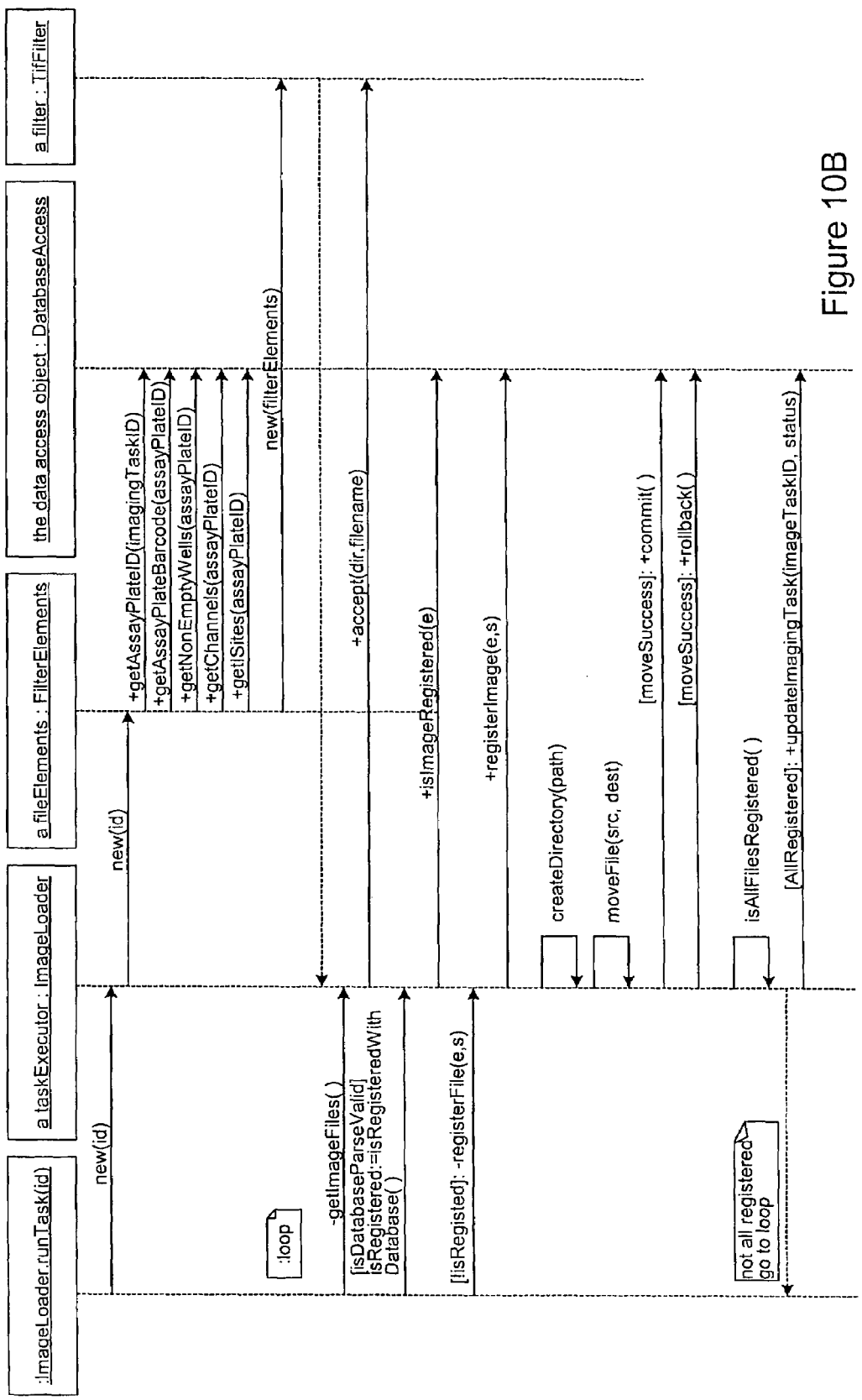
FIG. 10B presents a sequence diagram illustrating activities of the image loader subsystem.

As shown in FIG. 10B, the sequence diagram of the image loader is very straightforward. After creating an image loader object for an imaging task, the run function of the object calls several methods in a loop until all the file registration is finished.

Automated Laboratory Experiment Manager (LabRat) Use Cases

The automated laboratory experiment manager (LabRat) is the automated system component that manages the laboratory experimentation process. This process designs and constructs assay plates and shepherds them through the plating, washing, fixing and staining, imaging, and analysis process. The focus of the automated laboratory experiment manager is the assay plate and the experimental process as well as other, related processes. As indicated above, data analysis process has its own system, the automated data analysis manager. Important subsystems within the automated laboratory experiment manager are the failure and defect tracking processes.

The automated laboratory experiment manager (LabRat) aspect of the invention enables at least some of the following functions: the design of cell-line-based biological experiments on specific biological markers, the tracking and control of those experiments from plate creation through data analysis, the tracking and control of the inputs and infrastructure of the experimental process, and provision for product and process validation of experimental results. Further, the automated laboratory experiment manager may provide tools that allow a Designer to design an experiment that combines cell lines, marker sets, and ActivityBase treatment plates into a collection of assay plates. These tools also permit the full specification of the experimental process through a process model that generates a process (collection of tasks).

Process modeling features can provide the Designer with the ability to specify the structure of the experimental process. The automated laboratory experiment manager then generates processes and tasks for each experiment that automate the process where possible. Automated milestones (barcode scanning, task completion updates, and so on) provide tracking capabilities that give Designers, supervisors, and Experimenters the ability to get experiment status and to intervene in the process where required, preferably through remote interfaces.

In some embodiments, the automated laboratory experiment manager can track the infrastructure of experiments by tracking the individual hardware systems, software systems, reagents, treatments, and maintenance processes. Reports provide planning tools for Designers and Experimenters that help them to keep adequate supplies and systems on hand and in good repair.

In some embodiments described herein, the automated laboratory experiment manager helps to validate experimental results by storing the results and by enabling feedback from scientific analysis of the results. Experimental result validation embodies internal consistency of the results and reproducibility of the results. Consistency metrics (cell distribution, focus/exposure tests, contamination tests, control measure consistency with respect to benchmarks) and reproducibility metrics (variance or standard deviation or coefficient of variation of consistency metrics) provide a way for Designers and Experimenters to identify result failures in images, wells, and plates. The failure and defect tracking systems track these defects and the failures they cause. The stored results thus form a part of the experimental protocol.

The automated laboratory experiment manager may help to validate experimental processes by storing the processes and tasks undertaken as part of the experiment. These process and task objects may provide a complete history of the experiment with all significant milestones recorded with their date and time together with their process models, reusable protocols for generating the process for each experiment. The failure and defect tracking systems track defects and failures in the processes and tasks reported by the process actors (human and automated). The stored process information thus forms a part of the experimental protocol.

As shown in a context diagram (FIG. 11A) of exemplary use cases, the automated laboratory experiment manager has both human and automated roles. A Designer 1101 is an employee responsible for the design and supervision of an experiment. An Experimenter 1103 is an employee responsible for the conduct of an experiment. Note that in many scenarios the Designer 1101 can do anything in the system that the Experimenter 1103 can do. A Specialist 1105 is an employee responsible for any of a variety of infrastructure systems hardware, software, reagents, treatment plates, tissue culture). A Robot 1107 is a hardware device that actively participates in the experimental or maintenance process, updating status and failure information in an Experimental Database as required. An Automated Process Generator 1109 is a server that automatically generates processes from process models. An Experimental Database (not shown explicitly) is a database (e.g., an Oracle database) that contains the persistent experiment protocols, models, and other laboratory-related information. Since virtually every aspect of the system uses the Experimental Database, the context diagram does not explicitly show it or the connections from the use cases to it. An ActivityBase 1111 a database that contains records of treatments for all departments of an organization.

Figure 11A:
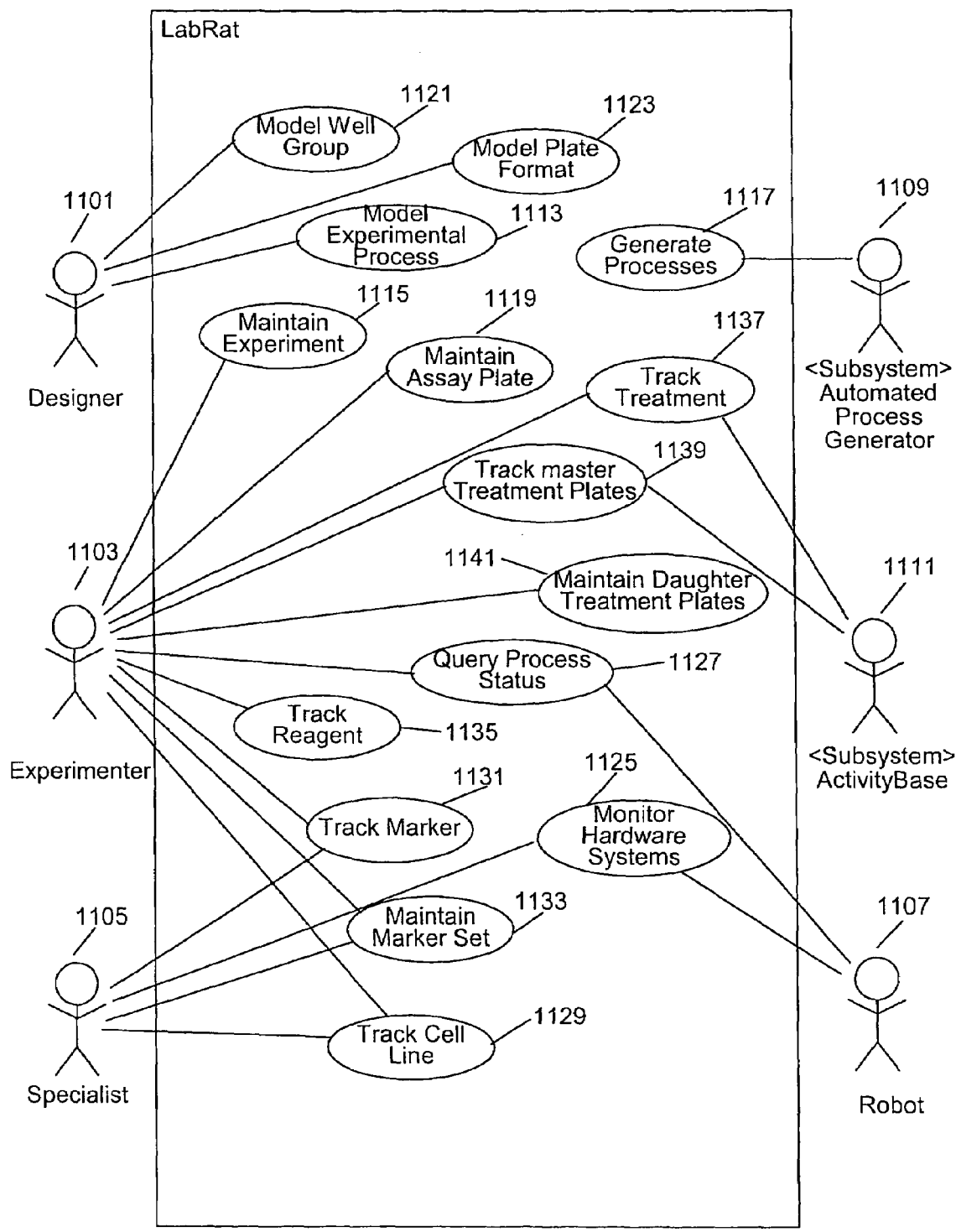
FIG. 11A presents a context diagram of exemplary use cases handled by an automated laboratory experiment manager in accordance with an embodiment of this invention.

The context diagram of FIG. 11A shows how the above actors communicate with the use cases that make up the automated laboratory experiment manager in accordance with one embodiment of this invention.

A Model Experiment Process use case 1113 builds process model graphs. A Maintain Experiment use case 1115 creates an experiment process from an experiment process model. A Generate Processes use case 1117 generates composite processes and tasks under the experiment process model.

Typically, process generation works on an as-required basis (just-in-time process generation). This use case generates those processes next in order in processing sequence. Process generation takes into account the model element level and the process element for the process (an experiment, usually) by generating the correct number of processes for the process element (all the wells on all the plates in the experiment, for example). It also generates all processes under a composite process marked as parallel. Sequential composite processes generate their children one at a time in sequence as the processes end. Also, the process generator generates processes for parent composite processes with a start date greater than or equal to the current date, allowing the system to control process generation timing.

Suitable processes of the Generate Processes use case 1117 are depicted in Table 8 below.

TABLE 8

| Actor | System |
| --- | --- |
| Query all experiment processes that do not have an end date, that have a start date greater than or equal to the current date, and that have the root experiment as a direct parent. | Retrieve the processes and any objects needed to determine what the next process is to generate. |

TABLE 8-continued

| Actor | System |
| --- | --- |
| Generate the next set of processes for each experiment process. End the use case. | Insert the new processes and process element links. Commit the transaction. |

A Maintain Assay Plate use case 1119 may be understood as follows. The Experimenter creates, changes, and tracks assay plates through any number of processes. To create an assay plate, the Experimenter queries a cell line and marker set, then generates an assay plate by, for example, supplying a new assay plate barcode and the cell line passage number.

At some point in the processing of the plate, a process applies a treatment to the plate. At this point, the Experimenter may supply the barcode of the daughter treatment plate that supplied the treatment compounds for the plate, and the System generates the wells for the plate based on the master treatment plate format. The System sets the well group type based on the type that the master format specifies.

At any time, the Experimenter can designate the assay plate as no longer available—for example, the plate may be too old for further use given the reagents and cells on the plate, or it may have been damaged during processing.

When the plate has been processed through fluidics, a Specialist may mark the plate processed, indicating it should no longer be available for tasks involving plate processing (non-repeatable tasks).

It is possible to combine several daughter treatment plates onto a single assay plate. Thus a well may have more than one treatment associated with it through multiple associated treatment plate wells. It is also possible to use a master treatment plate as a daughter plate. Also, one may want to create an operational objective for the plate that specifies target metrics for things like number of cells per well.

Some processes of the Maintain Assay Plate use case 1119 are depicted in Table 9 below.

TABLE 9

| Actor | System |
| --- | --- |
| Create the assay plate using a marker set, cell line, cell line passage number, and a barcode, optionally entering any of the system characteristics (vision, mission, risk, objectives, and so on). | Create the assay plate in the Experimental Database and display it (barcode, system characteristics, marker set, cell line, and passage number. |
| Query an existing assay plate. | Display the assay plate and its wells (if any), showing the well groups and relative concentrations of the treatments (if any), and show the barcode, processing status (Processed or Not Processed), and availability of the plate. |
| Modify the system characteristics of the plate (vision, mission, risk tolerance, risk, operational objectives). | Display the modified system characteristics and save them to the database. |

TABLE 9-continued

| Actor | System |
| --- | --- |
| Change the availability status of the plate to False when the plate is no longer available for analysis. | Display the modified plate with availability set to False. |
| Change the processed status of the plate to True when the plate is no longer available for processing. | Display the modified plate with processed set to True. |
| End the use case. | Commit the transaction. |

The Maintain Experiment use Case 1115 may be understood as follows. The Experimenter creates an experiment by generating an experiment process from an experiment process model and associating a group of assay plates with it. The Experimenter would have already created the assay plates in a scenario of the Maintain Assay Plate use case 1119. The Generate Processes use case 1117 will generate the tasks for the process on or after the start date the Experimenter specifies.

Some processes of the Maintain Experiment use case 1115 are depicted in Table 10 below.

TABLE 10

| Actor | System |
| --- | --- |
| Generate the experiment process from an experiment process model, setting the start date and any of the optional system characteristics (vision, mission and so on). | Generate the process tree and update the process start date and system characteristics. Display the process with its start date and system characteristics. |
| Associate a group of assay plates with the experiment process. | Associate the plates in the group with the experiment process. |
| Query existing experiments. | Retrieve the experiments and display them with start date, end date, and system characteristics. Display the list of associated assay plates. |
| Select and modify any unprocessed experiment (an experiment with a start date in the future) by adding assay plates. | Associate the assay plates to the experiment process. |
| Select and modify any experiment by changing the system characteristics [or by adding assay plates or assay plate groups] | Update the system characteristics and associate the assay plates to the experiment process. |
| Select and delete an unprocessed experiment (an experiment process with no task with an end date). | Remove the unprocessed experiment and all its child processes from the Experimental Database. |
| Select and modify an experiment by removing any unprocessed plates (all at once, aborting the experiment, or one at a time). | Remove the plates from the experiment. |
| End the use case. | Commit the transaction. |

A well group is a collection of wells on one or more plate formats. Well groups permit data analysis to distinguish certain wells on plates as a unified group. Modeling well groups permits a Designer to create standard well groups in certain plate locations, such as control groups. As well, an Experimenter (or Data Analyst) can create an arbitrary group of wells for analysis purposes.

A Model Well Group use case 1121 permits the Designer to create a group and its wells, to change its structure, or to remove the group from active availability in the database.

Exemplary processes of the Maintain Experiment use case 1121 are depicted in Table 11 below.

TABLE 11

| Actor | System |
| --- | --- |
| Create a well group, giving it a name and optional description and reuse potential as well as supplying the optional system characteristics (vision, mission, objectives, and so on). Specify an ordered list of well-group wells (row and column) and a group type from a lookup table of types. | Create the group in the Experimental Database. Set the creator and the creation date to the user creating the group model and the current system date, respectively. Display the group model, its group type, and its list of wells. |
| Query a well group. | Display the well group and its wells, displaying system information, name, description, reuse potential for the group and the row and column for each well. |
| Select a well group and change the name, description, reuse potential, system characteristics, group type, or well structure of the group. | Display the changes and save them to the Experimental database. |
| Remove the well group. | Mark the system as inactive and remove the system from the display. |
| Duplicate the well group, supplying a new name. | Copy the group and its wells into a new object, setting the name to the new name. |
| End the use case. | Commit the transaction. |

A Model Plate Format use case 1123 may be understood as follows. A plate format is a plate geometry and a collection of well groups laid out on a plate template. A plate format is the template for any number of plates, each of which has exactly one plate format that, once assigned, does not change. By designing plate formats, the Designer can create a reusable template that describes the basic layout of wells on a plate for use in generating assay plates. The Designer associates this plate format with a master treatment plate, and through that plate it determines the well structure of all the daughter treatment plates associated with the master plate and also of all the assay plates to which the daughter treatment plates are applied.

The Model Plate Format use case 1123 permits the Designer to create a plate format from the existing set of well groups (see the Model Well Group use case) and a plate type, to change its structure (if it is not already in use on existing plates), or to remove the group from active availability in the database.

Some processes of the Model Plate Format use case 1123 are depicted in Table 12 below.

TABLE 12

| Actor | System |
| --- | --- |
| Create a plate format, giving it a name and optional description and reuse potential as well as supplying the optional system characteristics (vision, mission, objectives, and so on). Choose a plate type from a lookup list of plate types. Add any number of well groups to the list of well groups for the format. | Create the group in the Experimental Database. Set the creator and the creation date to the user creating the group model and the current system date, respectively. Display the group model, its plate type, and its list of well groups. Check that none of the well groups overlaps on the plate layout (offer only non-overlapping well groups for inclusion in the list through the user interface). |
| Query a plate format. | Display the plate format and its list of well groups, displaying system information, name, description, reuse potential for the group, plate type, and the well group name and description for each well group. |
| Select a plate format and change the name, description, reuse potential, or system characteristics. | Display the changes and save them to the Experimental database. |
| Remove the plate format. | Mark the system as inactive and remove the system from the display. |
| Duplicate the plate format, supplying a new name. | Copy the plate format and its well groups into a new object, setting the name to the new name. |
| End the use case. | Commit the transaction. |

The Model Experimental Process use case 1113 may be understood as follows. As explained above in the discussion of the "Process Generator" subsystem, an experimental process model is a tree hierarchy of composite processes and tasks that represent the elements of the experimental process that one may want to track in terms of start and end dates. FIGS. 6A and 6B and the associated discussions set forth a typical experiment model.

Figure 11B:
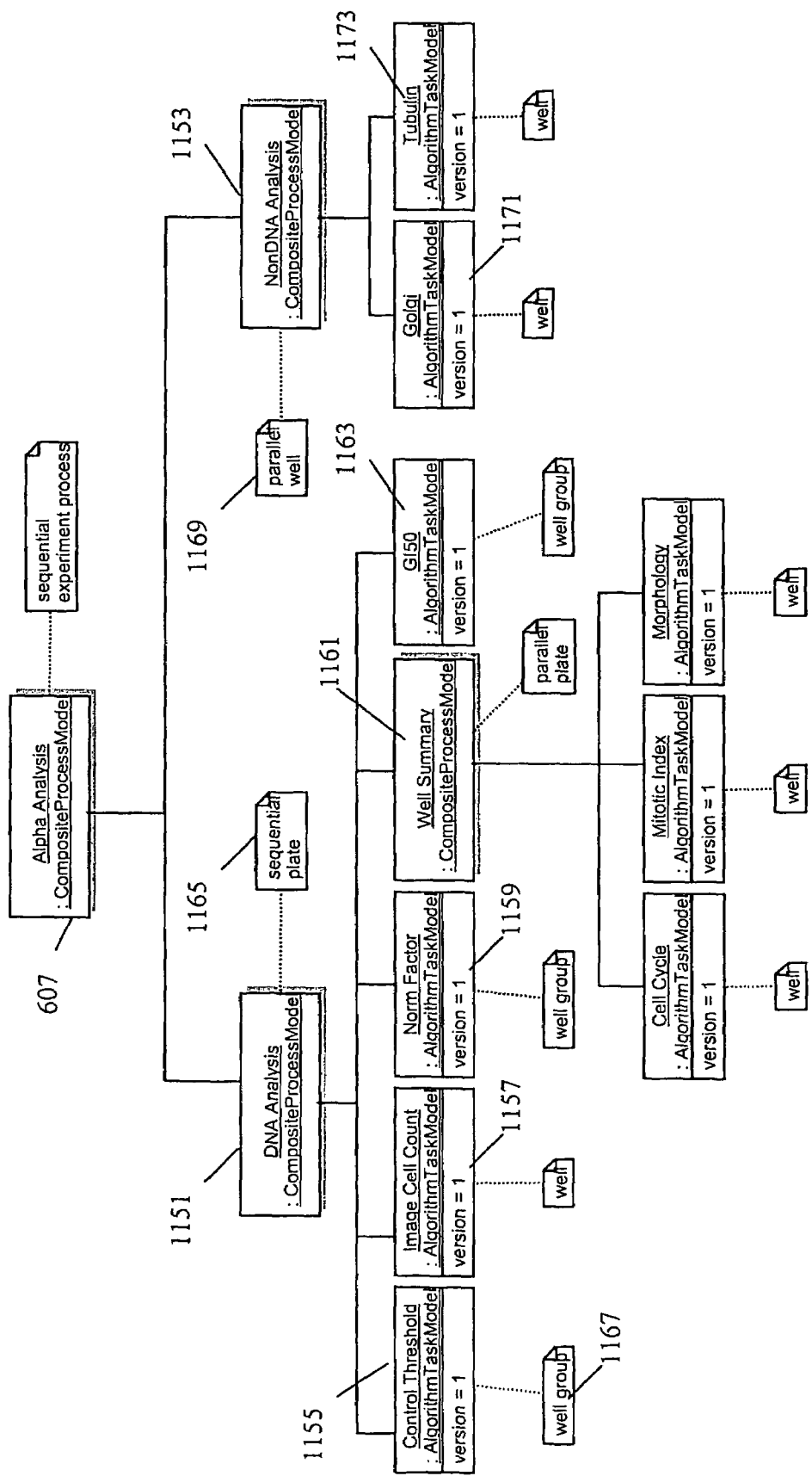
FIG. 11B illustrates a possible analysis process model with a representation of a model originally identified in FIG. 6A.

Following up on that discussion, FIG. 11B illustrates a possible analysis process model with a representation of the Alpha analysis process model 607 (originally identified in FIG. 6A). This is a reusable composite process with multiple parts. The tree consists of a top-level composite process model 607, two composite process models 1151 and 1153 at the second level, each containing a set of different kinds of process models including tasks, composite processes, and algorithm tasks. As shown, the composite contains two parts, a DNA analysis 1151 and a non-DNA analysis 1153. The DNA Analysis 1151 contains a Control Threshold algorithm 1155 followed by an image cell count algorithm 1157 followed by a norm factor algorithm 1159, followed by a well summary process 1161 containing three algorithms, and terminated by a GI50 algorithm 1163. A sequential marking 1165 on the DNA Analysis composite process model 1151 indicates the five subprocesses run sequentially. The plate marking (also 1165) indicates the DNA Analysis is done once for each plate in the experiment. Similarly, for the Control Threshold task 1155, the well group marking 1167 indicates the algorithm runs once for each well group on each plate. The second composite process, non-DNA Analysis 1153, has a parallel marking 1169, which means its two subprocesses run in parallel.

Figure 11C:
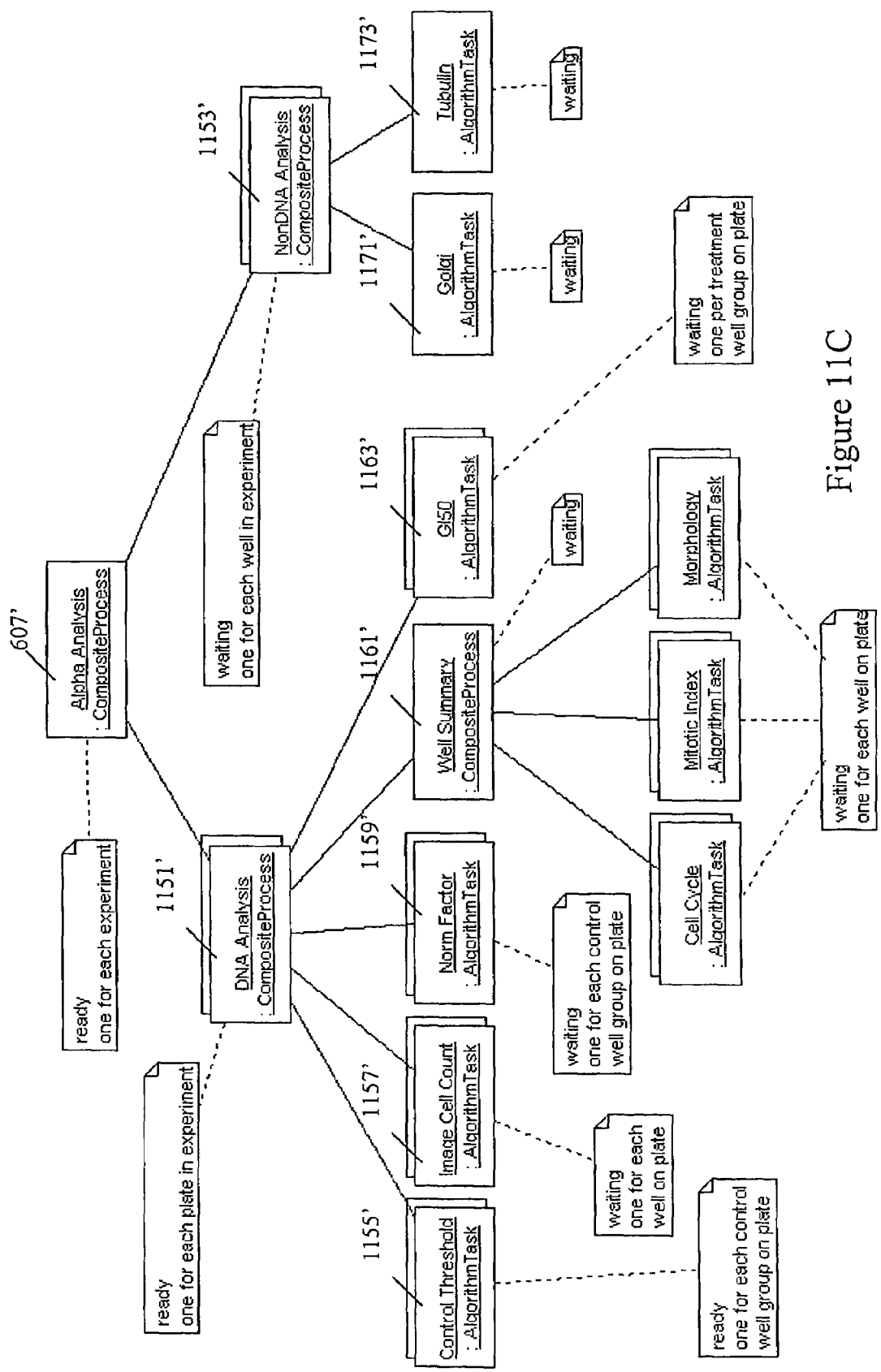
FIG. 11C illustrates a process tree created from the process model depicted in FIG. 11B.

When the database creates a process tree (see FIG. 11C) from this structure, it sets the status as appropriate. For example, the FIG. 11C depicted tree represents the process tree generated from the above model:

The process model generates multiple processes for each process model depending on the iteration structure. There is one Analysis Process for the experiment. There is one DNA process for each plate in the experiment. There is one Golgi task 1171' for each well on each plate in the experiment (all running in parallel with each other and with the DNA tasks. And so on.

Some processes of the Model Experimental Process use case 1123 are depicted in Table 13 below.

TABLE 13

| Actor | System |
|---|---|
| Create a composite process model, specifying the name and description of the process and any system characteristics (vision, mission, objectives, and so on), and optionally connecting it to a parent composite process model. This may be an experiment model or a generic composite process model. Set the composite to execute its children in parallel or sequentially. | Save the process model in the Experimental Database, optionally linking it to the parent composite process. |
| Create a task model, specifying the task name and description, parent process model, and any system characteristics. | Save the task model in the Experimental database, linking it to its parents. |
| Query an existing process model. | Get the process model tree from the Experimental Database. Display the descriptions. |
| Duplicate a process model. | Add a new process model tree copied from the queried one to the Experimental Database. Change the name by adding "Copy of" to create a unique name. |
| Change the name or description of the queried process model or any of the system characteristics. | Update the name and description of the process model in the Experimental Database. |
| Remove an experimental process model. | Mark the process as inactive in the Experimental Database. |
| End the use case. | Commit the transaction to the database. |

A Monitor Hardware Systems use case 1125 can be understood as follows. The automation features of the automated system involve the coordination and maintenance of various hardware systems such as robots and incubators. Each such system is tracked as part of the Configuration subsystem of the system database for failure and defect tracking purposes. As well, a specialist can monitor the current status of these systems.

The system can display database records of hardware status. Alternatively, the system canl integrate real-time hardware monitoring features into the system, providing web-based updates and control of individual hardware deliverable systems.

Some processes of the Monitor Hardware Status use case 1125 are depicted in Table 14 below.

TABLE 14

| Actor | System |
|---|---|
| Query the system for current hardware status. | Display a list of all hardware deliverable systems. Display any feedback available in the database about the system. |
| Log a comment on a specific hardware system. | Save the comment with a time stamp to the Experimental Database, linking the comment to the hardware system. |
| End the use case. | Commit the transaction. |

A Query Process Status use case 1127 can be understood as follows. The Experimenter needs to know the status of the experimental processes for all active processes. The Query Process Status use case 1127 presents this information to the is Experimenter, showing the process trees of active processes and allowing the Experimenter to drill down to the start and end times of individual processes, to see any comments about the processes, and to log comments about specific processes.

Some processes of the Query Process Status use case 1127 are depicted in Table 15 below.

TABLE 15

| Actor | System |
|---|---|
| Query the system for current process status. | Display a list of active processes, listing all process trees with active tasks in a tree hierarchy display. For each process display the start time and end time of the process and any feedback for the process. |
| Modify status to Complete or Broken. | Set the status in the database and set process end date to the current date and time. |
| Log a comment on a specific process. | Save the comment with a time stamp to the Experimental Database, linking the comment to the process object. |
| End the use case. | Commit the transaction. |

A Track Cell Line use case 1129 can be understood as follows. A cell line is a specific kind of cell that a Designer can use in an experiment. The automated system typically maintains a specific set of cell lines. When a Designer creates an assay plate, he or she specifies a cell line for the plate. The Track Cell Line use case 1129 lets the Experimenter or Specialist create, modify, or remove cell lines from the set of available lines in the system. See the discussion of the Maintain Assay Plate use case 1119 for the association of cell lines to assay plates.

Some processes of the Track Cell Line use case 1129 are depicted in Table 16 below.

TABLE 16

| Actor | System |
|---|---|
| Create a cell line, specifying its name, description, reuse potential, and any optional system characteristics (mission, vision, operational objectives, and so on). | Save the cell line to the Experimental Database. |

TABLE 16-continued

| Actor | System |
|---|---|
| Query a set of cell lines on id, name, or description. | Display the cell line name and description and a list of all active assay plates for the cell line. Also display any cell line feedback. |
| Change the cell line name, description, reuse potential, or system characteristics. | Save the changes to the Experimental Database. |
| Remove a cell line. | Mark the cell line inactive in the Experimental Database. |
| End the use case. | Commit the transaction. |

A Track Marker use case 1131 may be understood as follows. A marker is a specific reagent or other indicator detectable in an image. For example, the marker may be an autofluorescent reagent used to mark specific proteins or other materials in the well and thereby show the location of such materials in an image obtained with a fluorescent microscope. In a typical example, each marker fluoresces at a particular frequency of light and occupies a channel on the microscope. The Specialist may create, change, or remove markers in the automated system. See the discussion of a Maintain Marker Set use case 1133 for the association of markers to assay plates.

Exemplary processes of the Track Marker use case 1129 are depicted in Table 17 below.

TABLE 17

| Actor | System |
|---|---|
| Create a marker, specifying its name, description, reuse potential, and any optional system characteristics (mission, vision, operational objectives, and so on). | Save the marker to the Experimental Database. |
| Query a set of markers on id, name, or description. | Display the marker name and description. |
| Change the marker name, description, reuse potential, or system characteristics. | Save the changes to the Experimental Database. |
| Remove a marker. | Mark the marker inactive in the Experimental Database. |
| End the use case. | Commit the transaction. |

The Maintain Marker Set use case 1133 may be understood as follows. A marker set is a collection of different markers assigned to specific channels on a fluorescent microscope (or other instrument employed in the imaging process). A Scientist assigns the marker set to an assay plate to indicate which channels are active on the plate for imaging. See the discussion of the Maintain Assay Plate use case 1119 for the association of marker sets to assay plates.

Exemplary processes of the Maintain Marker Set use case 1133 are depicted in Table 18 below.

TABLE 18

| Actor | System |
|---|---|
| Create a marker set, specifying its name, description, reuse potential, and any optional system characteristics (mission, vision, operational objectives, and so on). | Save the marker set to the Experimental Database. |
| Query marker sets on id, name, or description. | Display the marker set name and description and a list of all markers in the set. |
| Change the marker set name, description, reuse potential, list of markers, or system characteristics. | Save the changes to the Experimental Database. |
| Remove a marker set. | Mark the marker set inactive in the Experimental Database. |
| End the use case. | Commit the transaction. |

A Track Reagent use case 1135 may be understood as follows. A reagent is a chemical other than a treatment agent that someone may use as part of the experiment process, such as media added to wells to hold cells or the fixing chemicals added during the fix and stain process. The Track Reagent use case 1135 lets the system track reagent inventory to ensure that enough reagent volume is on hand to meet experimental demand.

The reagent inventory is a bit complicated by the need to represent various kinds of containment for the reagents. The original packaging of the reagent contains a certain amount of reagent from a given lot, and the automated system stores it in a specific storage location. Much of what the automated system uses as reagent, however, is a working solution comprising several reagents mixed together. As well, Specialists or Experimenters may divide a reagent lot into a series of aliquots, which are by definition a complete division of the original amount into a series of smaller amounts. The system database may track sets of aliquots that come from the same lot and have the same volume, rather than tracking individual aliquots.

In one embodiment, reagent tracking does not attempt to manage the actual flows of reagents through the automated system. Rather, it tracks receipt of reagent lots, creation of working solutions, and aliquoting of the inventories. This permits the recording of experimental protocol information as required to tie experimental results to specific lots. Another embodiment of the system implements a full-scale inventory system for reagents.

Exemplary processes of the Track Reagent use case 1135 are depicted in Table 19 below.

TABLE 19

| Actor | System |
|---|---|
| Create a reagent product with a vendor, product name, catalog number, and notes. | Create the reagent product in the Experimental Database. |
| Query a set of reagent products by vendor, product name, catalog number, or notes. | Display the reagent products with vendor, product name, catalog number, and notes. |
| Change a reagent product by changing the product name, catalog number, or notes. | Save the changes to the Experimental Database. |

TABLE 19-continued

| Actor | System |
|---|---|
| Create a reagent lot from a reagent product, specifying the lot number, inventory date, expiration date, the amount of reagent in each unit of reagent and the units of the amount, the total number of units received for this lot, and any notes on the lot. | Create the reagent lot in the Experimental Database. Specify the current user as the creator of the lot. |
| Query a set of reagent lots from the database by any of the reagent lot fields. | Display the reagent lots queried. |
| Change the reagent lots to correct errors by changing lot number, inventory date, expiration date, amount, unit, units received, and notes. | Save the changes to the Experimental Database. |
| Create a working solution, specifying the set of reagents or working solutions (product inventories) you are combining into the solution, the name of the solution, the inventory date, the expiration date, the amount of solution in each unit of solution and the units of the amount, the total number of units made for this solution batch, and any notes on the solution. | Create the working solution in the Experimental Database. Specify the current user as the creator of the solution. |
| Query a set of working solutions from the database by any of the inventory fields or by specifying an inventory component. | Display the working solutions queried. |
| Change the working solution to correct errors by changing inventory date, expiration date, amount, unit, units made, notes, or the inventory components of the solution. | Save the changes to the Experimental Database. |
| Create an aliquot set from a reagent or working solution (product inventory). Specify the date on which you aliquotted the inventory, the number of aliquots in the set, the volume of the set (all aliquots in the set must have the same volume), the volume unit, and some text giving the purpose of the aliquot set. | Create the aliquot set in the Experimental Database. Specify the current user as the creator of the set. |
| Query a set of aliquot sets from the database by any of the inventory components or by any of the aliquot fields. | Display the aliquots queried. |
| Change the aliquot set to correct errors by changing the aliquoting date, number of aliquots, volume, unit, or purpose or the inventory component that was aliquotted. | Save the changes to the Experimental database. |
| End the use case. | Commit the transaction. |

A Track Treatment use case 1137 may be understood as follows. A treatment compound may be a designated compound obtained by the enterprise for inclusion in the assay program as an "active" substance in the evaluation process. When the enterprise receives a treatment compound, it plates it onto one or more master treatment plates and registers these plates in ActivityBase, the orgaization's research database system. ActivityBase tracks treatment lots rather than treatments, and the automated system needs to track the treatment compound as an object rather than the lots. It identifies the compound with an ID number, but there may be multiple entries for these compounds with slightly different molecular weights and formulas but the same ID. The automated system thus queries ActivityBase to find all registered treatment compounds marked as Cytometrix™ compounds which are not already part of Cytometrix™ and records treatments and IDs in a Cytometrix™ table. It takes the first molecular formula and molecular weight it finds to store in the table. Note that in some embodiments the automated laboratory experiment manager allows for querying and/or examining treatments.

Exemplary processes of the Track Treatment use case 1137 are depicted in Table 20 below.

TABLE 20

| Actor | System |
|---|---|
| Query ActivityBase to find any ID not already in the Experiment database. | Retrieve the treatment compound ID, then query and retrieve the molecular weight and formula for an arbitrary treatment entry for the ID. |
| End the use case. | Commit the transaction. |

A Track Master Treatment Plates use case 1139 may be understood as follows. When an organization receives a treatment compound, it may plate it onto one or more master treatment plates and register these plates in ActivityBase, the organization's research database system. The wells of the master treatment plate thus contain the initial concentration of the compound that serves as the basis for dilution onto daughter treatment plates and assay plates.

The Track Master Treatment Plates use case 1139 lets the Designer track the master plates that contain treatment compounds by querying ActivityBase through an interface. That means that the Designer does not have to create treatment compounds or master plates but rather queries them from ActivityBase. In one embodiment, the Designer cannot change master treatment plates or remove them.

This use case also lets the Designer associate a plate format with the ActivityBase master treatment plate (see the discussion of the Model Plate Format use case 1123 for more information on plate formats).

Exemplary processes of the Track Master Treatment Plates use case 1139 are depicted in Table 21 below.

TABLE 21

| Actor | System |
|---|---|
| Query a set of master treatment plates using barcode, description text, or plate format name. | Display the treatment plate barcodes, descriptions, and ActivityBase plate format name. Display the treatment plate wells. |
| Specify a plate format for the master treatment plate. | Display the plate format ID and name. |
| End the use case. | Commit the transaction. |

A Maintain Daughter Treatment Plates use case 1141 may be understood as follows. The automated system produces daughter treatment plates from master treatment plates. Each well in an assay plate has a specific dilution or other characteristic treatment from a well on a daughter treatment plate. See the Model Well Group use case 1121 for details on modeling groups of wells; see the Model Plate Format use case 1123 for details on mapping well groups to assay plates; and see the Maintain Assay Plate use case 1119 for details on combining a treatment plate with an assay plate to generate the wells on the assay plate.

The Track Daughter Treatment Plates use case lets one create and maintain daughter plates. A daughter plate can be generated based on a master plate (see the Track Master Treatment Plates use case 1139).

Exemplary processes of the Maintain Daughter Plates use case 1141 are depicted in Table 22 below.

TABLE 22

| Actor | System |
| --- | --- |
| Query a master treatment plate using its system identifier, its barcode, and/or its descriptive text. | Display the master treatment plate system identifier, barcodes, and description and the set of existing daughter treatment plates for the master and the set of wells for each daughter. |
| Create a set of daughter treatment plates, supplying the number of plates to create, the range of treatment plate barcodes and the media and treatment volumes added to the plates when creating them from the master. | Create the new plate in the Experimental Database and generate the set of treatment plate wells, setting the row, column, concentration, concentration unit, treatment volume, volume unit, and plate description from the master wells and the added media volume from input. |
| Select a treatment plate well on a master treatment plate. | Display the well information for the well, including row and column numbers; treatment ID, name, molecular mass, and molecular formula; compound concentration and volume; and plate description. |
| Select and change a daughter plate by changing the barcode or media volume for the plate. | Update the barcode or media volume in the Experimental Database. |
| Remove a daughter plate from active use. End the use case. | Mark the daughter plate as inactive. Commit the transaction. |

Experimental Protocol Design

The Experiment Protocol system is a LabRat application that lets a Designer create and maintain a set of experiment protocols. These protocols typically include one or more of the following aspects of an experiment design: a set of cell lines; a set of marker sets; a number of replicates; a list of time points; and a set of QC target sets.

These parameters, plus some additional specifications such as a set of master treatment plates, typically provides enough information to create a complete experiment layout. The protocol contains the general layout parameters; an experimenter chooses the protocol, then supplies the necessary specific information to create the experiment in an Experiment Wizard (described below).

Figure 12:
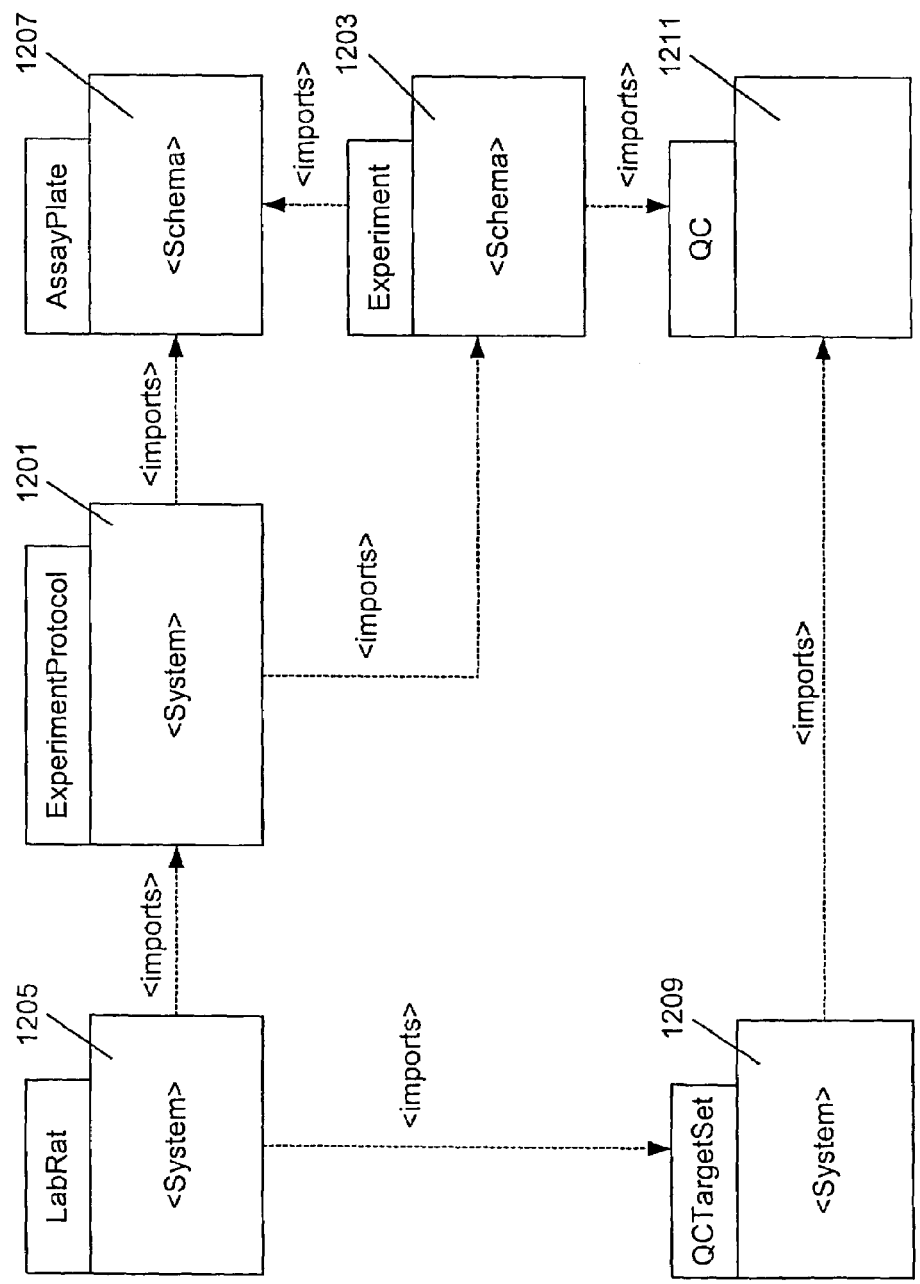
FIG. 12 presents a block diagram of an experimental protocol design architecture in accordance with an embodiment of this invention.

In one preferred embodiment as depicted in FIG. 12, the ExperimentProtocol system 1201 is a Java applet in the presentation layer that allows maintenance of persistent experiment protocols. The system 1205 (e.g., a Java Server Page) provides access to the ExperimentProtocol system 1201. In this example, the ExperimentProtocol system 1201 uses two subsystems in the business object layer (EJBs), AssayPlate 1207 and Experiment 1203. Both correspond to schemas in the database layer.

A QCTargetSet systsem 1209 may be a Java applet in the presentation layer that lets you maintain persistent QC target sets. The system (a JSP) provides access to a QC subpackage 1211 of the Experiment subsystem in the business object layer, consisting of EJBs and the underlying schema in the database server layer.

Experiment Wizard User Interface

The invention may include an "Experiment Wizard" system (e.g., a LabRat application) that lets a Production experimenter create an experiment quickly and easily. In a preferred embodiment, the Wizard provides one or more of the following parameters: (1) experiment protocol (specifies cell lines, marker sets, time points, number of replicates) (choose from list); (2) imaging protocol (choose from list); (3) QC target set (choose from list); (4) master treatment plates and plate format (enter series of barcodes and choose plate format for each from a list of compatible formats); (5) control master treatment plates (enter Taxol and DMSO or accept defaults); (6) daughter treatment plate barcodes (generated from specification or entered directly); and (7) cell plate barcodes (generated from specification or entered directly).

In the specific embodiment depicted in FIGS. 13A–13H, the Wizard uses the experiment protocol and the selected specific settings to create a complete experiment design. It creates the daughter plates and cell plates (including control plates). It allows the user to prune out particular plates not needed. It then lets the user choose an experiment model for each batch and generates the processes required for the batches. It produces a "Drug Add Worksheet" for each batch that tells the Experimenter how to process the batches through tissue culture and fluidics.

Figure 13A:
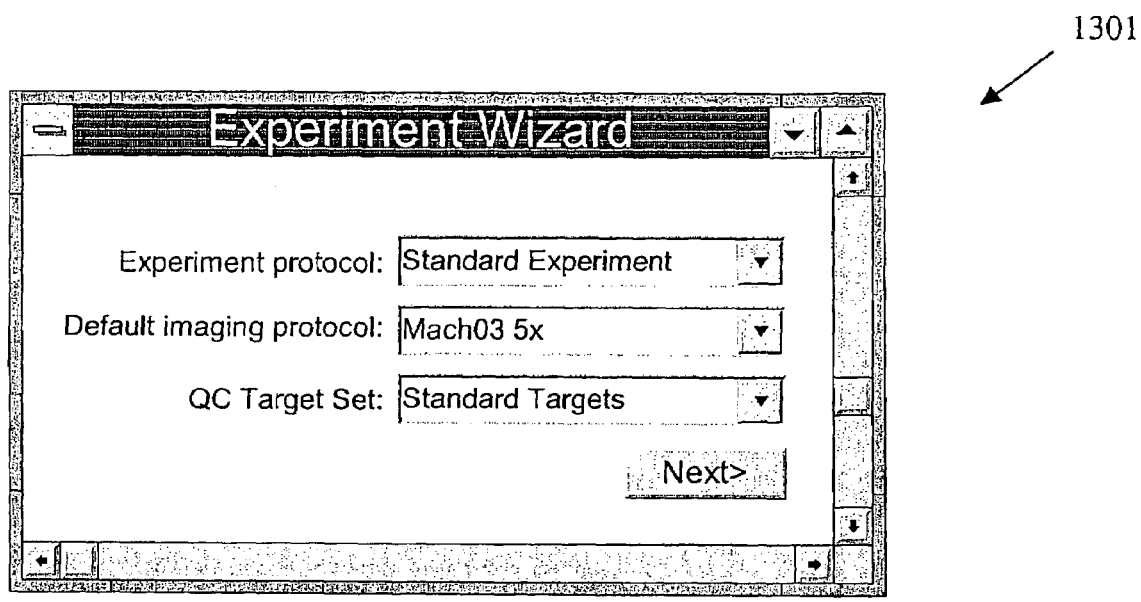
FIGS. 13A through 13H depict pages of an experiment wizard user interface that facilitate creation of a laboratory experiment in accordance with an embodiment of this invention.

As depicted in FIG. 13A, a first page 1301 of the wizard allows one to choose an experiment protocol, an imaging protocol, and a QC target set One can inspect or change all of these items through the automated laboratory experiment manager. The experiment protocol identifies an experiment setup, including a set of cell lines, a set of marker sets, a set of time points, and a number of replicates. A "Standard Experiment" might, for example, use six cell lines, OneStep and TriStain (three designated markers), a 24-hour time point, and 3 replicates. The imaging protocol sets the desired microscope and imaging parameters (this can be changed later in the Process Monitor). The QC target set is a set of features with upper and lower specification limits and a target value. The user can change the quality settings by creating multiple sets of QC targets, then creating the experiment with the appropriate set. The targets are associated with a particular experiment protocol, so the user sees only the target sets for the chosen protocol.

Figure 13B:
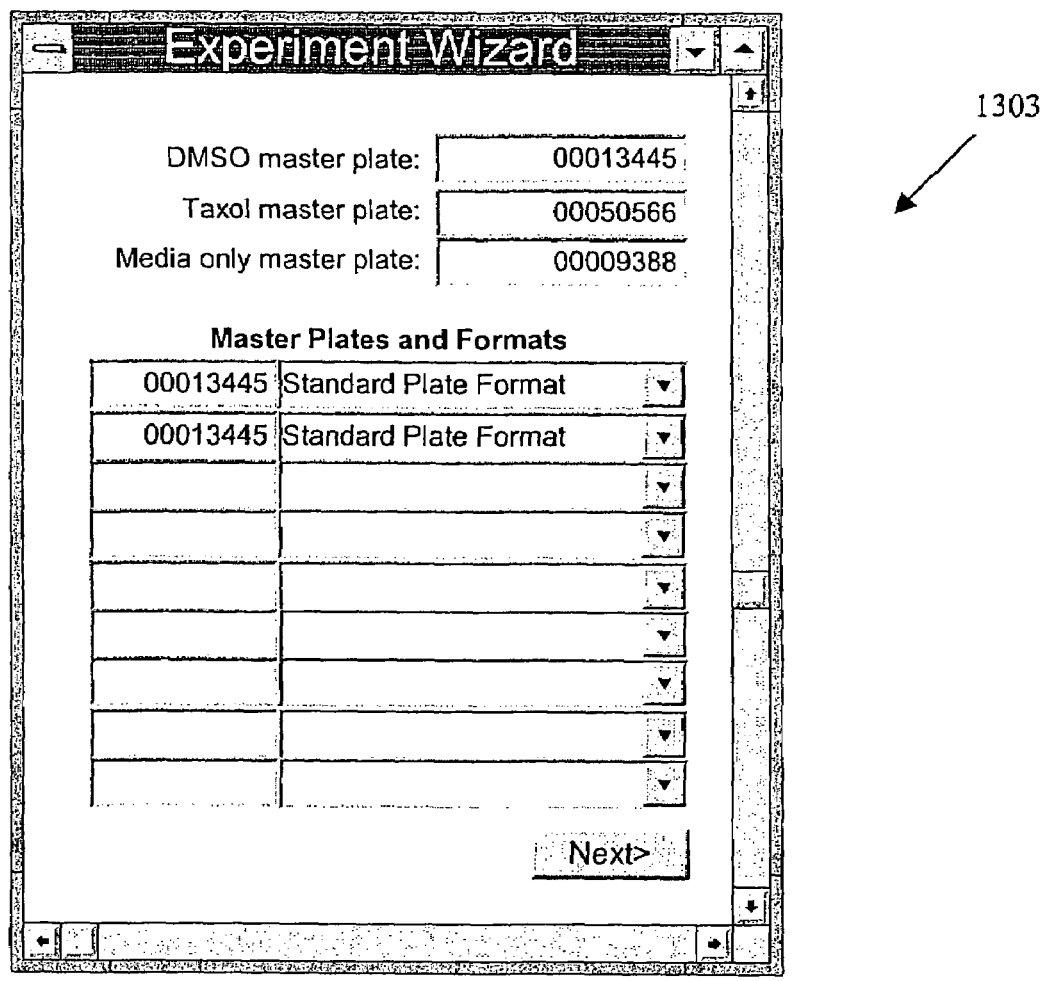

On a next page 1303 shown in FIG. 13B, the user may, in the depicted example, first choose the master treatment plates for DMSO, Media Only, and Taxol control plates. This page may display the "usual" master barcode to use for these by default, but the user can replace this barcode with another one if required. The user then chooses a series of master treatment plates by typing in a barcode. When the user enters a master plate barcode into the data entry field, the system restricts her choice of plate formats to the formats compatible with the master plate. She then chooses one plate format from the dropdown list of compatible plate formats. A "compatible" plate format is one with a set of well group wells that matches in number the set of master plate wells.

Figure 13C:
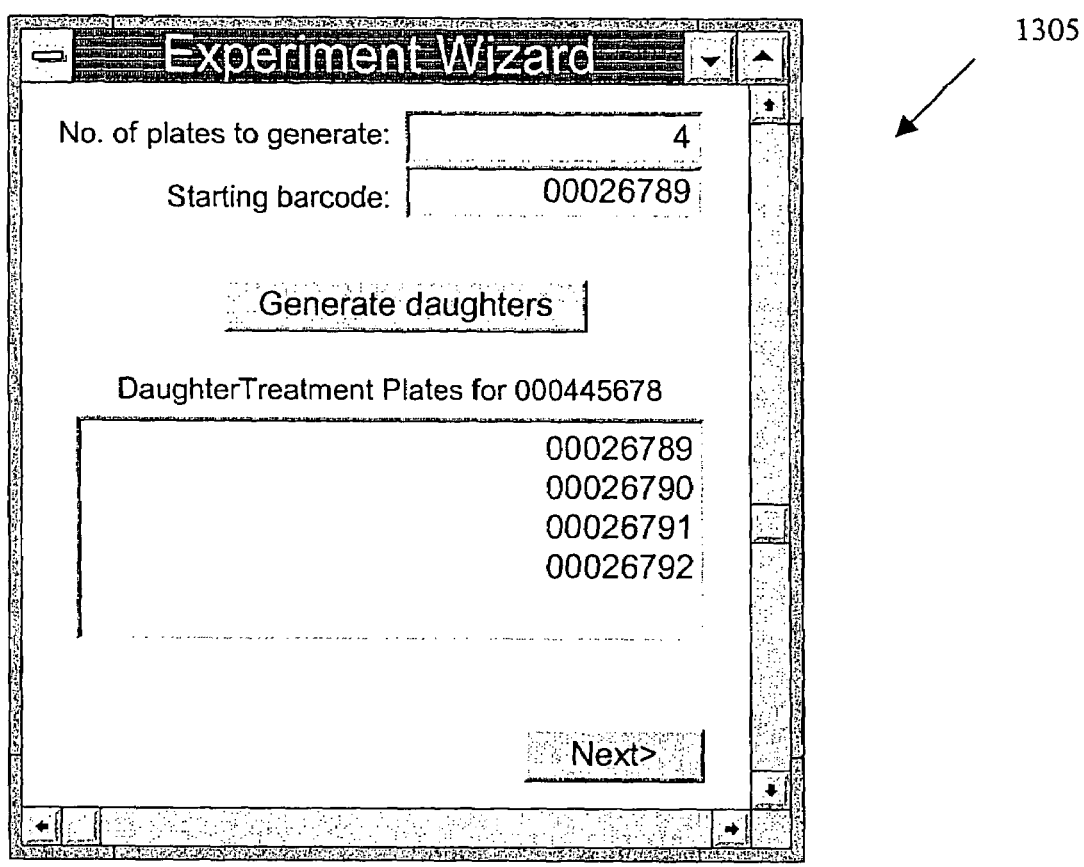

As shown in FIG. 13C, a next page 1305 lets the user choose a starting barcode to use for daughter treatment plates for a selected master barcode as well as specifying a number of such plates to generate. Alternatively, the user can type in a list of daughter barcodes directly into the list of plates. A special case is using the master plate as a daughter: the user does this by entering the master barcode as the starting barcode and setting the number of daughters to 1. On clicking the "Generate daughters" button, the Wizard generates the required number of daughter plates using the TreatmentPlateGenerator session bean. Each generated plate will have a unique barcode incremented by one from the previous barcode, with the first plate having the starting barcode. In alternative embodiments, it is possible to generate daughter plates automatically based on the number of assay plates required.

Figure 13D:
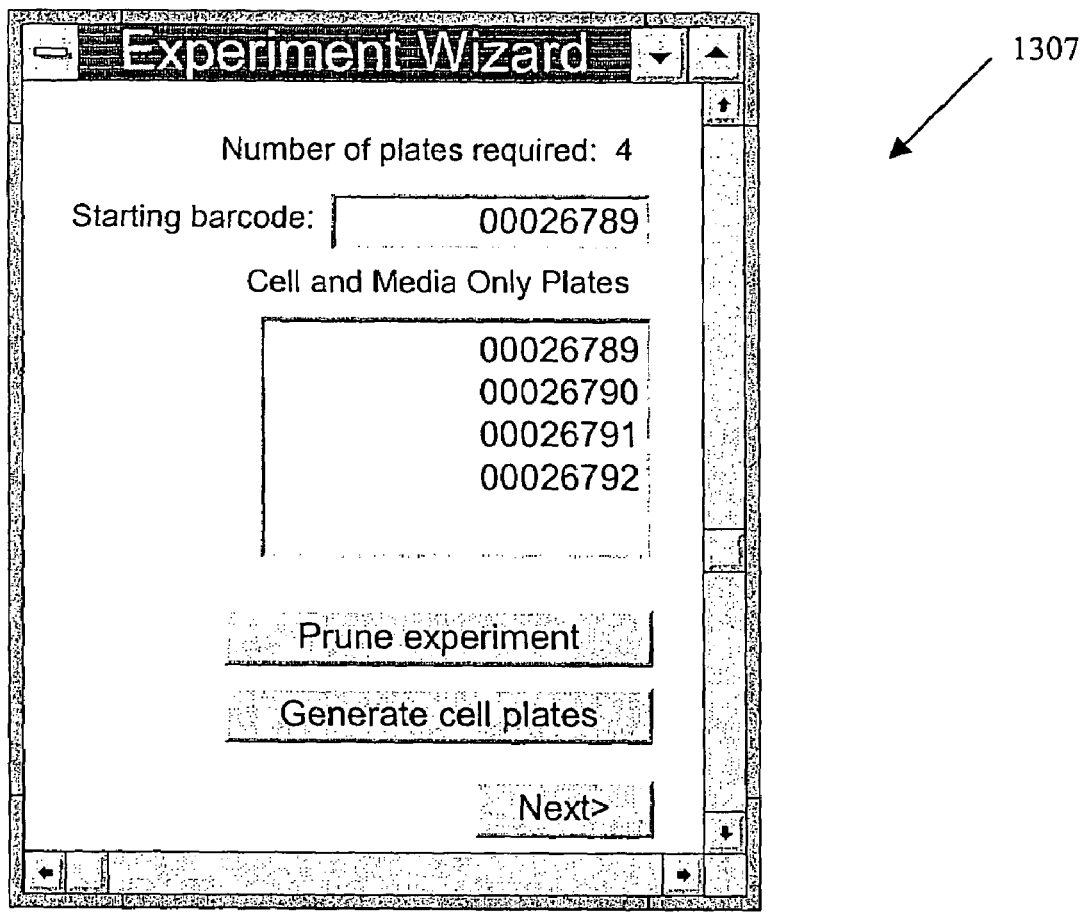

As shown in FIG. 13D, a next page 1307 displays the number of plates required at this point in the Wizard. It lets the user enter the starting barcode to use for the assay plates generated by the design. In one embodiment, each plate will have a unique barcode incremented by one from the previous barcode, with the first plate having the starting barcode. Alternatively, the user can just type in the barcodes into the text box, which lets her enter a list of non-sequential barcodes. Clicking on "Prune experiment" lets her remove certain branches of the experiment tree (see the following explanation). Clicking on "Generate cell plates" lets her see the list of generated cell plates; clicking on "Next>" finalizes the list of cell plates.

Figure 13E:
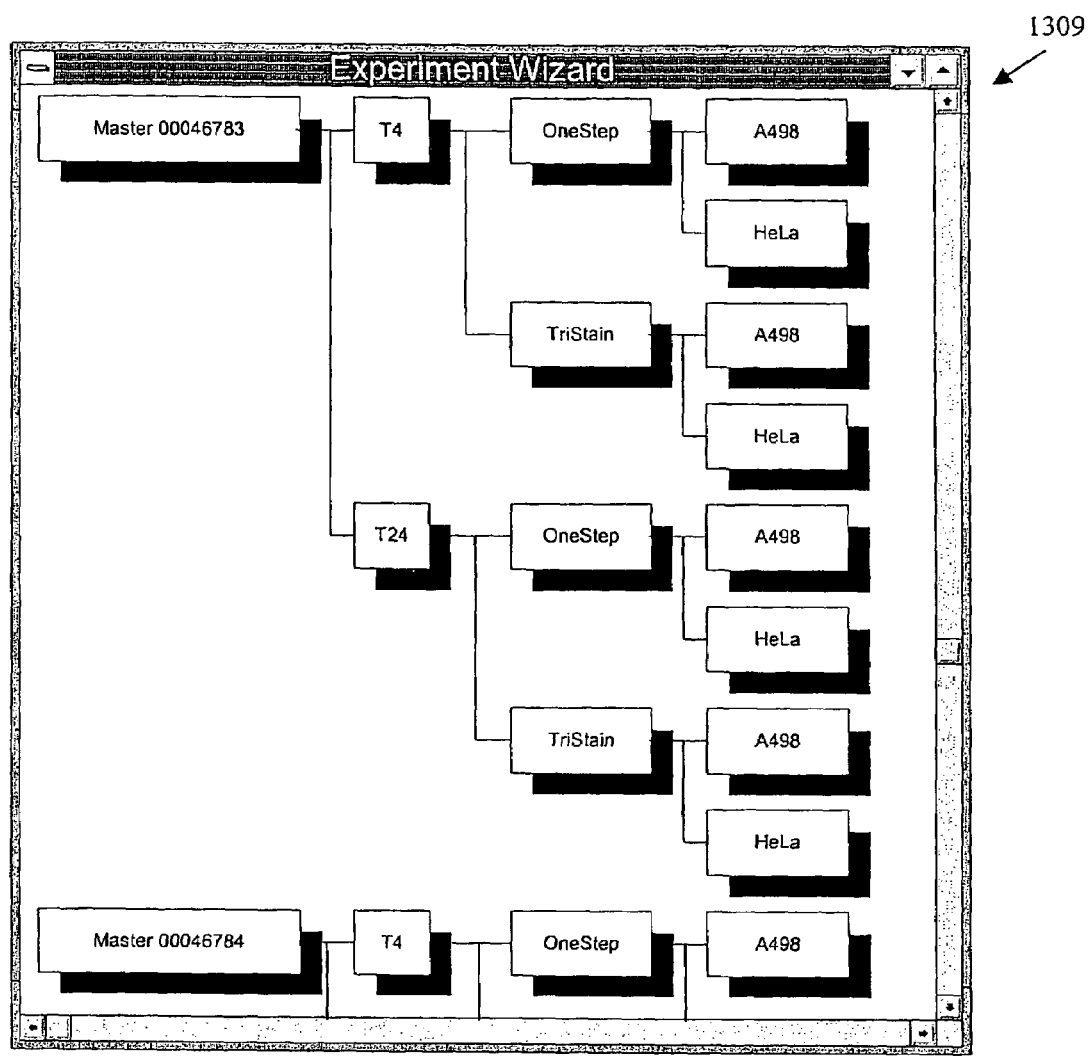

An ExperimentPruner applet gives the user a way to prune branches from an experiment. As shown in FIG. 13E, the system presents a tree 1309 of the combinations of the experiment parameters (master treatment plate, time point, is marker set, and cell line, in that order). The user can prune out whatever branches of this tree are not required for the experiment.

Figure 13F:
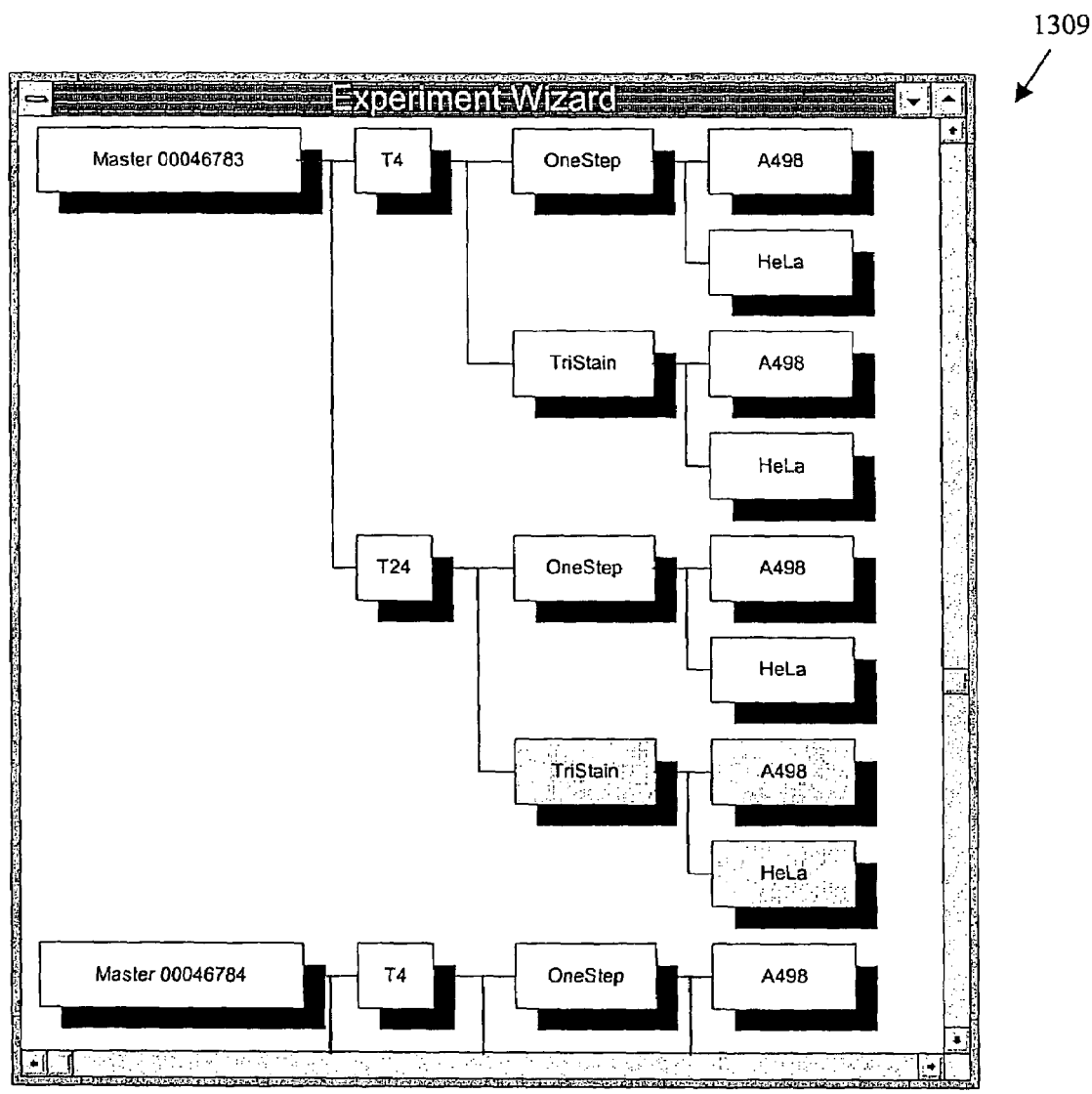
Figure 13G:
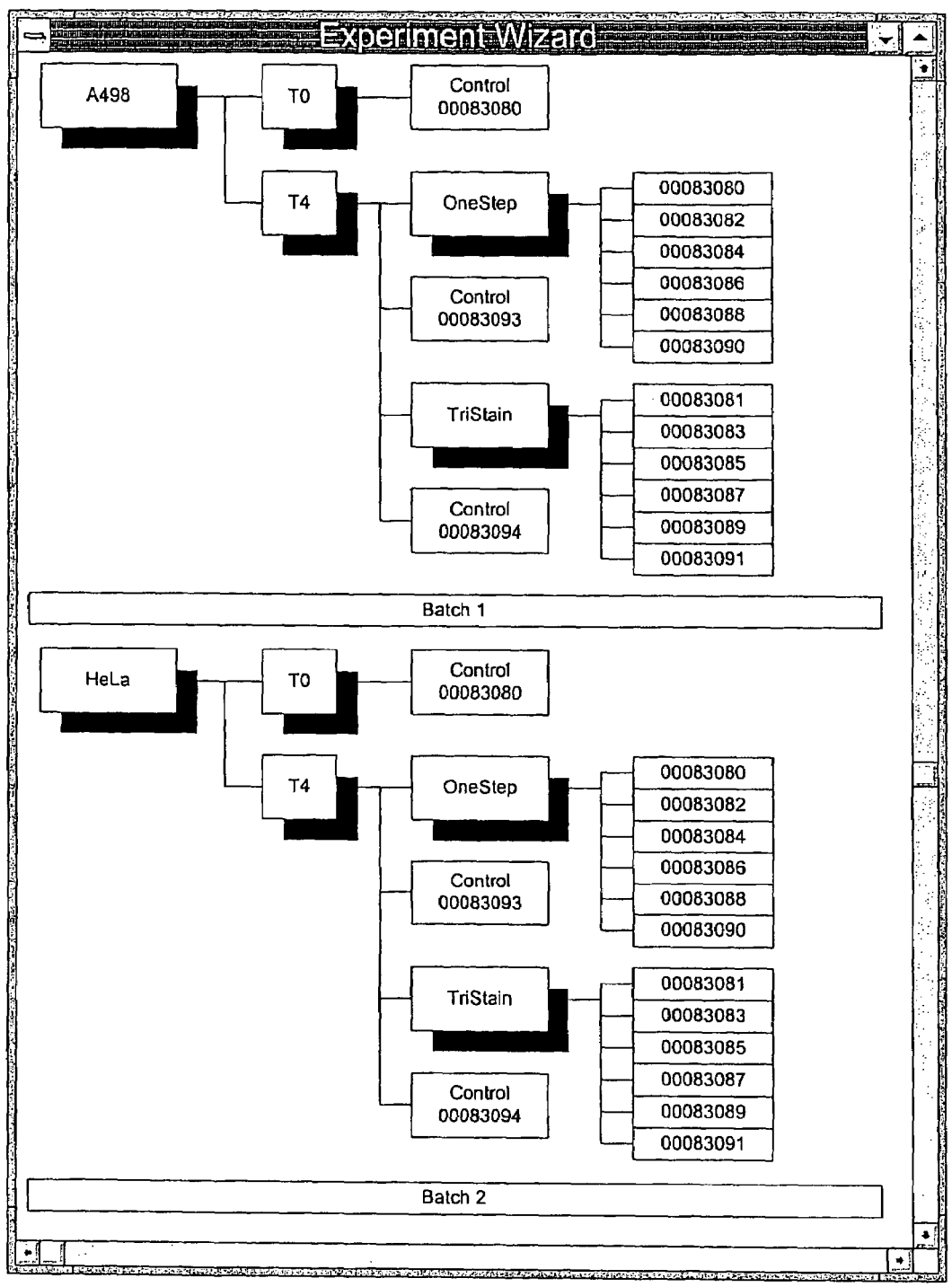
Figure 13H:
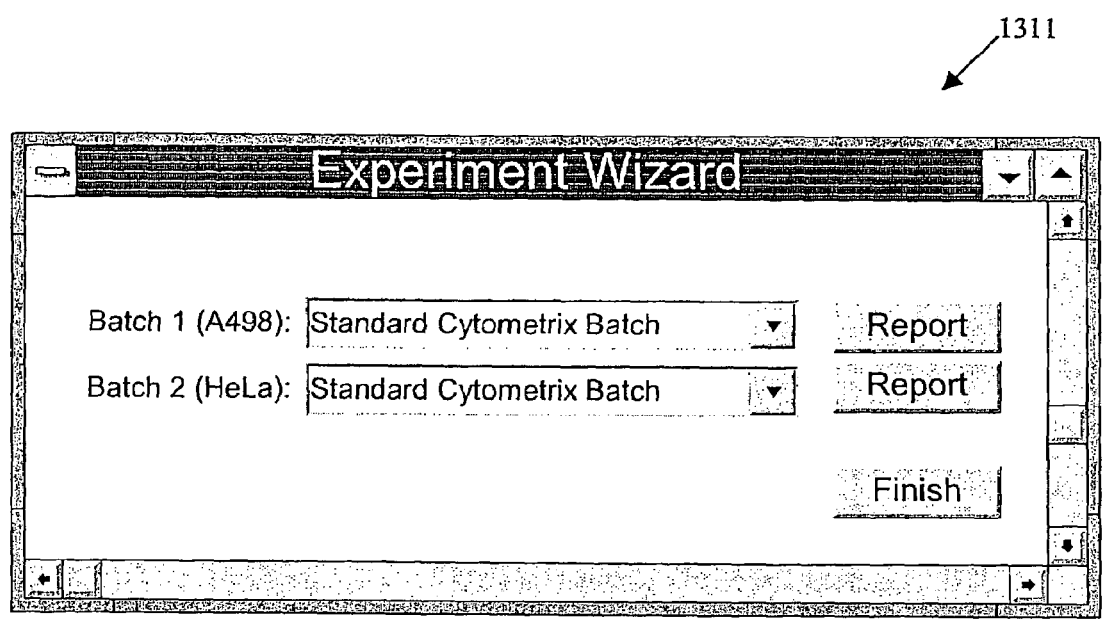

In the depicted example, there are two cell lines, two marker sets, and two time points. The Experimenter determines that one marker set is unnecessary at one time point, so he or she prunes that marker set from that time point branch, removing those plates from the experiment as shown in FIG. 13F.

After saving and exiting from the applet, the system displays the Cell Plates form, and the user can click on the "Generate cell plates" button, and then click on next to see the Batch Generator applet.

The Batch Generator lets the user divide an experiment into batches. The system displays the remaining tree branches divided into batches, one per cell line. See FIG. 13G. It then lets the user combine these branches to merge several cell lines into a single branch corresponding to a single batch.

The user can also label the batches with a name so she can easily understand which is which in the next Wizard screen.

When the user exits the Batch Generator applet after saving, she sees a final page 1311. See FIG. 13H. Here, she generates the experiment by associating experiment models with each batch.

Clicking on Report for a batch gives the user an Drug Add Worksheet for that batch. Clicking on Finish runs the process generator. If there are sub-experiments, the generator will prompt the user to enter subsets of plates where required.

Passaging

Passaging, or splitting, is a process used to grow cells continuously in media Cytometrix™ experiments may require a significant quantity of a commercial cell line (a particular kind of cell, such as A549 or HUVEC). Cytometrix™ has qualified several cell lines for use with experiments and has a database with target cell counts and quality specifications for each cell line. Passaging lets one grow cells from the commercial lot.

A group within an organization typically has the responsibility of maintaining and growing the cells to supply experiments with microtiter plates with cells of a certain density within a certain maximum passage number. Research associates grow the cells in, e.g., T-175 flasks or roller bottles; when the cells reach a certain confluence (coverage of the surface area of the flask) the tissue culture research associate passages the cells and either puts them into new vessels or plates them onto microtiter plates. The passaging allows the cells to grow by reducing their confluence to a level that will promote growth.

The density of cells in the wells of the plate is typically an important process variable for the automated system. If plating density is not within specification limits or diverges widely from its target, the image processing and biological analysis algorithms can fail.

Passaging involves trypsinizing the cells (applying the chemical trypsin) in the flask to disrupt their adherence to the flask, combining flasks into a single cell suspension, counting the resulting cells, then either putting the cell suspension into a new set of flasks at the right density or plating the cells onto microtiter plates with the Multidrop device for an experiment (or both). This process adds one more passage number to the cell line. For example, the cells are said to go from passage 3 to passage 4 after trypsinization.

Figure 14A:
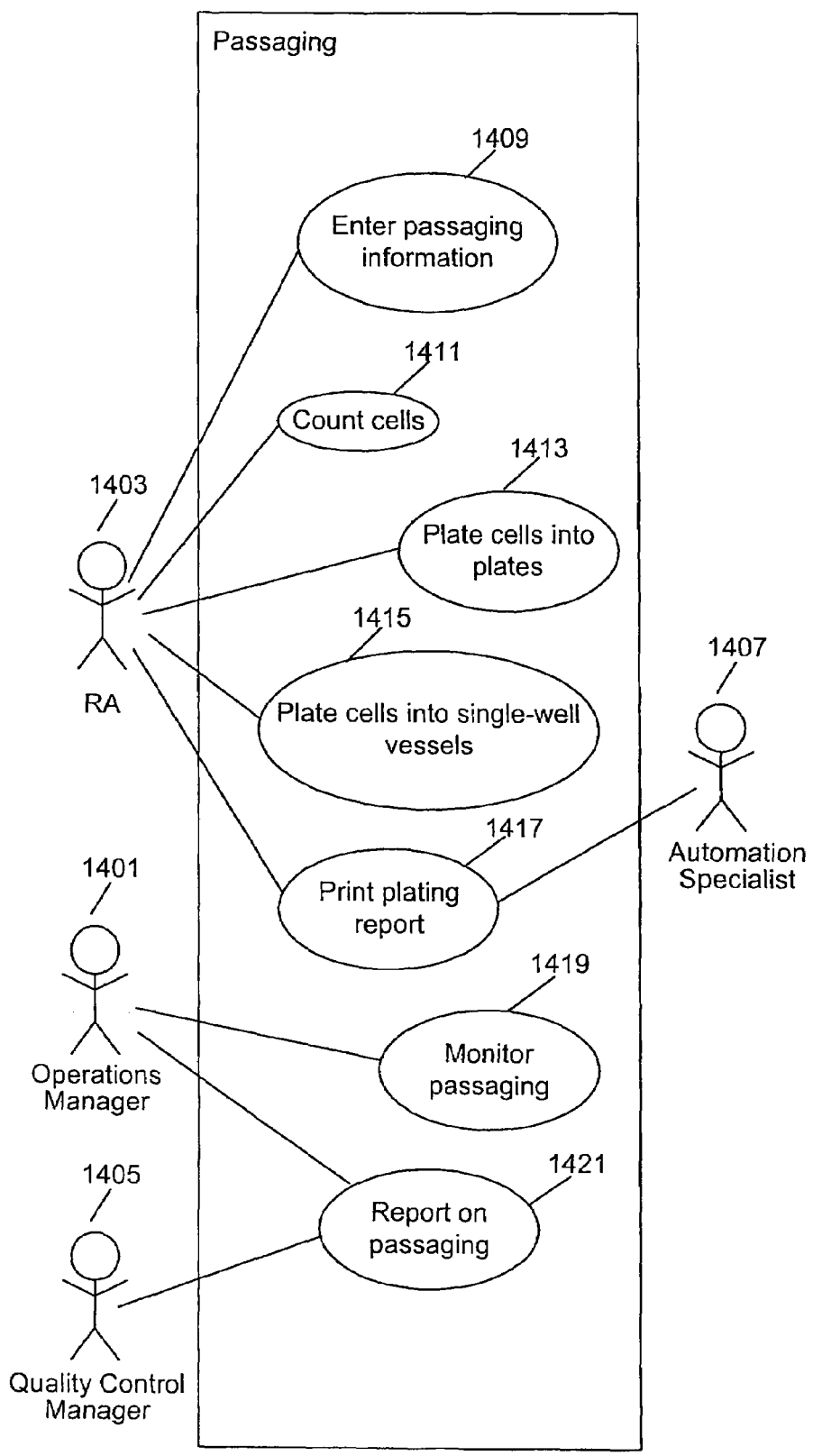
FIG. 14A presents a context diagram illustrating various use cases associated with passaging to grow cells continuously in media.

Various actors participate in the passaging use cases shown in FIG. 14A. The primary actor is a Research Associate 1403, who is the main user of the application. The Research Associate 1403 enters various pieces of information during the processes and uses the computed information delivered through the application to complete the processes. The RA 1403 is responsible for correct data entry and for using the computed information properly by applying the tissue culture SOPs (standard operating procedures). A secondary actor is an Operations Manager 1401, who monitors cell-plating processes and inspects the tissue culture worksheet information. Another secondary actor is a Quality Control Manager 1405, who inspects the tissue culture worksheet information to improve process quality. The Operations Manager 1401 inherits all the abilities of the Research Associate 1403, allowing him or her to enter data and use results. Another secondary actor is an Automation Specialist 1407, who uses the passaging report.

Generally, the Operations Manager 1401 is responsible for the system's tissue culture. She should be able to understand what is happening in the tissue culture passaging and cell plating processes, enter passaging information, count cells, plate cells into plates, plate cells into single-well vessels, monitor passaging, and report on passaging. She should also be able to trace what happened in passaging and cell plating when there is a plating density failure.

The Research Associate 1403 is generally responsible for laboratory work during the tissue culture processes. She should be able to get correct values for required process values based on minimal inputs, enter passaging information, count cells, plate cells into plates, and plate cells into single-well vessels.

The Automation Specialist 1407 is generally responsible for laboratory work during the drug add processes. She should be able to verify that a set of plates have a particular cell line on them before proceeding with a drug-add process and print plating report.

An Enter Passaging Information use case 1409 can be understood as follows. The RA 1403 creates a new passaging task by entering information about the passaging process. The system calculates the total number of milliliters of cell suspension that will be available for plating into the target number of vessels at the end of the passaging process as well as various other target values.

Passaging takes a set of input vessels containing cells and plates the contents into some combination of output vessels. For example, one kind of passaging takes roller bottles as inputs and produces roller bottles as output. Another kind of passaging takes T-175 flasks as inputs and produces a combination of 386-well plates and T-175 flasks. The plates go on to become part of an experiment; the flasks go back into the next passaging task for further growth of the cells. The input vessels should all be of the same type and plating volume and should contain cells with the same passage number. There are three types of passaging:

Maintenance: The RA is maintaining the cell line with no intention of plating the cells within one passage of the current passaging. That is, the cells are going into another flask with the intention of repeating the process at least once into another, additional flask.

Pre-plating: The RA is preparing the cells for plating with one additional passaging before the plating occurs. That is, the cells are going into another flask with the intention of passaging them into a set of plates on the next passage.

Plating: The RA is passaging the cells for plating onto plates in the current process. The RA may passage some of the cells into flasks as for maintenance or pre-plating while plating some of the cells onto plates.

Note that this use case narrative refers to wells. Generally, a "well" is a receptacle or set of receptacles in a vessel. A flask, for example, has one well (itself), as does a roller bottle. An 8×12 plate has 96 wells, and a 16×24 plate has 384 wells. An output plate may use only some of the available wells; hence the RA can specify how many wells to output per vessel, which allows for correct calculation of required volume amounts. The Scientist can specify a default number of wells to plate for each kind of plate.

The Enter Passaging Information use case 1409 sequence may generally proceed as follows. The RA logs on to the system. The system displays a new passaging task with the name of the logged-on RA's name and the current date and time. The RA sets the name of the RA responsible for the passaging, replacing the logged-on RA's name. The RA sets the cell line from the list of available cell lines. The RA sets the number of input vessels. The RA selects the vessel type, plating volume, and plating type (Maintenance, Pre-Plating, or Plating) (one field, all items together from the list of supported vessels, volumes, and types for the cell line). The RA enters the starting passage number from the input vessel labels. The RA estimates the confluency of the cells in the flask and enters the confluency as a percentage (5, 10, 15, 20, 25, 30, 35, 40, . . . , 95, 100). The RA takes digital images of each input flask and stores them on disk in a network storage directory. The RA selects one image to represent the confluency estimate and enters its path and filename. The RA enters the media working number that identifies the media lot being used The RA enters the trypsin aliquot number that identifies the trypsin lot being used The RA enters the PBS aliquot number that identifies the PBS lot being used. The RA saves the passaging task The system stores the passaging task in the database. The name is the name of the cell line plus the date plus the starting passage number: 'A498 6/23/2001 09:05:27 Passage 17', for example. The system sets the task status to Started. The start date is set to the current date and time.

A Count Cells use case 1411 may be understood as follows. The RA 1403 counts the cells after trypsinizing the flask. In a specific example, the RA takes three counts with the Coulter counter device and the system calculates the average. The RA counts the cells with a hemocytometer to check the Coulter counter number. The system calculates the average number of cells per milliliter and the total number of cells available.

A goal of this use case is to track cell counts going into passaging and to provide estimates to the RA of the current count and density in the flasks. In a particular example, it involves specifying a number of T-175 flasks (nT175) and a total number of milliliters of cell suspension (totalSuspension)

The average cells per milliliter can be calculated as follows.

average cells per ml=average cell count/cell suspension volume (mls)

where average cell count=(hemocytometer count+ coulter 1+coulter 2+coulter 3)/4 cell suspension volume=number of vessels*resuspension volume per vessel (mls)

resuspension volume per vessel=resuspension volume per well (mls)*number of wells per vessel Then the total cells available may be calculated as follows.

total cells available=number of vessels*cell suspension volume (mls)*average cells per ml A simple Count Cells use case 1411 narrative follows. The RA enters 3 Coulter Counter cell counts. The system calculates the average count and displays it once; the RA enters all 3 values. The RA enters a hemocytometer count for four squares. The system displays two calculated values: average cells per milliliter and total number of cells available (see calculation formulas above). The RA saves the cell counts. The system stores the counts in the database along with the date and time of the last count entered.

A plate cells into plates use case 1413 may be understood as follows. When one or more experiments are pending, the RA should create some number of cell plates from the cell suspension. The RA enters the number of plates to process, then runs the plates through the "Multidrop" device to plate the cells. The RA reads the barcode for each plate with a barcode reader. For each plate, the system creates an assay plate object in the database with the cell line and passage number (plus one) from the worksheet. The system also creates a completed Plating Task for all plates processed, associating all plates with the task as process elements, allowing the Process Monitor to display the status of plating to the Operations Manager.

Note that the use case assumes there is one set of output plates, all of which are the same type. The barcode reading operation happens after a Multidrop plating process is complete. The RA takes the stack of plates over to the bench and scans all the barcodes into the worksheet. Because this is a single-point event, there is only one task for all the plates, and the date and time for task start and complete is the barcoding start and complete time. This is easier than scanning the barcodes directly; assuming that the individual times are not important.

The total media required may be calculated as follows.

total media needed=number of vessels*plating volume (mls per vessel)+dead volume (mls)

where number of vessels is entered by the RA, dead volume is from the Vessel table, and plating volume is calculated from the plating volume per well as follows.

plating volume (mls per vessel)=plating volume (mls per well)*number of wells

The total cells required may be calculated as follows.

total cells needed=target diluted cells per ml*total media needed (Mls)

where total media needed (mls) comes from the previous calculation and target diluted cells per well ml is calculated from the Cell Line Vessel Profile target diluted cells per well entered by a Scientist.

target diluted cells per ml=target diluted cells per well/plating volume (mls per well)

The concentrated cell stock may be calculated as follows.

concentrated cell stock (mls)=total cells needed/average cells per ml where total cells needed is calculated above and average cells per ml comes from the average cell count:

average cell count=(hemocytometerCount+ coulter 1+coulter2+coulter3)/4)

average cells per ml=average cell count/cell suspension volume (mls)

where the counts come from the "Count cells" use case and the cell suspension volume (mls) comes from the calculation:

number of vessels*number of wells*resuspension volume mls per well where number of vessels is the number of output plates, number of wells is the number of wells to plate (not the number of wells on the plate, necessarily), and resuspension volume comes from the Cell Line Vessel Profile. If total cells needed is greater than the total cells available from the "Count cells" use case, the plating has failed.

An example Plate cells into plate use case narrative follows. The RA chooses the plate type, plating volume, and passaging type (Plating in this case, all items in one field), the number of plates, and the number of wells to plate in each vessel (default). The system displays the total media needed, the total cells needed, and the amount of concentrated cell stock to add (mls) for this set of plates. The system also displays the total cells needed for the passaging task (sum of all output vessels including this set of plates) and calculates whether the plating has failed (that is, whether there are enough cells available to accommodate the number of plates and other vessels entered as output in this use case or the "Plate cells into single-well vessels" use case). See the above calculations. The RA enters 3 Coulter Counter cell counts. The system calculates the average before-plating count and displays it once the RA enters all 3 values. The RA plates the cells using the Multidrop device. After completing the plating, the RA scans the plate barcodes into the Passaging Worksheet. For each plate, the system creates a plate object with the barcode and sets the cell line (cellLineID) and passage number (starting passage number plus 1). The system displays the number of plates processed. The step ends when the system increments the number of plates processed to a value that is equal to the number of plates to process that the RA entered in step 1. At this point the RA cannot process any more plates. The RA enters 3 Coulter Counter cell counts. The system calculates the average after-plating count and displays it once the RA enters all 3 values. The RA enters a comment on the plating process. The system logs the comment and attaches it to the passaging process associated with the plating. The RA ends the use case, saving the changes. The system sets the completion date of the passaging task to the current date and time.

A Plate cells into single-wells vessels use case 1415 may be understood as follows. The goal of this use case is to track the transfer of cells into different single-well vessels as part of the passaging process (maintenance, pre-plating, or along with plating). As a precondition, the cell line seed density settings are entered in Cell Line Vessel Profile as target concentrated cells for maintenance and pre-plating plating types. An average number of cells per milliliter is calculated in "Count cells." After trypsinization, the RA 1403 needs to transfer the cell suspension (less the amount plated on 384-well plates) into new single-well vessels, either as maintenance or as a pre-plating passaging.

The narrative for use case 1415 follows. The RA chooses the plate type, plating volume, and passaging type (all items in one field), and the number of vessels. The system displays the total media needed, the concentrated cell stock needed, and the total cells needed for this set of vessels (based on the passaging type, plating volume, and cell target). The system also displays the total cells needed for the passaging task (sum of all output vessels including this set of vessels and possibly a set of plates) and calculates whether the plating has failed (that is, whether there are enough cells available to accommodate the number of vessels entered as output in this use case or the "Plate cells into plates" use case). See the discussion in the "Plate cells into plates" use case 1413 for the calculations. The RA enters a comment on the passaging process. The system logs the comment and attaches it to the passaging process associated with the plating (see the "Enter passaging information" use case). The RA ends the use case, saving the changes. The system sets the completion date of the passaging task to the current date and time.

After completing plating, the RA may print a report listing the cell line, the date and time of passaging, and the list of barcodes of the plates made by the passaging task. This is represented by a Print plating report use case 1417. One goal of use case 1417 is to provide the automation Specialist with a hard-copy record of the set of plates and their cell line for use during incubation and drug add tasks. The Automation specialist uses the printed report to ensure that the plates are the right ones given the experiment design. During the use case 1417, the RA chooses to print the plating report. The system sends a report giving the cell line, the passaging task completion date and time, and a list of cell plate barcodes plated by the passaging task.

A Monitor passaging use case 1419 may be understood as follows. Its goal is to display the status of a passaging process to the Operations Manager 1401. Generally, the "Plate cells into plates" use case or the "Plate cells into single-well vessels" use case must be in progress or completed to see the tasks.

The Operations Manager uses the Process Monitor to see the status of plating tasks. When an RA saves passaging information, the Process Monitor displays the Passaging task. The status appears first as Started, then changes to Completed when the RA saves the plating information.

During the use case 1419, the system displays all passaging tasks, displaying the name, description, start date, completion date, and status for the task The system then refreshes the monitor display, getting any new processes and tasks. If appropriate, the Operations Manager sets the status of a Started task or process to Broken, stopping any further processing of the task. If appropriate, the Operations Manager sets the status of a Broken task or process to Started, allowing further work on the plating tasks. In some embodiments, the Process Monitor may log an application failure and displays the error, then offer the Operations Manager the choice of continuing or closing the monitor.

A Report on passaging use case 1421 may be understood as follows. Its goal is to give the Operations Manager 1401 and Quality Control Manager 1405 all the information about the passaging tasks that have taken place during a specific time period. One of the managers runs the report.

During the use case 1421, the Operations Manager 1401 specifies the cell line, starting timestamp and ending timestamp to define the reporting period. The system then displays the report, showing for each Passaging task with a start date within the specified time interval the process name, description, RA, cell line name, start date, end date, input vessels and their image, confluency, starting and ending passage numbers, media working number, trypsin batch, PBS batch, hemocytometer cell count, average Coulter counter cell count, average before-plating cell count, number of output plates made, average after-plating cell count, and number of output single-well vessels made. The system calculates and displays the status of passage failure and plating failure for each task. The system also displays any comment (with last status date and owner person) linked to the task and any failures (with last status date and owner person) logged against the task.

A tissue culture user interface suitable for use with this invention is constrained only by the need to represent certain data. In one embodiment, FIGS. 14B and 14C show the suitable spreadsheets for T-175 flask and 384-well plating.

There are two tables, one in each spreadsheet, that describe the characteristics of the cell lines. There are some fields mentioned in the passaging use cases that do not appear on these spreadsheets, such as the count of actual plates processed and the comment fields.

Note the emphasis placed on the cell line name display and on the counts, which are in large boxes. Generally, a passaging worksheet should find a way to emphasize these items as important. The UI should typically provide a Save feature and a New Passage feature. It might also provide an End Passage feature to enable ending the 384-well plating use case without actually creating a new passage.

The Passaging Task contains a confluency estimate and an image file of the confluency sample, the starting passage number, the identifiers for the input reagents, various cell counts, and the date and time of cell counting. Methods on this class calculate count averages, total cells available for passaging, total cells needed for passaging, whether the passaging and/or plating failed, and the cell line for the passaging (all vessels should have the same cell line, and there is no direct link to the cell line table, hence the method).

An InputVessels table is a set of vessels that provide cells to the passaging task. The class has the number of vessels in the set and calculates the cell suspension volume in mls. There is exactly one set of input vessels. The OutputVessels table is a set of vessels that hold the passaged cells, and there can be any number of such sets (usually 2, a set of plates and a set of single-well vessels). The class specifies the number of vessels and the number of wells in each vessel actually used. The class provides methods to calculate the total amount of media (mls) required for the output vessels, the total cells needed, and the amount of concentrated cell stock needed for the vessels (mls).

Treatment Plate Generator Design

The automate system produces daughter treatment plates from master treatment plates. Each well in an assay plate has a specific dilution of a treatment from a well on a daughter treatment plate.

A Track Daughter Treatment Plates use case lets a user create and maintain daughter plates. The user generates a daughter plate based on a master plate.

Some relevant processes are depicted in Table 23 below.

TABLE 23

| Actor | System |
| --- | --- |
| Query a master treatment plate using its system identifier, its barcode, and/or its descriptive text. | Display the master treatment plate system identifier, barcodes, and description and the set of existing daughter treatment plates for the master and the set of wells for each daughter. |
| Create a set of daughter treatment plates, supplying the number of plates to create, the range of treatment plate barcodes and the media volume added to the plates when creating them from the master, | Create the new plate in the Experimental Database and generate the set of treatment plate wells, setting the row, column, concentration, concentration unit, treatment volume, volume unit, and plate description from the master wells and the added media volume from input. |
| Select a treatment plate well on a master treatment plate. | Display the well information for the well, including row and column numbers; treatment ID, name, molecular mass, and molecular formula; compound concentration and volume; and plate description. |
| Select and change a daughter plate by changing the barcode or media volume for the plate. | Update the barcode or media volume in the Experimental Database. |
| Remove a daughter plate from active use. | Mark the daughter plate as inactive. |
| End the use case. | Commit the transaction. |

Figure 15A:
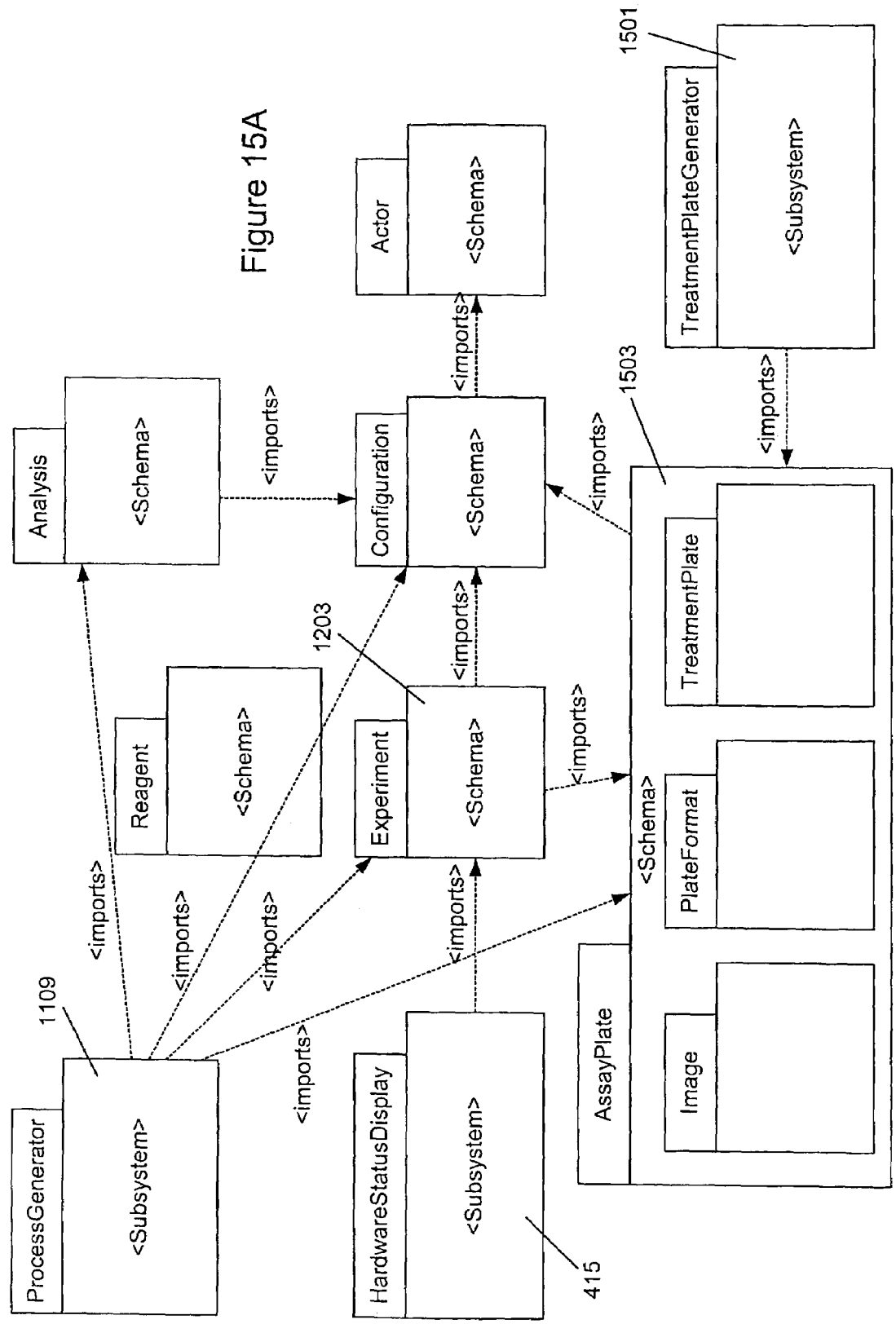
FIG. 15A depicts a block diagram associated with a treatment plate generator in accordance with an embodiment of this invention.

In a preferred embodiment a Treatment Plate Generator 1501 is a form and a stored procedure that uses the Assay Plate schema 1503 and the ActivityBase integration to generate daughter treatment plate records in the Assay Plate schema as illustrated in FIG. 15A.

In a specific embodiment, a Treatment Plate package contains most of the relevant persistent classes that the application uses. A Master Treatment Plate class is a view on the ActivityBase tables that represent treatments and plates. It contains a barcode, a description, and an ActivityBase plate format. A Treatment Plate class represents a daughter treatment plate, a plate onto which one transfers some of the volume of treatments from the master treatment plate. It has a unique treatmentID (the implicit OID), a separate barcode, and the volume of media added to each well on the plate when the plate is set up. This volume is part of the ultimate calculation of the concentration of treatment compound in the daughter treatment plate well.

A Treatment Plate Well class represents a single well on the daughter treatment plate, and each well links to the corresponding well on the master treatment plate. All treatment plate wells have a treatment compound, empty wells do not exist in the Treatment Plate Well table. The class contains the row and column number that map to the master well, a concentration and concentration unit taken from the master well (so that there is no need to join to the view, a considerable performance problem), and a volume of treatment compound added to the treatment plate well. This will usually be the same volume for all wells on the plate, an assumption that the Treatment Plate Generator uses in generating the daughter plates.

Plate generation also requires the addition of a plate format tied to the master plate. The Treatment Plate Generator lets the user attach a plate format and checks to ensure the plate format is compatible with the ActivityBase plate layout.

The Plate Format has a plate type (8×12 or 96 wells versus 16×24 or 384 wells) and a group of well groups. A well group identifies a set of generic wells that will either be controls or will contain a single treatment (or possibly some other designation as time goes on). Each well in a well group has a row and column number to identify the well within the group (and to link the well to wells on treatment and assay plates).

The Treatment Plate Generator checks to make sure the basic plate type is compatible with the ActivityBase master plate format. It also checks to make sure the well group wells correspond to non-empty wells in the Master Treatment Plate Well table.

Figure 15B:
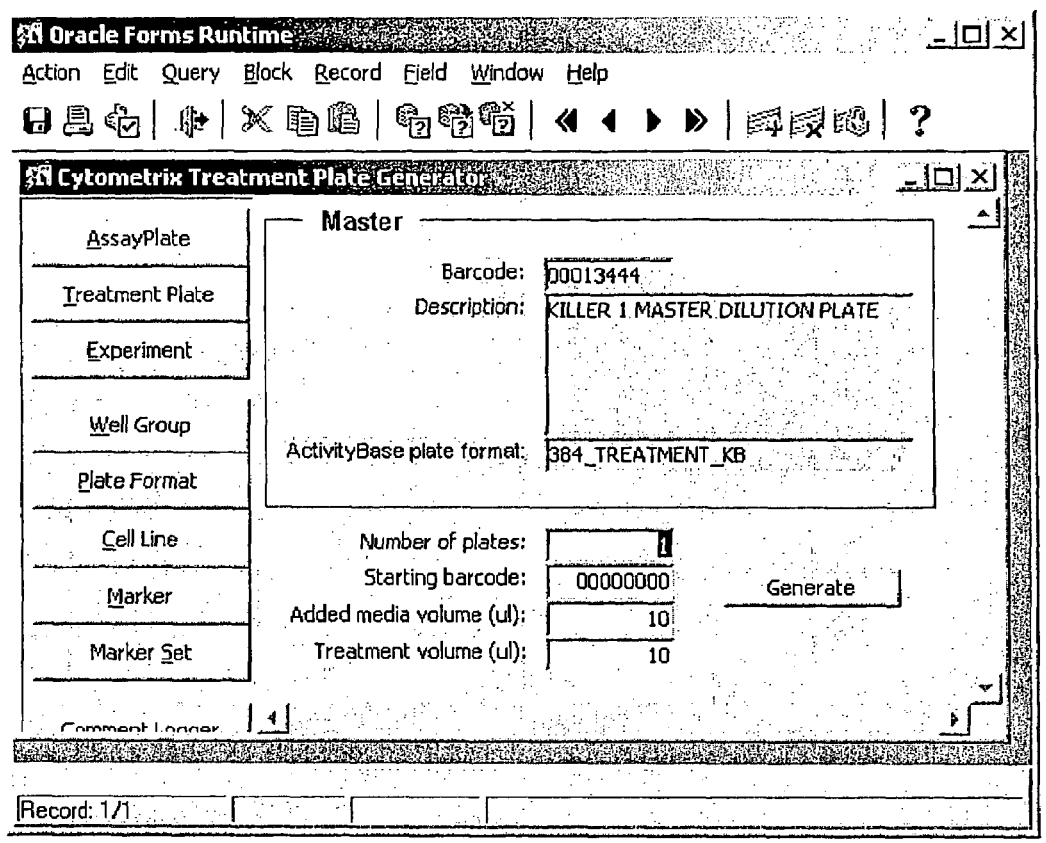
FIG. 15B shows a sample user interface page for a treatment plate generator.

A sample user interface for the treatment plate generator is a single form as depicted in FIG. 15B.

The top block lets the user query any master treatment plate from ActivityBase. The lower block lets the user specify the number of plates to generate, the starting barcode, the volume of media to add to each well on each plate, and the volume of treatment to add to each well on each plate. When the user clicks on the Generate button, the application generates the plates.

Figure 15C:
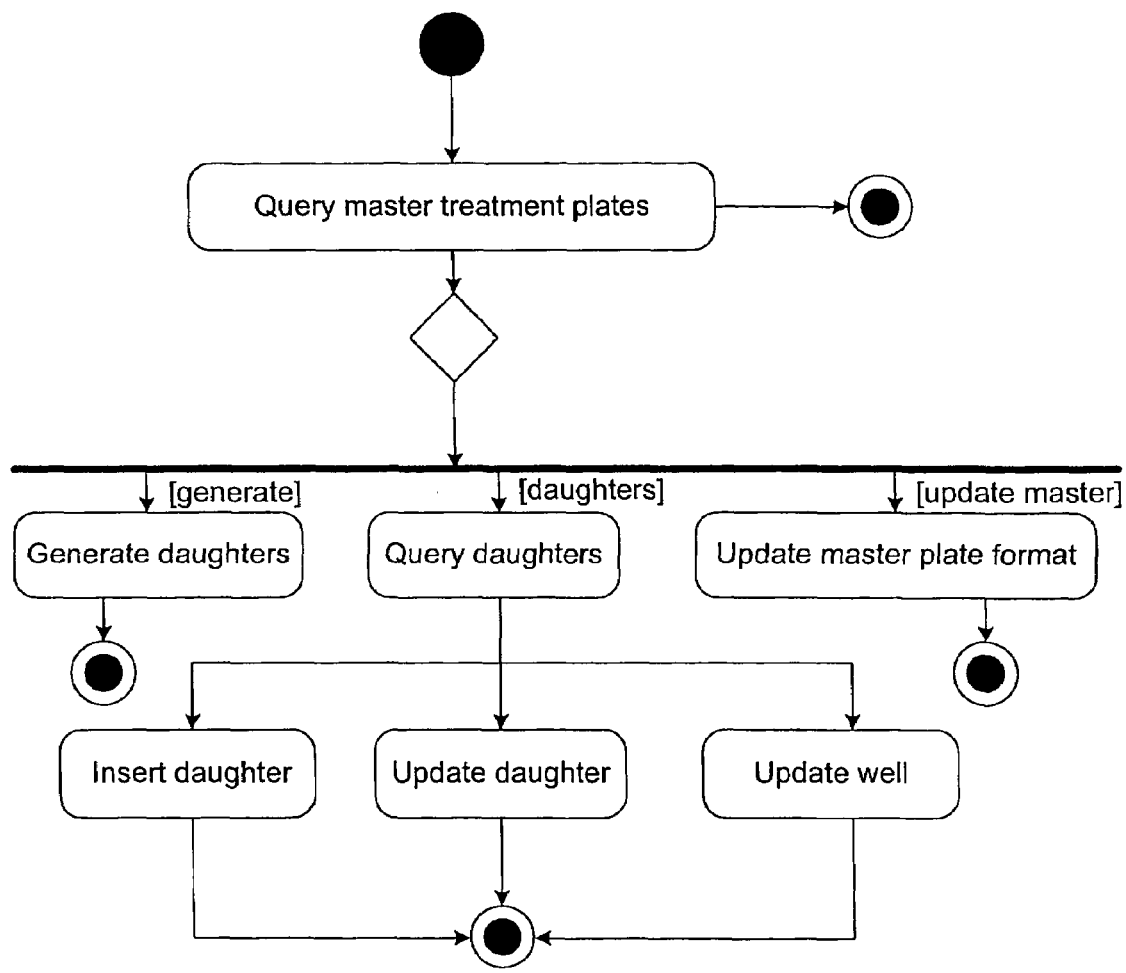
FIG. 15C depicts a basic process flow through the treatment plate generator form in accordance with an embodiment of this invention.

The basic flow through the treatment plate generator form includes the activities depicted in FIG. 15C.

Process Tracking System

Cytometrix™ operates as a collection of systems interacting to run, track, and validate experiments. To validate processes and products, the system contains a feedback mechanism that provides information relating to the success or failure of any Cytometrix system.

A system failure occurs when an event happens as a result of system operation that departs from the requirements for the system. A system opportunity occurs when a system user or developer realizes that there is an opportunity to solve a problem in a better way or to improve operation of the system (synonyms: suggestion, enhancement). A system comment occurs when a system user gives some kind of feedback about the system other than a departure from requirements of a suggestion for improvement. All three events are a kind of system feedback that injects information into the automated system.

Note that modern quality assurance practice distinguishes between the "failures" of a system and the "faults" that cause those failures. As used herein, the term "defect" corresponds to the concept of fault. There is a many-to-many relationship between these concepts: a fault may cause many failures, and a failure may result from faults in several systems. The Process Tracking System addresses failure feedback, not fault tracking.

The process tracking system provides an information system that lets users (including developers), applications, and database servers create and track system failures. It provides applications that enable management to plan improvement work based on prioritization of the failures and to understand the current situation with respect to the life cycle of failures in the overall system. Managers can also use this system to improve the visibility of failures within the organization and to improve communication with respect to failures.

The process tracking system also provides an information system that lets users (including developers) suggest and track improvement opportunities. Provide applications that enable management to plan improvement work based on prioritization of the opportunities. Managers can also use this system to improve the visibility and communication of progress in realizing opportunities within the organization.

Finally, the process tracking system provides an information system that lets users make comments on operational systems. To this end, it provide applications that enable management to plan improvement work based on prioritization of the comments.

Figure 16A:
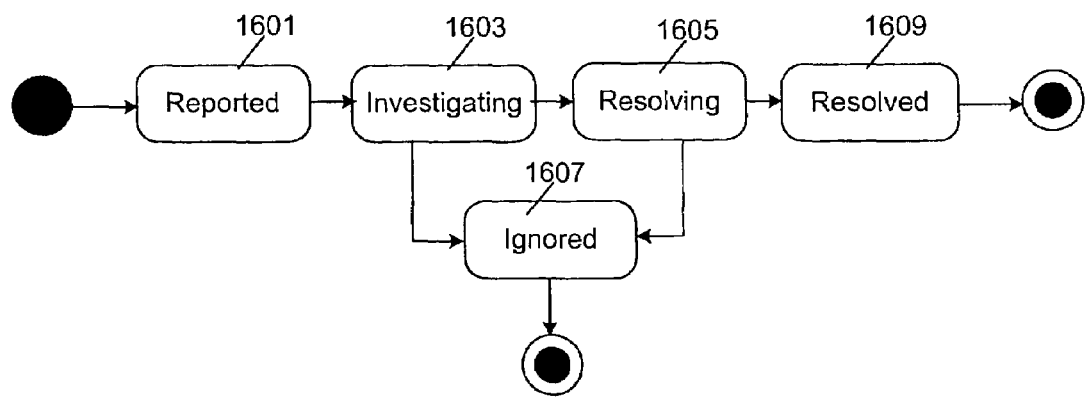
FIG. 16A depicts a failure life cycle associated with a process tracking system of this invention.

In one embodiment, a failure life cycle appears as shown in FIG. 16A. When the user creates a failure, it has status Reported 1601. A Manager assigns the failure to an Investigator, changing the status to Investigating 1603 until the Investigator or a Manager puts it into Resolving 1605 by assigning the problem to Development to discover the cause of the failure and fix it or decides to Ignore the problem, putting it into the Ignored state 1607. Resolving means that someone is working on fixing the failure. Again, a manager may decide to ignore the failure by putting it into the Ignored state from Resolving. Finally, when Development reports that the problem is fixed, a Manager verifies the fix and changes the status to Resolved 1609. When the failure is resolved, the life cycle ends.

Figure 16B:
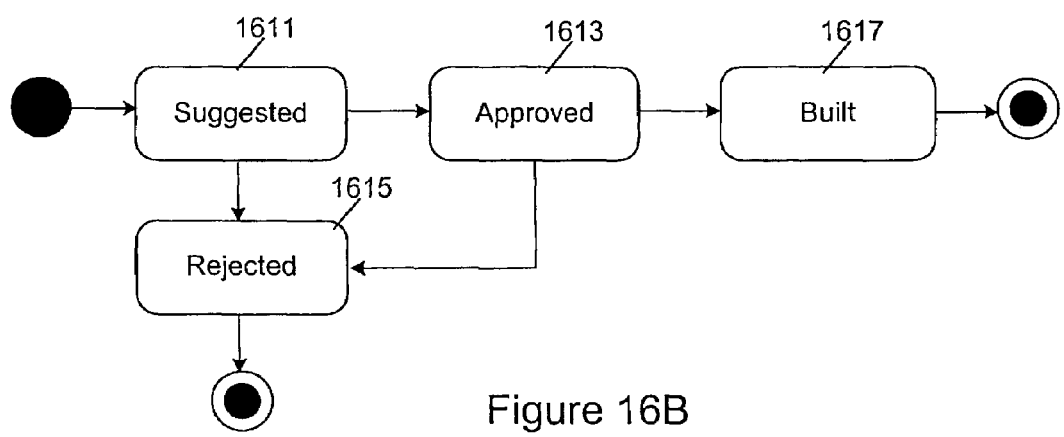
FIG. 16B depicts an opportunity life cycle associated with a process tracking system of this invention.

The opportunity life cycle appears as shown in FIG. 16B. When a user or developer suggests an opportunity, it has status Suggested 1611. A Manager either approves the suggestion and assigns it to a Developer or rejects the suggestion. In the former case, the status becomes Approved 1613; in the latter, Rejected 1615. When the Developer integrates the changes into the system, the status changes to Built 1617. It is also possible for a Manager to decide to reject an approved opportunity, moving the status from Approved to Rejected.

Figure 16C:
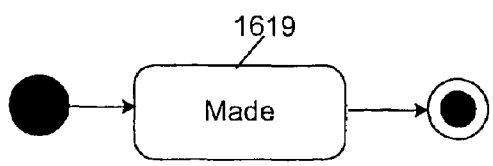
FIG. 16C depicts a comment life cycle associated with a process tracking system of this invention.

A comment life cycle, as depicted in FIG. 16C, has one state, Made 1619. In one embodiment, the system does not support any other process relating to comments.

Priorities may be set to a number between 0 and 1, with 0 being lowest priority and 1 being highest priority. The text priorities may appear in form input fields, but the database will represent the priorities as decimal numbers to use in calculating the weighted metrics.

Figure 16D:
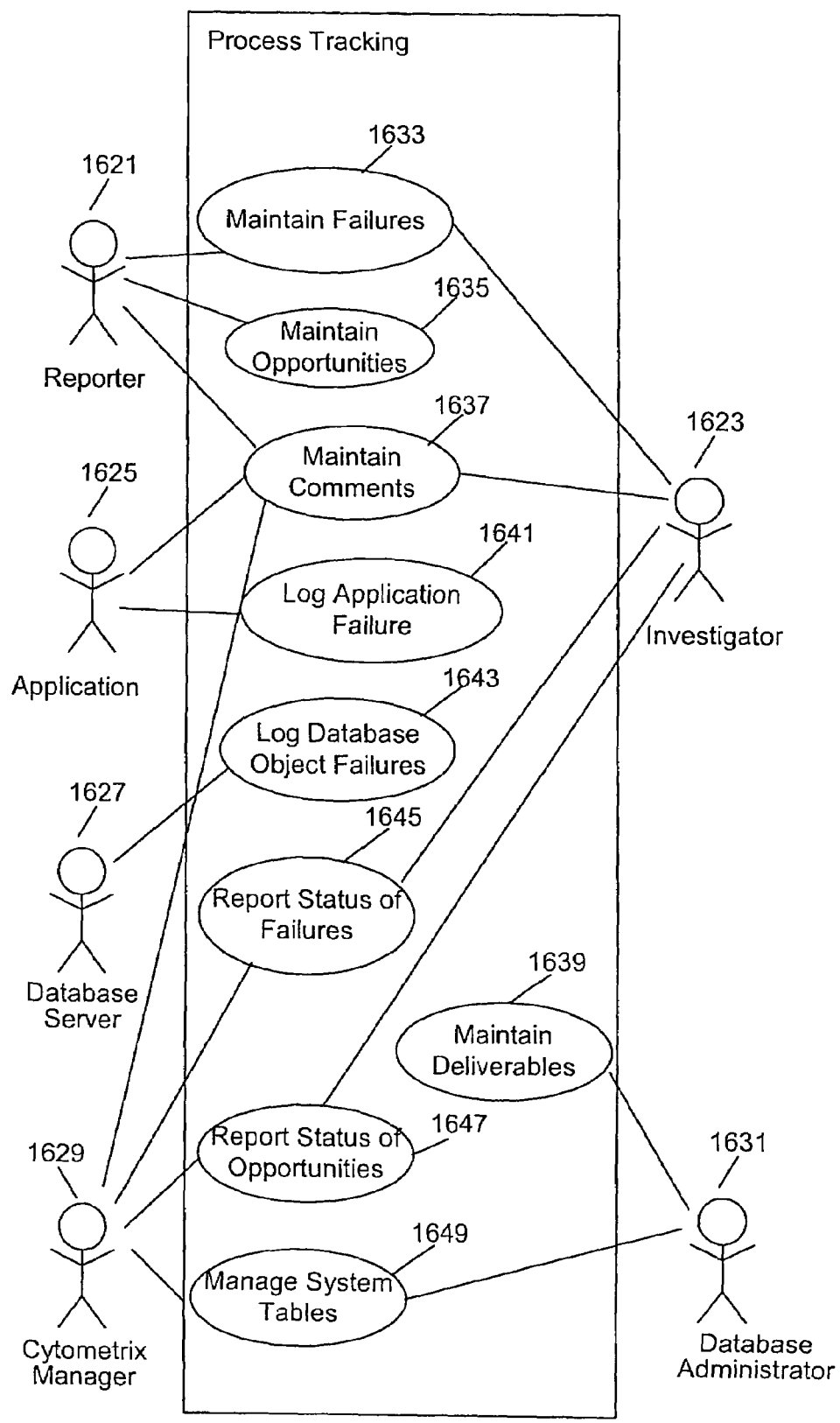
FIG. 16D depicts various use cases associated with a process tracking system of this invention.

The actors in the Process Tracking System are both human and automated. As depicted in FIG. 16D, they include the following. A Reporter 1621 is any individual with authority to report a failure of, suggest an opportunity for, or comment on a Cytometrix™ system. An Investigator 1623 is any individual assigned the responsibility for investigating the causes of a failure or the usefulness of an opportunity. An Application 1625 is any running program that can access the failure database to log a failure in the program. A Database Server 1627 is any running server process that can access the failure database to log a failure on the database server. A Manager 1629 is an individual with responsibility for planning and control of Cytometrics systems. A Database Administrator 1631 is an individual with responsibility for maintaining database tables in the Information Management System schema An Information Management System Database (not shown) is the schema and storage dedicated to managing information about the automated system as a product. Investigators are also Reporters, as are Managers. Investigators are also Discoverers in the Defect Tracking subsystem.

As depicted in FIG. 16D, the use cases for the Process Tracking System represent the transactions the various actors can undertake in the system.

A Maintain Failures use case 1633 may be understood as follows. A failure occurs when a system fails to perform its intended purpose. A Reporter enters or modifies failures. Investigators and Managers are also Reporters but have special privileges to add resolutions and set management priority.

Some processes for the Maintain Failures use case 1633 are depicted in Table 24.

TABLE 24

| Actor | System |
| --- | --- |
| Optionally, query a set of failures. | Retrieve the set, displaying ID, description, resolution, management priority, user priority, the ordered list of status changes, any linked defects, and any linked opportunities. |
| Create a new user failure, specify the failing system, and supply the description of the failure and the management and user priority of the failure. | Insert the user failure report into the Database, supplying a unique ID and creating an initial status history of Reported with a time stamp and changer (based on the Oracle username). The owner is the Reporter. |
| Modify an existing failure by editing the description, supplying or editing a resolution description, or changing the user priority. | Modify the failure report in the Database. |

Various extensions are possible with this use case.

Extension 1: If a Manager decides to change the status of a failure, he or she sets the status to an appropriate value (see failure life cycle) and optionally changes the owner of the failure to another person and/or sets the management priority.

Extension 2: If a Investigator or Manager sees a relationship between one or more defects and a failure, the Investigator or Manager may link the failure to the defects by extending the use case. This permits management to resolve failures by fixing defects and then tracking the failure resolution through the fixing of the defects.

Extension 3: If an Investigator or Manager sees a relationship between a failure and an opportunity, the Investigator or Manager may link the failure to the opportunity by extending the use case. This permits management to resolve failures by creating opportunities and then track the failure resolution through opportunity implementation.

A Maintain Opportunities use case 1635 may involve a Reporter suggesting or modifying opportunities. Investigators and Managers track the opportunities. Table 25 elaborates.

TABLE 25

| Actor | System |
| --- | --- |
| Optionally, query a set of opportunities, | Retrieve the set, showing ID, description, target release, actual release, suggestor priority, management priority, the ordered list of status changes, any linked components, and any linked failures. |
| Create a new opportunity and supply the description of the opportunity and the suggested priority of the opportunity. | Insert the opportunity into the Database, supplying a unique ID and creating an initial status history of Suggested with a time stamp and changer (based on the Oracle username). |
| Modify an existing opportunity by editing the description, changing the status to an appropriate value (see opportunity life cycle), supplying a resolution description (with a change to status Resolved) or modifying an existing one, or supplying a management priority for the opportunity. | Modify the opportunity in the Database, creating a revision status history with a time stamp, changer (based on the Oracle username), and the status the user sets. |

In a Maintain Comments use case 1637, a Reporter makes, modifies, or tracks comments as indicated in Table 26.

TABLE 26

| Actor | System |
| --- | --- |
| Optionally, query a set of comments. | Retrieve the set, showing ID, description, and priority and any links to the automated system. |
| Make a comment, supplying the description of the comment and its suggested priority. | Insert the comment into the Database, supplying a unique ID and creating an initial status history of Made with a time stamp and changer (based on the Oracle username). |
| Modify an existing comment by editing the description or changing the priority. | Modify the comment in the Database, setting the new description and priority. |

A Maintain Deliverables use case 1639 may be understood as follows. A Database Administrator enters, changes, or removes deliverables from the system. A deliverable is a reusable system that is one of several kinds of system that delivers value to a customer (a product document, a hardware system, or a software system). Deliverables can be a major source for failures. Exemplary processes for this use case are depicted in Table 27.

TABLE 27

| Actor | System |
| --- | --- |
| Create a new deliverable, specifying the deliverable name, type (Document, Hardware, Software), description, project data (planned value, earned value, actual value, actual cost), and system characteristics (vision, mission, risk, objectives, and so on). | Create the deliverable in the database, generating a unique identifier and displaying it. |
| Query a deliverable based on ID, name, type, or description. | Display the query result set, displaying ID, name, type, and description. Display only active deliverables (inactive is false). |

TABLE 27-continued

| Actor | System |
|---|---|
| Modify the name, type, and/or description of the deliverable, | Store the changes in the database. If the type changes, remove the existing objects and replace them in the correct tables. |
| Remove the deliverable. | Mark the deliverable inactive in the database. |

A Log Application Failure use case 1641 may be understood as follows. Application software systems log their failures to the Experiment database as application failures. See Table 28 for a sample process.

TABLE 28

| Actor | System |
|---|---|
| Create an application failure, specifying the error number, the name of the software system actor logging the error, the namespace and name of the failing module, and error ("description") and context messages. | Insert the failure into the Database, supplying a unique ID, creating an initial status history of Reported with a timestamp and changer (based on the program name), and linking the application failure to the indicated module. |

In a Log Database Object Failure use case 1643, the database server can log a failure in a database object in the automated system Database. An exemplary process for this use case is depicted in Table 29.

TABLE 29

| Actor | System |
|---|---|
| Create a database object failure, specifying the error number; the name of the software system actor logging the error; schema, object type, and name of the failing object; and error ("description") and context messages. | Insert the failure into the Database, supplying a unique ID, creating an initial status history of Reported with a timestamp and changer (based on the Oracle username), and linking the failure to the indicated schema object. |

Two possible extensions to this use case follow.

Extension 1: If the program logging the error does not exist in the configuration database, the logger raises an application exception.

Extension 2: If the system cannot insert the failure into the database for some reason, the logger raises an application exception. One reason might be that the database object does not exist in the configuration database, for example.

A Report Status of Failures use case 1645 may be understood as follows. The Investigator and Manager can generate a report of failure status from the system Database.

Note that in a typical system there are three types of failure: user failures, application failures, and database object failures. Each type has some special report needs. These may be separate reports or they may be sections in a single report, or you might figure out a way to combine them into a single report with one section. Table 30 presents more information.

TABLE 30

| Actor | System |
|---|---|
| Request a status report, specifying the inclusive status change dates between which to select failures (default all failures) and a minimum management priority (default 0). | Generate a report displaying the current failure status, failure ID, description, status date, reusable system ID and name, owner ID and name, resolution, management priority, and user priority. Break on status. Order by status and failure ID. |

Extension 1: If the report lists user failures, display the user priority.

Extension 2: If the report lists application failures, display the system error ID, the system error message, and the context.

Extension 3: If the report lists database object failures, display the database identifier, schema name, schema object name, system error ID, system error message, and context.

In a Report Status of Opportunities use case 1647, the Investigator and Manager can generate a report of opportunity status from the automated system Database. See Table 31.

TABLE 31

| Actor | System |
|---|---|
| Request a status report, specifying the inclusive status change dates between which to select opportunities (default all opportunities), a minimum management priority (default 0), and a person who was the last person to change the status of the opportunity. | Generate a report ordered by priority and breaking on last reported status displaying the opportunity ID, system ID and name, description, resolution, suggestor priority, and management priority. |

In a Manage System Tables use case 1649, the Database Administrator manages the various tables that support the Process Tracking process. See Table 32.

TABLE 32

| Actor | System |
|---|---|
| Optionally, query a set of data. | Retrieve the set, displaying all the columns from the table. |
| Create a new row and supply whatever data is required. | Insert the new row, creating new ID as required. |
| Modify an existing row by changing data as appropriate. | Modify the row in the Database as specified. |

Tables to administer include the following: Problem Status, System Error, and Actor (including people, organizations, and programs).

Defect Tracking System

A system defect or fault is a flaw in a reusable system that has the potential to cause the system to fail to achieve its mission. A Defect Tracking System should provide consistent, easily accessed feedback about defects in automated systems to management in a persistent format. The associated information system should let users (including developers), applications, and database servers create and track system defects. It should provide applications that enable management to plan improvement work based on prioritization of defect fixing and to understand the current situation with respect to the life cycle of defects in the overall system. Managers can also use this system to improve the visibility of defects within the organization and to improve communication with respect to defects.

Figure 16E:
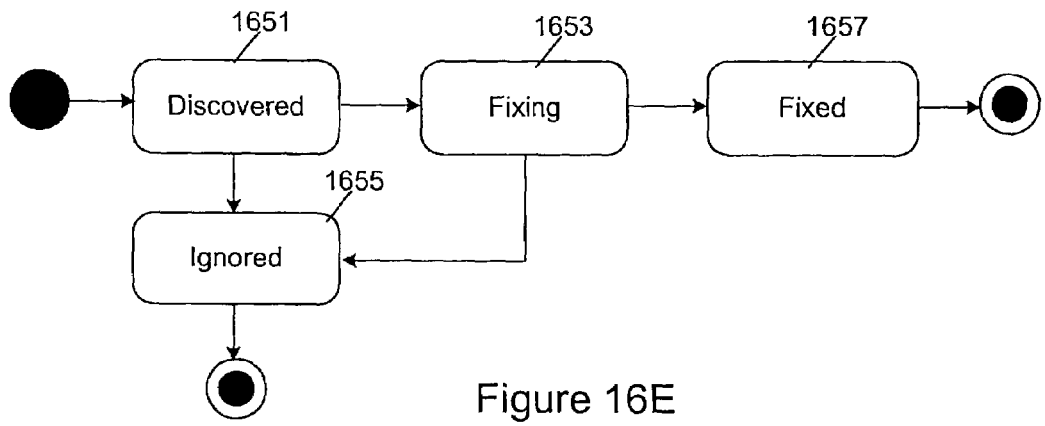
FIG. 16E depicts a defect life cycle associated with a defect tracking system of this invention.

The defect life cycle appears as shown in FIG. 16E. When a user discovers a defect, it has status Discovered 1651. Management may then decide to get the defect fixed (Fixing 1653) or to ignore the defect (Ignored 1655). When the defect is in Fixing status, it moves to Fixed status 1657 when the user integrates the defect fix into the configuration management system and tests the fix. It is also possible for a manager to decide to ignore the defect after trying for awhile to fix it. When a failure moves to the Ignored state 1655 or to the Fixed state 1653, the life cycle ends.

Figure 16F:
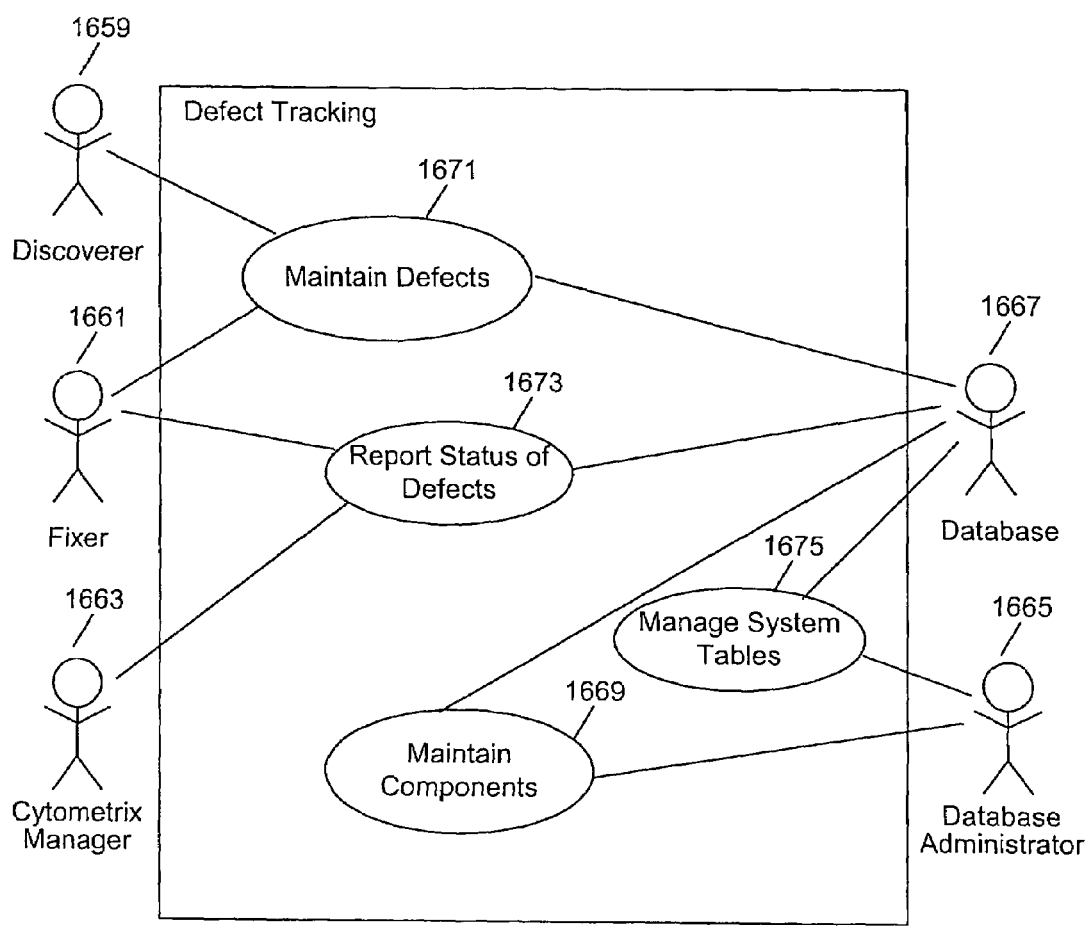
FIG. 16F depicts various use cases associated with a failure tracking system of this invention.

The actors in a the Failure Tracking System are depicted in FIG. 16F. They may be both human and automated. A Discoverer 1659 is any individual with authority to report a defect in a Cytometrix™ system. A Fixer 1661 is any individual assigned the responsibility for investigating the root causes of the defect and for implementing a fix to the defect. A Manager 1663 is an individual with responsibility for planning and control of automated systems. A Database Administrator 1665 is an individual with responsibility for maintaining database tables in the Information Management System schema An Information Management System Database 1667 is the schema and storage dedicated to managing information about the automated system as a product. Fixers may also be Discoverers, as are Managers.

As illustrated in FIG. 16F, the use cases for the Failure Tracking System represent the transactions the various actors can undertake in the system. A Maintain Components use case 1669 may be understood as follows. A Database Administrator enters, changes, or removes components from the system. A component is a reusable system that is either a module (hardware, software, database, or file) or a subsystem comprising several modules. Components are the major source for defects that cause failures in deliverables and other systems (see the Process Tracking System Use Cases for details on failures). In particular, all system failures logged automatically are logged against a component. Table 33 provides some relevant processes for the Maintain Components use case 1669.

TABLE 33

| Actor | System |
|---|---|
| Create a new component, specifying the component name, type (Subsystem, Hardware, Software, Database, or File), description, and system characteristics (vision, mission, risk, objectives, and so on). | Create the component in the database, generating a unique identifier and displaying it. |
| Query a component based on ID, name, type, or description. | Display the query result set, displaying ID, name, type, and description. Display only active components (inactive is false). |
| Modify the name, type, and/or description of the component. | Store the changes in the database. If the type changes, remove the existing objects and replace them in the correct tables. |
| Remove the component. | Mark the component inactive in the database. |

In a Maintain Defects use case 1671, a Discoverer enters system defects and modifies or tracks them. Fixers and Managers are also Discoverers but have special privileges to change status and to set management priorities. See Table 34.

TABLE 34

| Actor | System |
|---|---|
| Optionally, query a set of defects for a component system. | Retrieve the set, displaying component name, ID, description, cause, fix description, priority, the ordered list of status changes, and any linked failures |
| Create a new defect for a component, identify the system that is defective, and supply the description of the defect and the priority of the failure. | Insert the defect report into the Database, supplying a unique ID and creating an initial status history of Discovered with a time stamp and changer (based on the Oracle username). |
| Modify an existing defect by editing the description, changing the status to an appropriate value (see defect life cycle), supplying or modifying a cause, supplying or modifying a fix description (with a change to status Fixed), or modifying the priority for the defect. | Modify the defect report in the Database, creating a revision status history with a time stamp, changer (based on the Oracle username), and the status the user sets. |

In a Report Status of Defects use case 1673, the Fixer and Manager can generate a report of defect status from the automated system Database. See Table 35.

TABLE 35

| Actor | System |
|---|---|
| Request a status report, specifying the inclusive dates between which to select defects (default all failures) and a minimum priority (default 0). | Generate a report displaying the defect status, defect ID, description, system ID and name, owner ID and name, cause, fix description, and priority. Break the report on status. Order the report by status and priority. |

In a Manage System Tables use case 1675, the Database Administrator manages the various tables that support the failure tracking process. See Table 36.

TABLE 36

| Actor | System |
|---|---|
| Optionally, query a set of data. | Retrieve the set, displaying all the columns from the table. |
| Create a new row and supply whatever data is required. | Insert the new row, creating new ID as required. |
| Modify an existing row by changing data as appropriate. | Modify the row in the Database as specified. |

Tables to administer include the following: ProblemStatus, ObjectType, and Language.

Defect Report

The Defect Report provides a sorted list of defects with status Discovered or Fixing. The report provides information on defects to a Quality Review Board, for example, for management and prioritization of defect fixing. The report is sorted into those two status categories (in that order), then by descending priority (highest priority first). Within each status grouping, the report displays the defect ID, the description, the system against which the defect was logged, the priority, the current owner of the defect, and a list of failures that the defect causes. The report lets you specify a date range for the last status date change and a minimum priority to display, letting you list defects changed between certain dates and defects at or above a certain priority. QRB members and managers should be able to access a current version of the report on demand, either as an HTML file or as a PDF (Adobe Acrobat document).

There are only two significant actors beyond those specifically discussed in the context of the Defect Tracking use cases (FIG. 16F). These are a QRB Member 1679, who is a member of the Quality Review Board, and a Manager 1681, who is a departmental manager. See FIG. 16G.

Figure 16G:
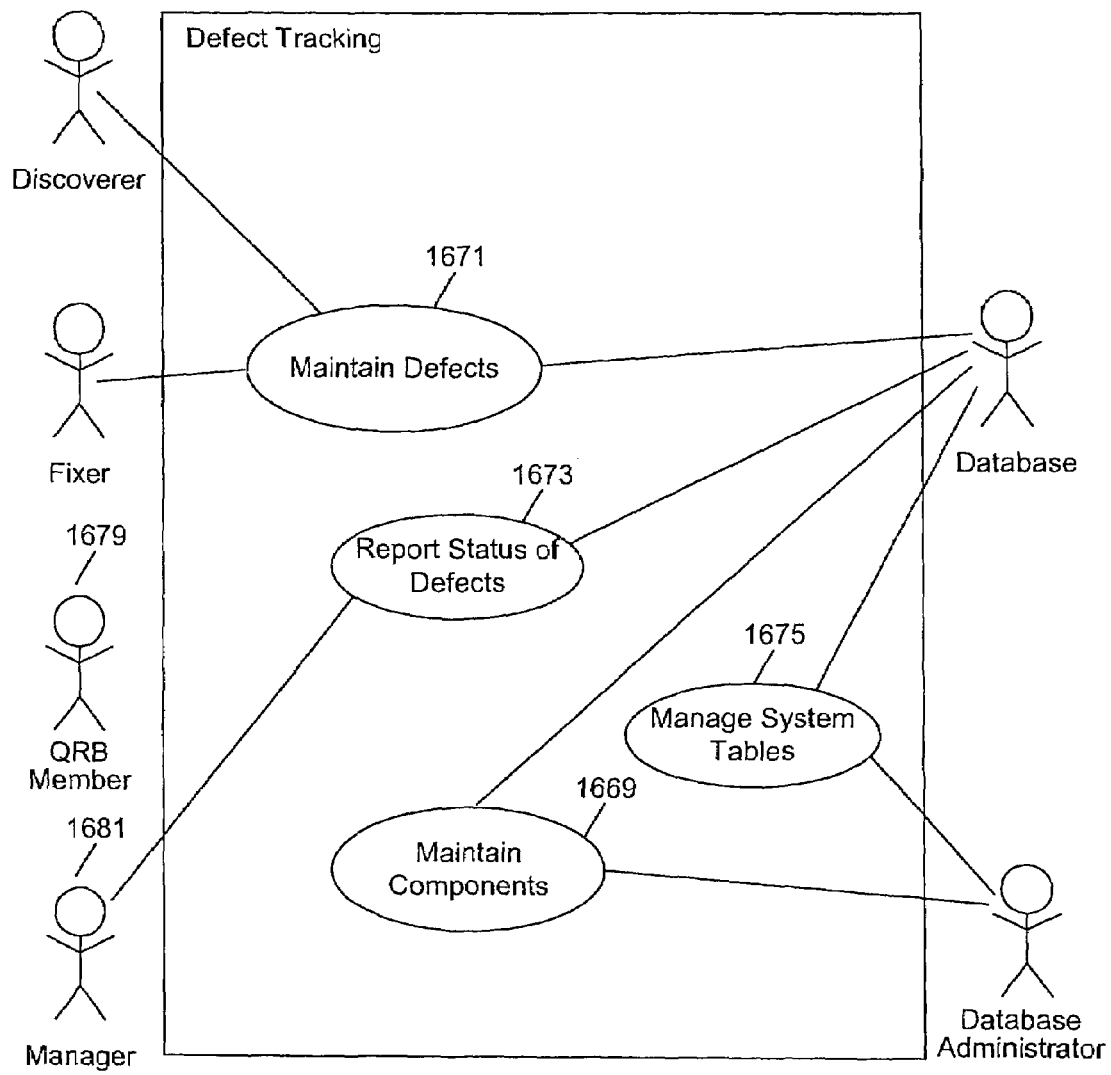
FIG. 16G depicts various use cases associated with a defect report system of this invention.

The Defect Report system is part of the Defect Tracking system. The context diagram of FIG. 16G shows the Report Status of Defects use case in the context of the other use cases in the Defect Tracking system.

The Report Status of Defects use case 1673 was touched on above. In this use case, the Manager or QRB Member generates a current Defect Report. The user can specify a date range for the last status change; this selects defects that have changed during that time interval. The user can also specify a minimum priority; this selects defects at or above that priority (on a scale of 0 to 100, where 0 is lowest priority and 100 is highest priority). Finally, the user can request a specific display format for the report (HTML or PDF).

The System displays a report in the requested format with the requested defects in Discovered and Fixing status. The report groups the defects into two groups in order: Discovered and Fixing.

During operation in this use case, the user runs the report. The system then displays the report in PDF format for all Discovered or Fixing defects at or above priority 50. The report groups the defects into two groups, in order: Discovered and Fixing. The report displays for each group the defect ID, defect description, system name, priority, current owner, and list of failures the defect causes.

In one extension, a user supplies a date range. The system subsets the defects to display only defects with the last status change occurring between the dates. In another extension, the user supplies priority between 0 and 100. In response, the system subsets the defects to display only defects with a priority greater than or equal to the supplied priority. In another extension, the user supplies HTML. The system displays the defect report in HTML in the web browser.

Other Embodiments

Although the above has generally described the present invention according to specific processes and apparatus, the present invention has a much broader range of applicability. In particular, the present invention is not limited to any particular kind of biological image data, but can be applied to virtually any cellular images or markers. It is not necessarily limited to the specific algorithms and calculations described herein. Further, the invention is not limited to any particular arrangement of selected hardware or software products. Rather the invention can be practiced with any combination of hardware and software products (whether or custom developed) that can provide the functions described herein. Thus, in some embodiments, the present invention could be implemented with numerous other products beyond those described herein. Of course, one of ordinary skill in the art would recognize other variations, modifications, and alternatives.

What is claimed is:

1. An automated method for analyzing a plurality of cellular images, the method comprising:
    from a plurality of image analysis tasks, automatically identifying a next image analysis task for execution;
    automatically selecting one of a plurality of feature extractor servers available to handle the next image analysis task;
    identifying an algorithm for extracting features as part of the next image analysis task; and
    executing the algorithm under the control of the selected feature extractor.

2. The method of claim 1, wherein the image analysis task characterizes a cellular organelle, a material in the cell, or a combination thereof.

3. The method of claim 2, wherein the image analysis task is selected from the group consisting of determining the shape of a cell, characterizing the nucleic acid of a cell, characterizing the Golgi of a cell, and combinations thereof.

4. The method of claim 1, wherein a supervisor software entity identifies the next image task and selects the feature extractor server to handle the next image analysis task.

5. The method of claim 1, further comprising importing the identified algorithm into the selected feature extractor for execution.

6. The method of claim 1, further comprising inputting one or more selected cellular images required for the image analysis task.

7. The method of claim 6, further comprising generating the one or more selected cellular images using a process model generated by an automated laboratory experiment manager for designing the biological experiment.

8. The method of claim 1, further comprising inputting parameters required to execute the algorithm from a database.

9. The method of claim 1, further comprising returning the feature extractor server to a queue of available feature extractor servers after the image analysis task is completed.

10. The method of claim 1, further comprising:
    receiving data representing a design of a biological experiment defining an assay plate and comprising one or more processes involving forming at least one image of at least a portion of at least one well of the assay plate; and
    directing the biological experiment in accordance with the data to generate the at least one of the plurality of cellular images from at least a portion of at least one well of the assay plate.

11. An automated system for conducting, monitoring, and validating a cell-line-based biological experiment including a treatment compound, the system comprising:
    an automated laboratory experiment manager for designing the biological experiment, for constructing an assay plate used to conduct the biological experiment, and for managing one or more of the processes that constitute the biological experiment, including the formation of an image of at least a portion of at least one well of the assay plate; and
    an automated data analysis manager for analyzing the image produced by the automated laboratory experiment manager to detect image data including biological markers, for analyzing the resulting image data to produce biological data, and for analyzing the biological data to produce quantitive phenotypes and treatment compound signatures.

12. The automated system of claim 11, wherein the automated laboratory experiment manager facilitates specification of the biological experiment through a process model that generates a collection of tasks.

13. The automated system of claim 11, wherein the automated data analysis manager comprises a supervisor that sends task requests to a plurality of feature extractor servers that execute algorithms comprising the tasks.

14. The automated system of claim 11, further comprising an image production system for performing photomicroscopy of at least a portion of the assay plate responsive to directions from the laboratory experiment manager, thereby producing an image of the at least a portion of the assay plate.

15. The automated system of claim 11, further comprising a database system for storing data including at least one of the image, the image data, the biological data, the biological phenotypes and treatment compound signatures.

16. The automated system of claim 11, further comprising a report generator for providing secure access to the data stored in the database system, and, responsive to a user request, for generating a report compiled from the data.

17. The automated system of claim 11, further comprising a defect tracking system for tracking defects within the automated system.

18. The automated system of claim 11, further comprising a process tracking system for running, tracking, and validating experiments provided by the automated system.

19. The automated system of claim 11, further comprising a defect report system for providing a sorted list of defects detected in the automated system.

20. The automated system of claim 11, further comprising an experiment wizard providing a user interface that presents a plurality of pages for entering parameters defining an experiment.

* * * * *